US009528089B2

(12) United States Patent
Hirashima et al.

(10) Patent No.: US 9,528,089 B2
(45) Date of Patent: Dec. 27, 2016

(54) METHOD FOR INCREASING THE PROPORTION OF ANIMAL CELLS SECRETING GALECTIN-9

(71) Applicant: GALPHARMA CO., LTD., Kagawa (JP)

(72) Inventors: Mitsuomi Hirashima, Kagawa (JP); Toshiro Niki, Kagawa (JP); Tomohiro Arikawa, Ishikawa (JP); Souichi Oomizu, Kagawa (JP); Takeshi Kadowaki, Kagawa (JP)

(73) Assignee: GALPHARMA CO., LTD., Kagawa (JP)

( * ) Notice: Subject to any disclaimer, the term of this patent is extended or adjusted under 35 U.S.C. 154(b) by 0 days.

(21) Appl. No.: 14/499,736

(22) Filed: Sep. 29, 2014

(65) Prior Publication Data

US 2015/0093366 A1    Apr. 2, 2015

Related U.S. Application Data

(62) Division of application No. 13/992,018, filed as application No. PCT/JP2011/078623 on Dec. 9, 2011, now abandoned.

(30) Foreign Application Priority Data

Dec. 9, 2010   (JP) ................. 2010-274467

(51) Int. Cl.
| | |
|---|---|
| C12N 5/078 | (2010.01) |
| A61K 35/17 | (2015.01) |
| C12N 5/07 | (2010.01) |
| C12N 5/0783 | (2010.01) |
| G01N 33/68 | (2006.01) |
| A61K 49/00 | (2006.01) |
| C12N 5/0781 | (2010.01) |
| C12N 5/0784 | (2010.01) |
| G01N 33/50 | (2006.01) |
| G01N 33/569 | (2006.01) |
| C12N 5/0786 | (2010.01) |

(52) U.S. Cl.
CPC ............ *C12N 5/0646* (2013.01); *A61K 35/17* (2013.01); *A61K 49/0004* (2013.01); *C12N 5/0635* (2013.01); *C12N 5/0636* (2013.01); *C12N 5/0637* (2013.01); *C12N 5/0639* (2013.01); *C12N 5/0645* (2013.01); *G01N 33/5094* (2013.01); *G01N 33/56972* (2013.01); *G01N 33/68* (2013.01); *C12N 2501/59* (2013.01); *G01N 2333/42* (2013.01); *G01N 2333/4724* (2013.01); *G01N 2333/705* (2013.01)

(58) Field of Classification Search
None
See application file for complete search history.

(56) References Cited

U.S. PATENT DOCUMENTS

| | | | |
|---|---|---|---|
| 2006/0134119 | A1 | 6/2006 | Hirashima et al. |
| 2007/0042941 | A1 | 2/2007 | Hirashima et al. |
| 2008/0044385 | A1 | 2/2008 | Nishi et al. |
| 2010/0203628 | A1 | 8/2010 | Nishi et al. |

FOREIGN PATENT DOCUMENTS

| | | |
|---|---|---|
| CN | 1795206 | 6/2006 |
| JP | 2003-189874 | 7/2003 |
| JP | 2004-244411 | 9/2004 |
| JP | 2006-124299 | 5/2006 |
| JP | 2007-131540 | 5/2007 |
| JP | 2007-137774 | 6/2007 |
| JP | 2007-209328 | 8/2007 |
| KR | 2007-0031887 | 3/2007 |
| WO | 2005/093064 | 10/2005 |
| WO | 2005/121340 | 12/2005 |
| WO | 2007/018229 | 2/2007 |

OTHER PUBLICATIONS

Mengshol et al., A crucial role for Kupfer cell-derived Galectin-9 in regulation of T cell immunity in hepatitis C infection, PLoS One, 5, e9504, Mar. 2010.*
Zhou et al.—Plasticity of CD4+FoxP3+ T cells—Curr. Opin. Immunol. 21, 281-285, 2009.*
Seki et al., Galectin-9 suppresses the generation of Th17, promotes the induction of regulatory T cells, and regulates experimental autoimmune arthritis. Clin. Immunol. 127, 78-88, 2008.*
Hirabayashi et al., "Oligosaccharide specificity of galactins: a search by frontal affinity chromatography", Biochimica et Biophysica Acta. vol. 1572, 2002, pp. 232-254.
Wada et al., "Developmental Regulation, Expression, and Apoptotic Potential of Galectin-9, a -Galactoside Binding Lectin", Journal of Clinical Investigation, vol. 99, No. 10, May 1997, pp. 2452-2461.
Matsumoto et al., "Human Ecalectin, a Variant of Human Galectin-9, Is a Novel Eosinophil Chemoattractant Produced by T Lymphocytes", The Journal of Biological Chemistry, vol. 273, No. 27, Jul. 3, 1998, pp. 16976-16984.
Zhu et al., "The Tim-3 ligand galectin-9 negatively regulates T helper type 1 immunity", Nature Immunology, vol. 6, No. 12, Dec. 2005, pp. 1245-1252.
Chen et al., "Anti-IL-23 therapy inhibits multiple inflammatory pathways and ameliorates autoimmune encephalomyelitis", The Journal of Clinical Investigation, vol. 116, 2006, pp. 1317-1326.
Nakae et al., "Phenotypic differences between Th1 and Th17 cells and negative regulation of Th1 cell differentiation by IL-17", Journal of Leukocyte Biology, Volo. 81, May 2008, pp. 1258-1268.
Seki et al., "Galectin-9 suppresses the generation of Th17, promotes the induction of regulatory T cells, and regulates experimnental autoimmune arthritis", Clinical Immunology, vol. 127, 2008, pp. 78-88.

(Continued)

*Primary Examiner* — Elly-Gerald Stoica
(74) *Attorney, Agent, or Firm* — Wenderoth, Lind & Ponack, L.L.P.

(57) ABSTRACT

The object of the present invention is to provide a cell that can exhibit physiological activity based on galectin-9, a method for producing the cell, and use of the cell. In order to achieve the above object, the cell of the present invention contains galectin-9, and the galectin-9 is expressed on a cell surface.

14 Claims, 37 Drawing Sheets

(56) References Cited

OTHER PUBLICATIONS

Arikawa et al., "Galectin-9 expands immunosuppressive macrophages to ameliorate T-cell-mediated lung inflammation", European Journal of Immunology, vol. 40, 2010, pp. 548-558.

Tsuboi et al., "Galectin-9 protects mice from the Shwartzman reaction by attracting protaglandin E2-producing polymorphonuclear leukocytes", Clinical Immunology, vol. 124, 2007, pp. 221-233.

Dardalhon et al., "Tim-3/Galectin-9 Pathway: Regulatoion of Th1 Immunity through Promotion of CD11b+Ly6G+ Myeloid Cells", The Journal of Immunology, vol. 185, 2010, pp. 1383-1392.

Nobumoto et al., "Galectin-9 expands unique macrophages exhibiting plasmacytoid dendritic cell-like phenotypes that activate NK cells in tumor-bearing mice", Clinical Immunology, vol. 130, 2009, pp. 322-330.

Niki et al., "Galectin-9 Is a High Affinity IgE-binding Lectin with Anti-allergic Effect by Clocking IgE-Antigen Complex Formation", The Journal of Biological Chemistry, vol. 284, No. 47, pp. 32344-32352.

Anderson et al., "Promotion of Tissue Inflammation by the Immune REceptor Tim-3 Expressed on Innate Immune Cells", Science, vol. 318, 2007, pp. 1141-1143.

Jayaraman et al., "Tim3 binding to galectin-9 stimulates antimicrobial immunity", The Journal of Experimental Medicine, vol. 207, No. 11, pp. 2343-2354.

Katoh et al., "Galectin-9 Inhibits CD44-Hyaluronan Interaction and Suppresses a Murine Model of Allergic Asthma", American Journal of Respiratory and Critial Care Medicine, vol. 176, 2007, pp. 27-35.

Nobumoto et al., "Galectin-9 suppresses tumor metastasis by clocking adhesion to endothelium and extracellular matrices", Glycobiology, vol. 18, No. 9, 2008, pp. 735-744.

Mishra et al., "Galectin-9 trafficking regulates apical-basal polarity in Madin-Darby canine kidney epithelial cells", PNAS, vol. 107, No. 41, Oct. 12, 2010, pp. 17633-17638.

Tanikawa et al., "Galectin-9 induces osteoblast differentiation through the CD44/Smad signaling pathway", Biochemical and Biophysical Research Communications, vol. 394, 2010, pp. 317-322.

Chabot et al., "Regulation of galectin-9 expression and release in Jurkat T cell line cells", Glycobiology, vol. 12, No. 2, 2002, pp. 111-118.

Fujio et al., "The Family of IL-10-Secreting CD4+ T Cells", Advances in Immunology, vol. 105, 2010, pp. 99-130.

Ochi et al., "Oral CD3-specific antibody suppresses autoimmune encephalomyelitis by inducing CD4+CD25-LAP+ T Cells", Nature Medicine, vol. 12, No. 6, Jun. 2006, pp. 627-635.

Okamura et al., "CD4+CD25-LAG3+ regulatory T cells controlled by the transcription factor Egr-2", PNAS, vol. 106, No. 33, Aug. 18, 2009, pp. 13974-13979.

Wakkach et al., "Characterization of Dendritic Cells that Induce Tolerance and T regulatory 1 Cell Differentiation in Vivo", Immunity, vol. 18, May 2003, pp. 605-617.

Jangpatarapongsa et al., "Plasmodium vivax parasites alter the balance of myeloid and plasmacytoid dendritic cells and induction of regulatory T cells", European Journal of Immunology, vol. 38, No. 10, 2008, pp. 2697-2705.

Kavousanaki et al., "Novel Role of Plasmacytoid Dendritic Cells in Humans", Arthritis & Rheumatism, vol. 62, No. 1m Jan. 2010, pp. 53-63.

Awasthi et al., "A dominant function for interleukin 27 in generating interleukin 10-producing anti-inflammatory T cells", Nature Immunology, vol. 8, No. 12, Dec. 2007, pp. 1380-1389.

Stumhofer et al., "Interleukins 27 and 6 induce STAT3-mediated T cell production of interleukin 10", Nature Immunology, Nov. 11, 2007, pp. 1-10.

Fitzgerald et al., "Suppression og autoimmune inflammation of the central nervous system by interleukin 10 secreted by interleukin 27-stiumlated T cells", Nature Immunology, vol. 8, No. 12, Dec. 2007, pp. 1372-1380.

Barrat et al., "In Vitro Generation of Interleukin 10-producing Regulatory CD4+ T Cells Is Induces by Immunosuppressive Drugs and Inhibited by T Helper Type 1 (Th1)- and Th2-inducing Cytokines", Journal of Experimental Medicine, vol. 195, No. 5, Mar. 4, 2002, pp. 603-616.

Uhlig et al., "Characterzation of Foxp3+CD4+CD25+ and IL-10-Secreting CD4+CD25+ T Cells during Cure of Colitis", The Journal of Immunology, vol. 177, 2006, pp. 5852-5860.

Maynard et al., "Regulatory T cells expressing interleukin 10 develop from Foxp3+ and Foxp3- precursor cells in the absence of interleukin 10", Naure Immunology, vol. 8, No. 9, Sep. 2007, pp. 931-941.

Nagahara et al., "Galectin-9 Increases Tim-3+ Dendritic Cells and CD8+ T Cells and Enhances Antitumor Immunity via Galectin-9-Tim-3 Interactions", The Journal of Immunology, 2008, pp. 7660-7669.

Nishi et al., "Development of highly stable galectins: Trunaction of the linker peptide confers protease-resistance on tandem-repeat type galectins", FEBS Letters, vol. 579, 2005, pp. 2058-2064.

Seki et al., "Benefitial Effect of Galectin 9 on Rheumatoid Arthritis by Induction of Apoptosis of Synovial Fibroblasts", Arthritis & Rheumatism, vol. 56, No. 12, Dec. 2007, pp. 3968-3976.

Wilson et al., "Development, cytokine profile and function of human interleukin 17-producing helper T cells", Nature Immunology, vol. 8, No. 9, Sep. 2007, pp. 950-957.

Oomizu et al., "Oral administration of pulverized Konjac glucomannan prevents the invrease of plasma immunoglobulin E and immunoglobulin G levels induced by the injection of syngeneic keratinocyte extracts in BLAB/c mice", Clinical and Experimental Allergy, vol. 36, 2006, pp. 102-110.

Lu et al., "Characterization of Galectin-9-Induced Death of Jrkat T Cells", Journal of Biochemistry, vol. 141, 2007, pp. 157-172.

Park et al., "A distinct lineage of CD4 T cells regulates tissue inflammation by producing interleukin 17", Nature Immunology, vol. 6, No. 11, Nov. 2005, pp. 1133-1141.

Laurence et al., "Interleukin-2 Signaling via Stats Constrains T Helper 17 Cell Generation", Immunity, vol. 26, Mar. 2007, pp. 371-381.

Mills, K., "Induction, function and regulation of IL-17-producing T cells", European Journal of Immunology, vol. 38, 2008, pp. 2636-2649.

Brun et al., "Clinical grade production of IL-10 producing regulatory Tr1 lymphocytes for cell therapy of chronic inflammatory diseases", International Immunopharmacology, vol. 9, 2009, pp. 609-613.

Levings et al., "Differentiation of Tr1 cells by immature dendritic cells requires IL-10 but not CD25+CD4+ Tr cells", Blood, vol. 105, 2005, pp. 1162-1169.

Roncarolo et al., "The validity of Foxp3 to define human and mouse regulatory T cells", European Journal of Immunology, vol. 38, 2008, pp. 901-937.

Kojima et al., "Galectin-9 Attenuates Acute Lung Injury by Expanding CD14- Plastacytoid Dendritic Cell-like Macrophages", American Journal of Respiratory and Critical Care Medicine, vol. 184, 2011, pp. 328-339.

Bettelli et al., "Recriprocal developmental pathways for the generation of pathogenic effector Th17 and regulatory T cells", Nature, vol. 441, No. 11, May 2006, pp. 235-238.

Kashio et al., "Galectin-9 Induces Apoptosis Thgouh the Calcium-Calpain-Caspase-1 Pathwayl", The Journal of Immunology, 2003, pp. 3631-3636.

Martin-Gayo et al., "Plasmacytoid dendritic cells resident in human thymus drive natural Treg cell development", Blood, vol. 115, No. 26, Jul. 1, 2010, pp. 5366-5375.

Supervisor: Rikuo Machinami, Editors: Junichi Hata & Atsuhiko Sakamoto, "Hyoujun Byourigaku", 2nd Edition, Igaku-Shoin ltd., Mar. 15, 2002, pp. 3 and 58-83, (with partial English translation).

Yamauchi et al., "Galectin-9 Induces Maturation of Human Monocyte-derived Dendritic Cells", Jpn. J. Clin. Immunol., vol. 28, No. 6, pp. 381-388, 2005, with English abstract.

Hirashima et al., "Galectin-9 in physiological and pathological conditions", Glycoconjugate Journal, vol. 19, pp. 593-600, 2004.

(56) References Cited

OTHER PUBLICATIONS

Dai et al., "Galectin-9 Induces Maturation of Human Monocyte-Derived Dendritic Cells", The Journal of Immunology, vol. 175, pp. 2974-2981, 2005.
Utsun et al., "Regulatory T cells in acute myelogenous leukemia: is it time for immunomodulation?", Blood, 118, pp. 5084-5095, 2011.
Liu et al., "Galectins in regulation of inflammation and immunity", Chapter 6, pp. 97-113, 2008.
Wang et al., "Tim-3-Galectin-9 pathway involves the suppression induced by CD4+CD25+ regulatory T cells", Immunobiology, pp. 342-349, 2009.
M. Hirashima, "Ecalectin/Galectin9, a novel eosinophil chemoattractant: its function and production", Int. Arch. Allergy Immunol., pp. 6-9, 2000.
Rodriguez-Manzanet et al., "The costimulatory role of TIM molecules", Immunol. Rev. 229, pp. 259-270, 2009.
de Kivit et al., "Intestinal epithelial cells exposed to synbiotics secrete galectin-9, which conditions dendritic cells to promote regulatory T-cell differentiation in vitro", Allergy 67, p. 51, 2012.
Notification of Reasons for Rejection issued Oct. 31, 2014 in corresponding Chinese Patent Application No. 201180059769.5 with partial English translation.
Partial Supplementary European Search Report issued May 4, 2015 in corresponding European Patent Application No. 11847227.3.

Bani et al., "Unstimulated Human CD4 Lymphocytes Express a Cytoplasmic Immature Form of the Common Cytokine Receptor γ-Chain", The Journal of Immunology, vol. 167, No. 1, pp. 344-349, (2001).
Oomizu et al., "Cell Surface Galectin-9 Expressing Th Cells Regulate Th17 and Foxp3$_+$Treg Development by Galectin-9 Secretion", PLOS ONE, vol. 7, No. 11, pp. 1-10, e48574, (2012).
Notification of Reasons for Rejection dated Feb. 3, 2016, of corresponding Japanese Application No. 2012-547938 (with partial English translation).
Boenisch et al., "TIM-3: A Novel Regulatory Molecule of Alloimmune Activation", The Journal of Immunology, 2010, vol. 185, No. 10, pp. 5806-5819.
Hirashima, "Ecalectin/Galectin-9, a Novel Eosinophil Chemoattractant: Its function and Production", Int. Arch. Allergy Immunol., 2000, vol. 122, Suppl. 1, pp. 6-9.
Notification of Reasons for Rejection issued Mar. 4, 2016 in corresponding Korean Patent Application No. 10-2013-7017492 (partial English translation).
Notification of Reasons for Rejection dated Nov. 4, 2016, issued in corresponding Japanese Application No. 2012-547938 (with partial English translation).
Tsuchiyama et al., "Efficacy of galectins in the amelioration of nephrotoxic serum nephritis in Wistar Kyoto rats", Kidney International, 2000, vol. 58, pp. 1941-1952.

\* cited by examiner

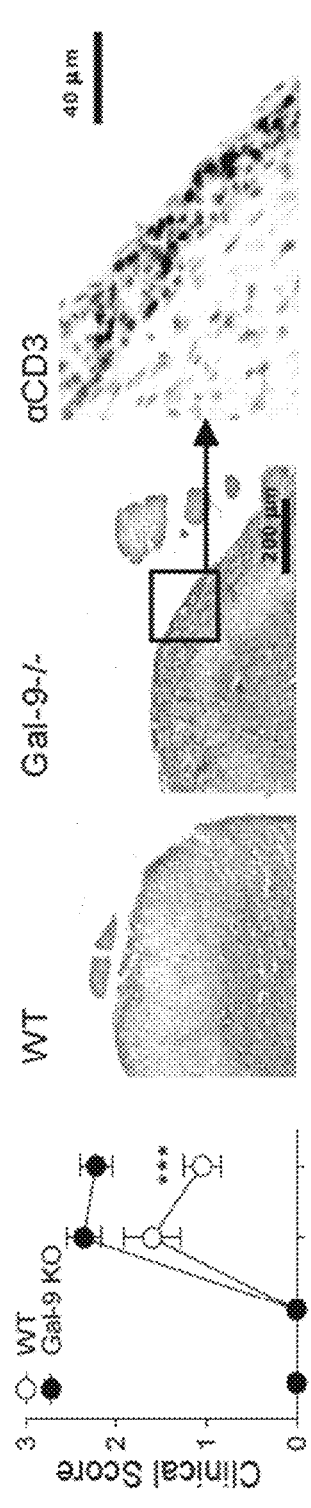
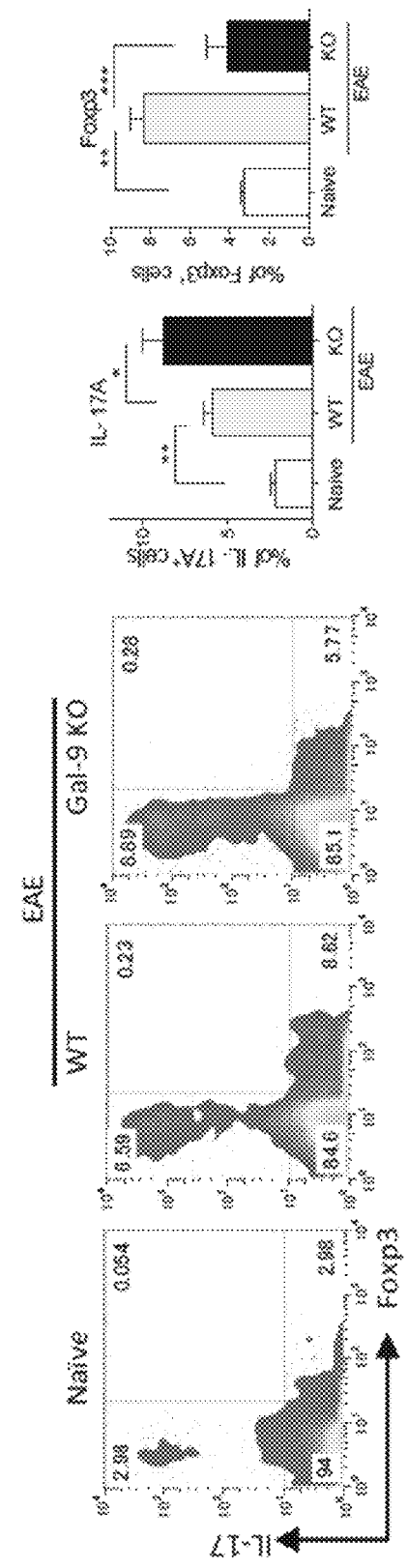
FIG. 3A
FIG. 3B
FIG. 3C

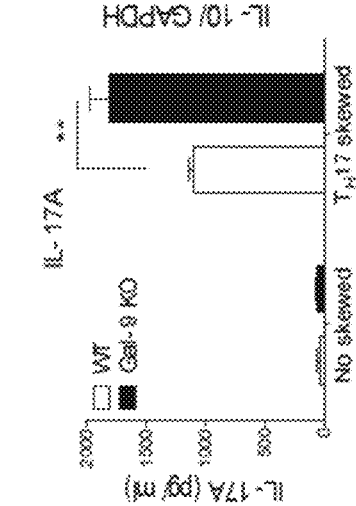
FIG. 3D
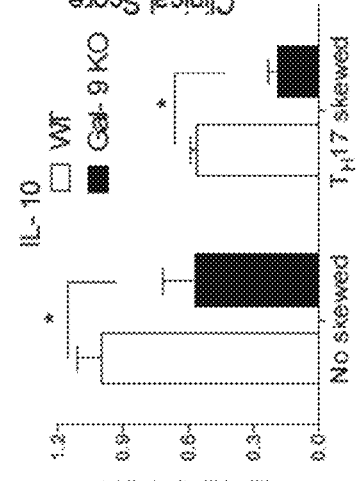
FIG. 3E
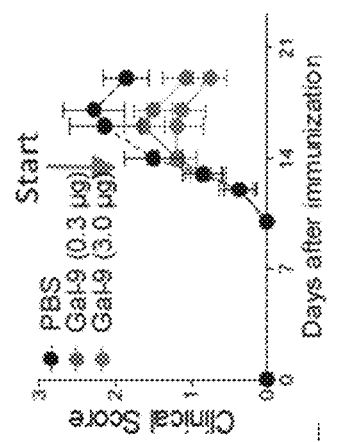
FIG. 3F
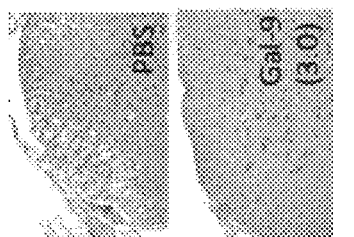

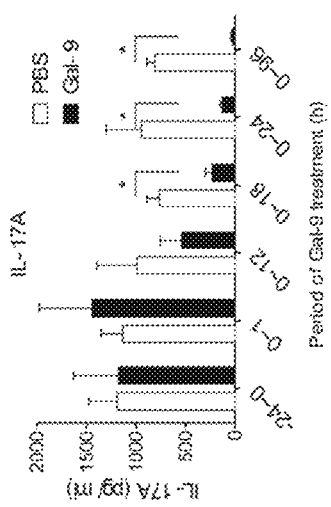
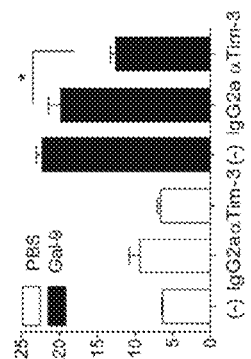
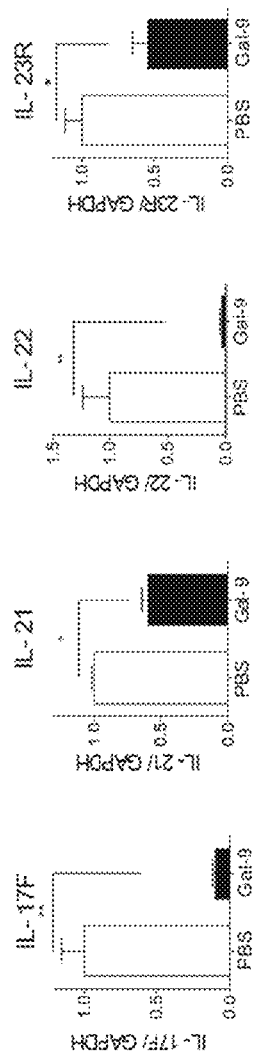
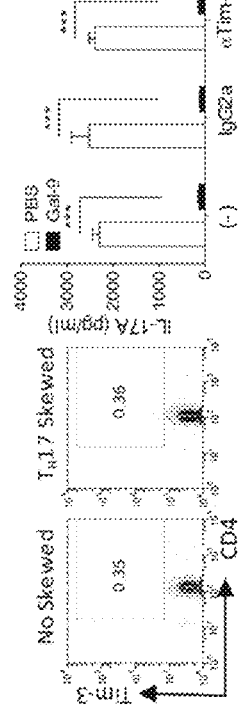
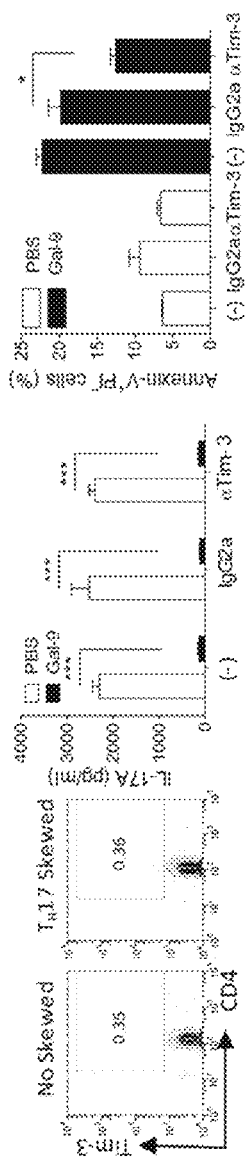
FIG. 4A
FIG. 4B
FIG. 4C
FIG. 4D

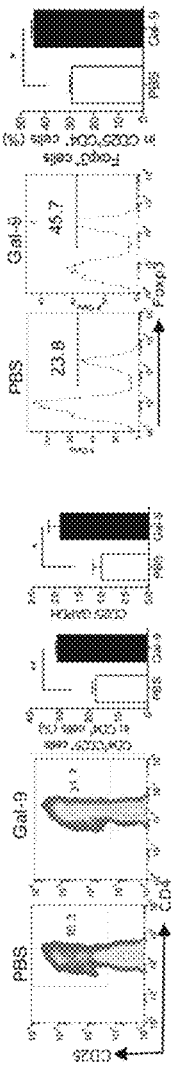
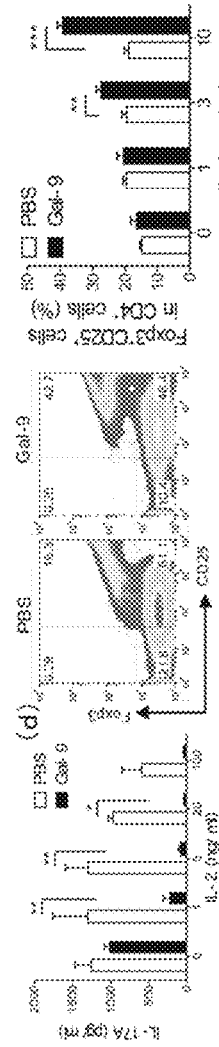
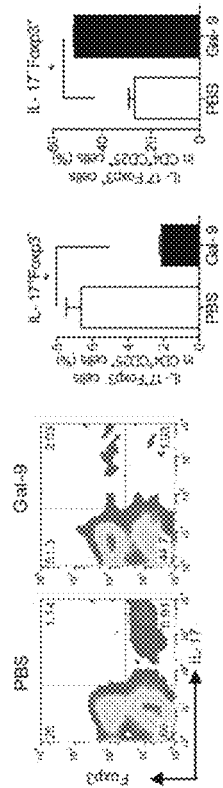
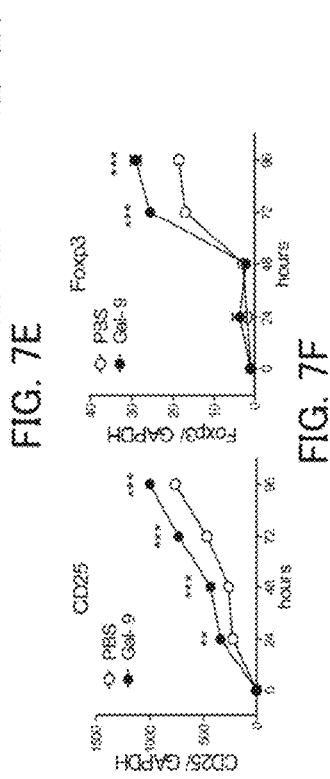
FIG. 7A  FIG. 7B  FIG. 7C  FIG. 7D  FIG. 7E  FIG. 7F

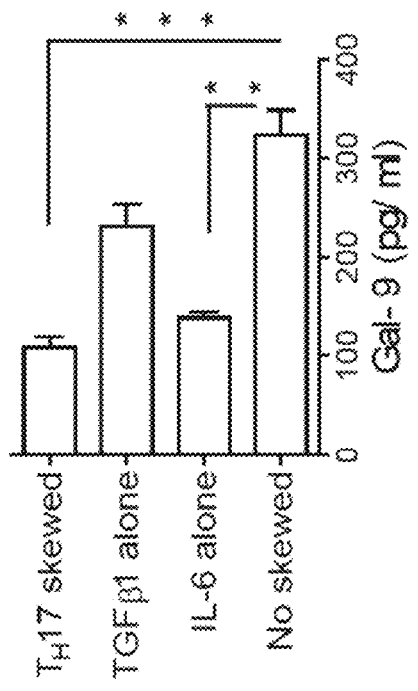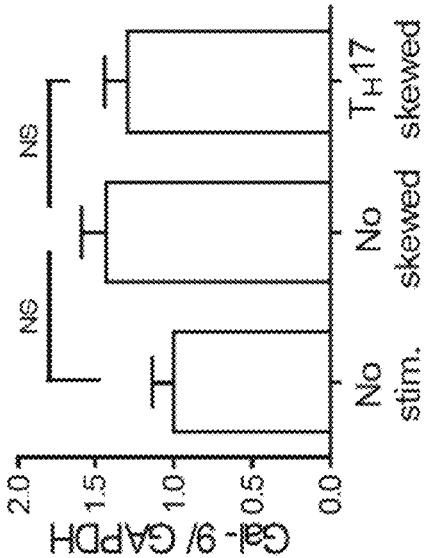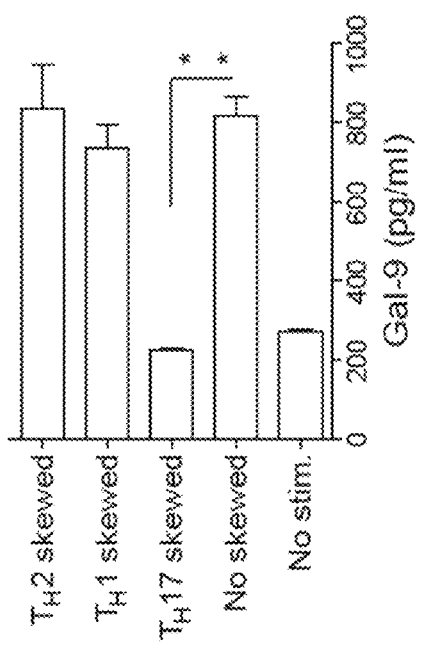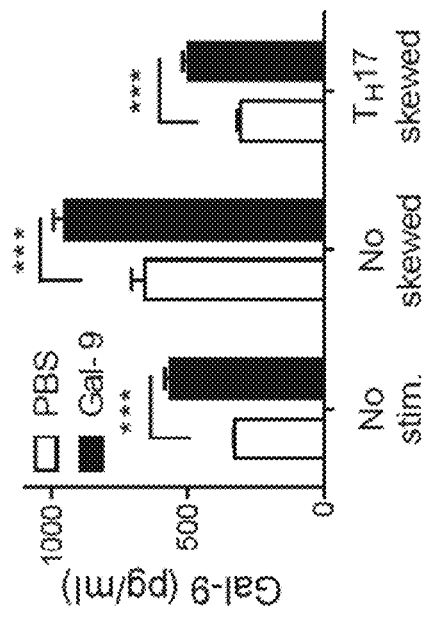
FIG. 8A
FIG. 8B
FIG. 8C
FIG. 8D

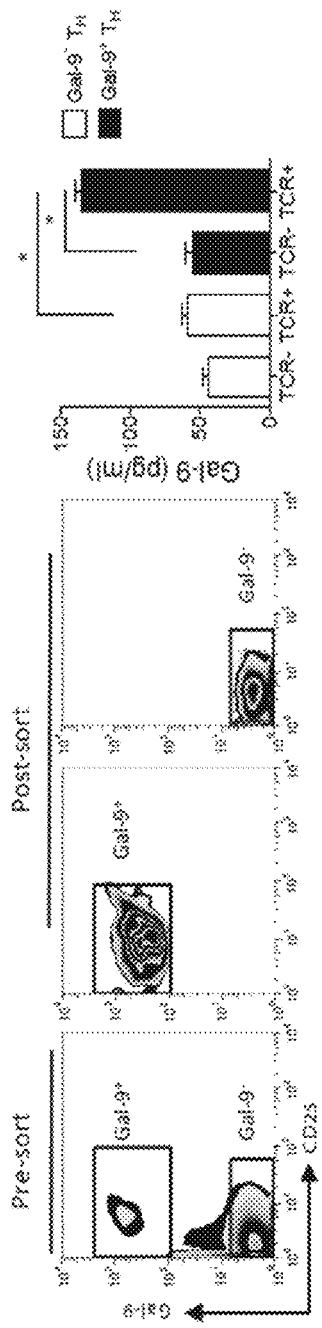
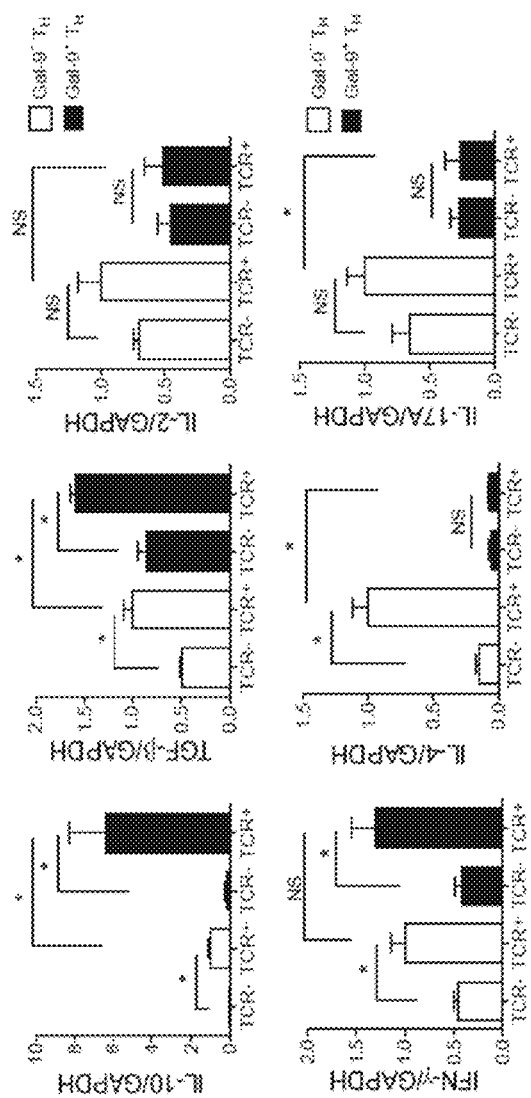
FIG. 9A
FIG. 9B

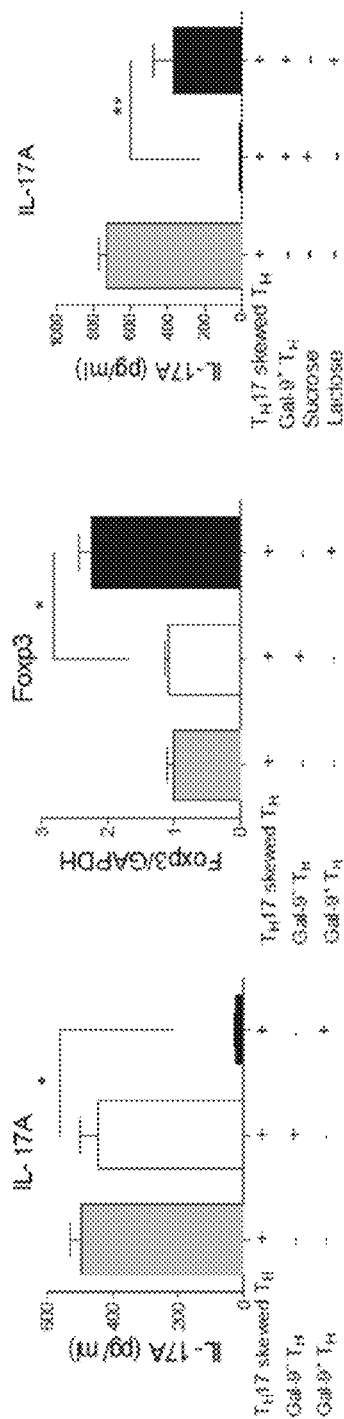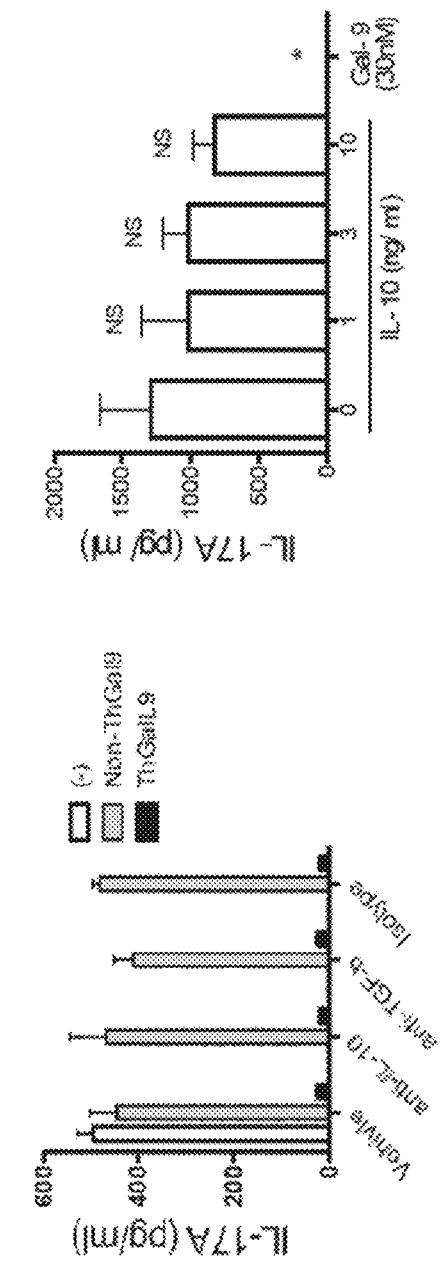
FIG. 9C  FIG. 9D  FIG. 9E  FIG. 9F

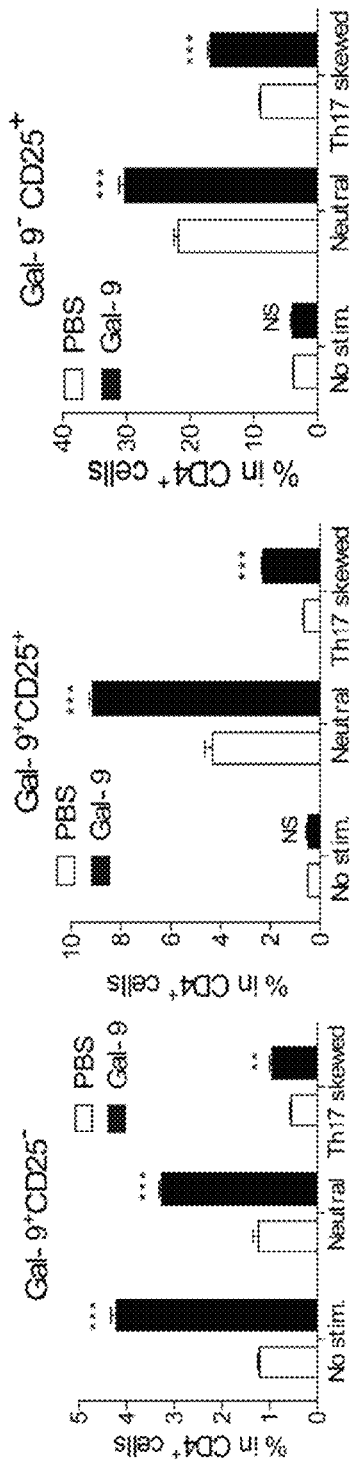
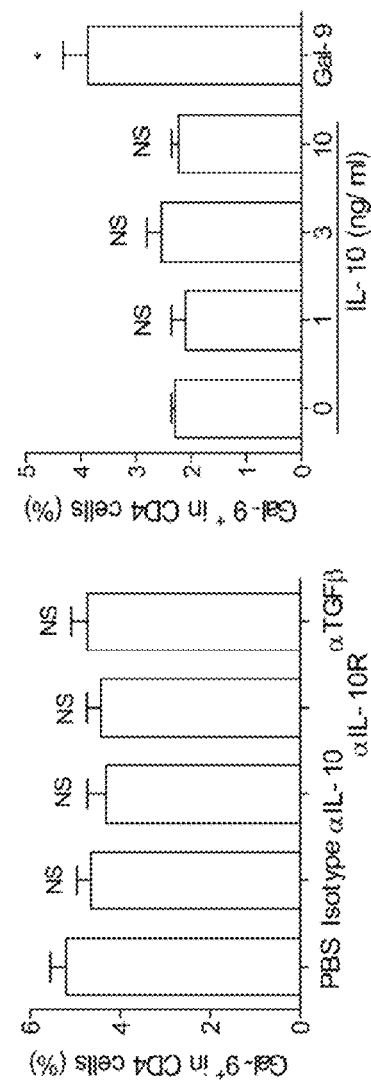
FIG. 11A
FIG. 11B
FIG. 11C

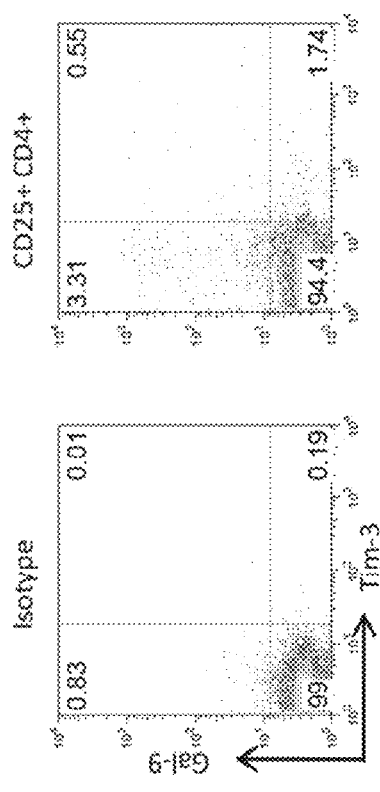
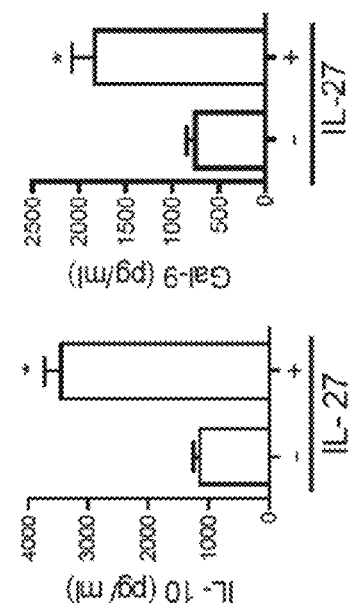
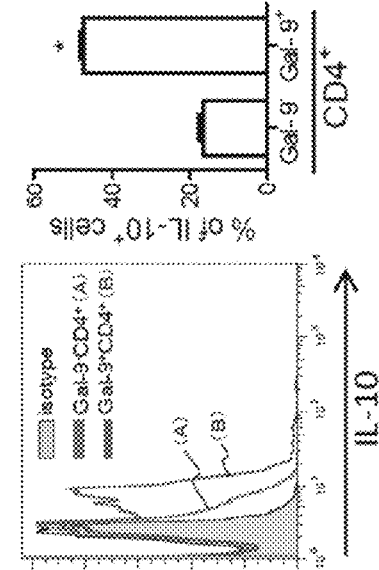
FIG. 12C
FIG. 12D
FIG. 12E
FIG. 12F

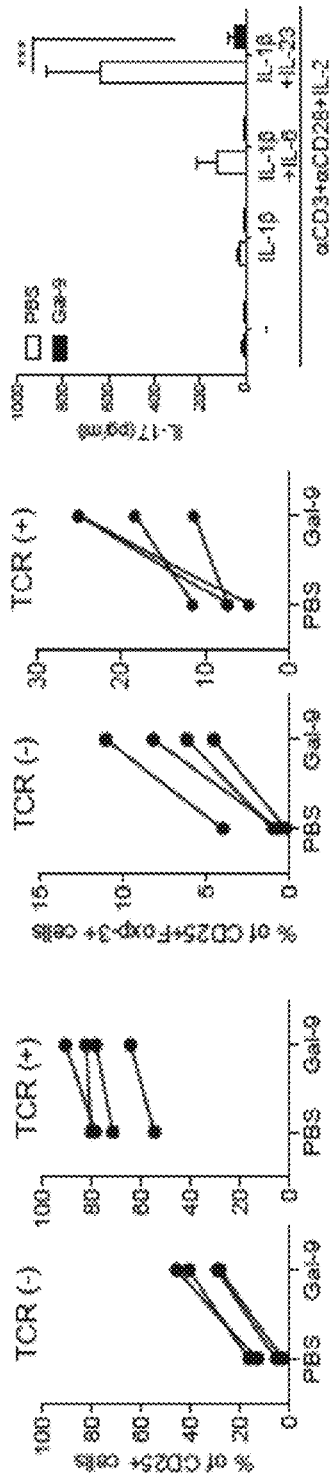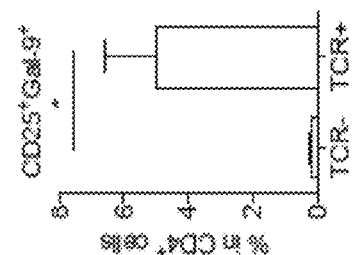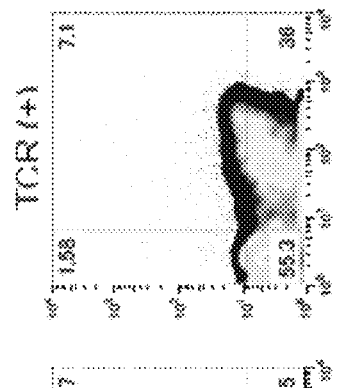
FIG. 14A  FIG. 14B  FIG. 14C  FIG. 14D

M: molecular-weight marker

1: E. coli lysate (before expression induction)

2: E. coli lysate (after expression induction)

3: E. coli extract

4: lactose column non-adsorbed fraction of E. coli extract

5: lactose column eluted fraction purified G9NC(null)

METHOD FOR INCREASING THE PROPORTION OF ANIMAL CELLS SECRETING GALECTIN-9

TECHNICAL FIELD

The present invention relates to galectin-9-secreting cell, a method for producing the cell, and use of the cell. For example, the present invention relates to a CD4 T cell that secretes galectin-9 and techniques applying the CD4 T cell.

BACKGROUND ART

Galectin-9 (Gal-9) is a member of the galectin family, and exhibits physiological activity upon binding to β galactoside of N- or O-glycan (Non-Patent Document 1). Galectin-9 was first discovered and identified as a T cell apoptosis-inducing factor (Non-Patent Document 2) and an eosinophil chemotactic factor (Non-Patent Document 3). From then on, a wide variety of activities of galectin-9 have been reported up to the present. Galectin-9 acts on T cells in the following manner: galectin-9 binds to Tim-3 to induce apoptosis of Tim-3 positive $T_H1$ cells, thereby settling down excess $T_H1$ reactions to inhibit autoimmune inflammation (Non-Patent Document 4). A $T_H17$ cell is considered to be a cause or one of exacerbating factors of various intractable diseases such as autoimmune diseases, allergies, and cancers, and this cell also expresses Tim-3 (Non-Patent Documents 5 to 6). Administration of galectin-9 decreases $T_H17$ cells, and increases inflammation inhibitory Treg cells (Non-Patent Document 7). At present, involvement of Tim-3 in this decrease in $T_H17$ cells and the mechanism by which such decrease occurs are unknown.

As actions of galectin-9 on cells other than T cells, the following actions are known in addition to the above-described eosinophilotactic activity: induction of CD11bLy-6C monocytic myeloid-derived suppressor cells (Non-Patent Document 8); induction of CD11bLy-6G neutrophilic myeloid-derived suppressor cells (Non-Patent Documents 9 to 10); induction of plasmacytoid dendritic cells (Non-Patent Document 11); and inhibition of degranulation from mast cells (Non-Patent Document 12). Many of previous reports focus on the action of galectin-9 for inhibiting exaggerated immunoreactions. However, in some situations, galectin-9 enhances immunity. Galectin-9 binds to Tim-3 on monocytes and dendritic cells to activate these cells, thereby promoting the production of inflammatory cytokines (Non-Patent Document 13). Also, when galectin-9 interacts with Tim-3 in macrophages, immunity for eliminating tubercle bacilli is enhanced (Non-Patent Document 14). That is to say, galectin-9 can modulate immunity bidirectionally.

CITATION LIST

Patent Document(s)

Patent Document 1: WO 2005/09306

Non-Patent Document(s)

Non-Patent Document 1: Hirabayashi, J. et al. Oligosaccharide specificity of galectins: a search by frontal affinity chromatography. Biochim Biophys Acta, 1572, 232-254 (2002)

Non-Patent Document 2: Wada, J., Ota, K., Kumar, A., Wallner, E. I. & Kanwar, Y. S. Developmental regulation, expression, and apoptotic potential of galectin-9, a β-galactoside binding lectin. J Clin Invest, 99, 2452-2461 (1997)

Non-Patent Document 3: Matsumoto, R. et al. Human ecalectin, a variant of human galectin-9, is a novel eosinophil chemoattractant produced by T lymphocytes. J Biol Chem, 273, 16976-16984 (1998)

Non-Patent Document 4: Zhu, C. et al. The Tim-3 ligand galectin-9 negatively regulates T helper type 1 immunity. Nat Immunol, 6, 1245-1252 (2005)

Non-Patent Document 5: Chen, Y. et al. Anti-IL-23 therapy inhibits multiple inflammatory pathways and ameliorates autoimmune encephalomyelitis. J Clin Invest, 116, 1317-1326 (2006)

Non-Patent Document 6: Nakae, S., Iwakura, Y., Suto, H. & Galli, S. J. Phenotypic differences between Th1 and Th17 cells and negative regulation of Th1 cell differentiation by IL-17. J Leukoc Biol, 81, 1258-1268 (2007)

Non-Patent Document 7: Seki, M. et al. Galectin-9 suppresses the generation of Th17, promotes the induction of regulatory T cells, and regulates experimental autoimmune arthritis. Clin Immunol, 127, 78-88 (2008)

Non-Patent Document 8: Arikawa, T. et al. Galectin-9 expands immunosuppressive macrophages to ameliorate T-cell-mediated lung inflammation. Eur J Immunol, 40, 548-558 (2010)

Non-Patent Document 9: Tsuboi, Y. et al. Galectin-9 protects mice from the Shwartzman reaction by attracting prostaglandin E2-producing polymorphonuclear leukocytes. Clin Immunol, 124, 221-233 (2007)

Non-Patent Document 10: Dardalhon, V. et al. Tim-3/galectin-9 pathway: regulation of Th1 immunity through promotion of CD11b+Ly-6G+ myeloid cells. J Immunol, 185, 1383-1392 (2010)

Non-Patent Document 11: Nobumoto, A. et al. Galectin-9 expands unique macrophages exhibiting plasmacytoid dendritic cell-like phenotypes that activate NK cells in tumor-bearing mice. Clin Immunol, 130, 322-330 (2009)

Non-Patent Document 12: Niki, T. et al. Galectin-9 is a high affinity IgE-binding lectin with anti-allergic effect by blocking IgE-antigen complex formation. J Biol Chem, 284, 32344-32352 (2009)

Non-Patent Document 13: Anderson, A. C. et al. Promotion of tissue inflammation by the immune receptor Tim-3 expressed on innate immune cells. Science, 318, 1141-1143 (2007)

Non-Patent Document 14: Jayaraman, P. Tim3 binding to galectin-9 stimulates antimicrobial immunity. J Exp Med, 207, 2343-2354 (2010)

Non-Patent Document 15: Katoh, S. et al. Galectin-9 inhibits CD44-hyaluronan interaction and suppresses a murine model of allergic asthma. Am J Respir Crit Care Med, 176, 27-35 (2007)

Non-Patent Document 16: Nobumoto, A. et al. Galectin-9 suppresses tumor metastasis by blocking adhesion to endothelium and extracellular matrices. Glycobiology, 18, 735-744 (2008)

Non-Patent Document 17: Mishra, R. et al. Galectin-9 trafficking regulates apical-basal polarity in Madin-Darby canine kidney epithelial cells. Proc Natl Acad Sci USA, 107, 17633-17638 (2010)

Non-Patent Document 18: Tanikawa, R. et al. Galectin-9 induces osteoblast differentiation through the CD44/Smad signaling pathway. Biochem Biophys Res Commun 394, 317-322 (2010)

Non-Patent Document 19: Chabot, S. et al. Regulation of galectin-9 expression and release in Jurkat T cell line cells. Glycobiology, 12, 111-118 (2002)

Non-Patent Document 20: Fujio, K., Okamura, T. & Yamamoto, K. The Family of IL-10-secreting CD4+ T cells. Adv Immunol, 105, 99-130 (2010)

Non-Patent Document 21: Ochi, H. et al. Oral CD3-specific antibody suppresses autoimmune encephalomyelitis by inducing CD4+ CD25–LAP+ T cells. Nat Med, 12, 627-635 (2006)

Non-Patent Document 22: Okamura, T. et al. CD4+ CD25–LAG3+ regulatory T cells controlled by the transcription factor Egr-2. Proc Natl Acad Sci USA, 106, 13974-13979 (2009)

Non-Patent Document 23: Wakkach, A. et al. Characterization of dendritic cells that induce tolerance and T regulatory 1 cell differentiation in vivo. Immunity, 18, 605-617 (2003)

Non-Patent Document 24: Jangpatarapongsa, K. et al. *Plasmodium vivax* parasites alter the balance of myeloid and plasmacytoid dendritic cells and the induction of regulatory T cells. Eur J Immunol, 38, 2697-2705 (2008)

Non-Patent Document 25: Kavousanaki, M., Makrigiannakis, A., Boumpas, D. & Verginis, P. Novel role of plasmacytoid dendritic cells in humans: induction of interleukin-10-producing Treg cells by plasmacytoid dendritic cells in patients with rheumatoid arthritis responding to therapy. Arthritis Rheum, 62, 53-63 (2010)

Non-Patent Document 26: Awasthi, A. et al. A dominant function for interleukin 27 in generating interleukin 10-producing anti-inflammatory T cells. Nat Immunol, 8, 1380-1389 (2007)

Non-Patent Document 27: Stumhofer, J. S. et al. Interleukins 27 and 6 induce STAT3-mediated T cell production of interleukin 10. Nat Immunol, 8, 1363-1371 (2007)

Non-Patent Document 28: Fitzgerald, D. C. et al. Suppression of autoimmune inflammation of the central nervous system by interleukin 10 secreted by interleukin 27-stimulated T cells. Nat Immunol, 8, 1372-1379 (2007)

Non-Patent Document 29: Barrat, F. J. et al. In vitro generation of interleukin 10-producing regulatory CD4(+) T cells is induced by immunosuppressive drugs and inhibited by T helper type 1 (Th1)- and Th2-inducing cytokines. J Exp Med, 195, 603-616 (2002)

Non-Patent Document 30: Uhlig, H. H. et al. Characterization of Foxp3+CD4+CD25+ and IL-10-secreting CD4+ CD25+ T cells during cure of colitis. J Immunol, 177, 5852-5860 (2006)

Non-Patent Document 31: Maynard, C. L. et al. Regulatory T cells expressing interleukin 10 develop from Foxp3+ and Foxp3– precursor cells in the absence of interleukin 10. Nat Immunol, 8, 931-941 (2007)

Non-Patent Document 32: Nagahara, K. et al. Galectin-9 increases Tim-3+ dendritic cells and CD8+ T cells and enhances antitumor immunity via galectin-9-Tim-3 interactions. J Immunol, 181, 7660-7669 (2008)

Non-Patent Document 33: Nishi, N. et al. Development of highly stabilized galectins: truncation of the linker peptide confers protease-resistance on tandem-repeat type galectins. FEBS Lett, 579, 2058-2064 (2005)

Non-Patent Document 34: Seki, M. et al. Beneficial effect of galectin-9 on rheumatoid arthritis by induction of apoptosis of synovial fibroblasts. Arthritis Rheum, 56, 3968-3976 (2007)

Non-Patent Document 35: Wilson, N. J. et al. Development, cytokine profile and function of human interleukin 17-producing helper T cells. Nat Immunol, 8, 950-957 (2007)

Non-Patent Document 36: Oomizu, S. et al. Oral administration of pulverized Konjac glucomannan prevents the increase of plasma immunoglobulin E and immunoglobulin G levels induced by the injection of syngeneic keratinocyte extracts in BALB/c mice. Clin. Exp. Allergy, 36, 102-110 (2006)

Non-Patent Document 37: Lu, L. H. et al. Characterization of galectin-9-induced death of Jurkat T cells. J Biochem, 141, 157-172 (2007)

Non-Patent Document 38: Park, H. et al. A distinct lineage of CD4 T cells regulates tissue inflammation by producing interleukin 17. Nat Immunol, 6, 1133-1141 (2005)

Non-Patent Document 39: Laurence, A. et al. Interleukin-2 signaling via STAT5 constrains T helper 17 cell generation. Immunity, 26, 371-381 (2007)

Non-Patent Document 40: Mills, K. H. Induction, function and regulation of IL-17-producing T cells. Eur J Immunol, 38, 2636-2649 (2008)

Non-Patent Document 41: Brun, V., Bastian, H., Neveu, V. & Foussat, A. Clinical grade production of IL-10 producing regulatory Tr1 lymphocytes for cell therapy of chronic inflammatory diseases. Int Immunopharmacol, 9, 609-613 (2009)

Non-Patent Document 42: Levings, M. K. et al. Differentiation of Tr1 cells by immature dendritic cells requires IL-10 but not CD25+ CD4+ Tr cells. Blood, 105, 1162-1169 (2005)

Non-Patent Document 43: Roncarolo, M. G. & Gregori, S. Is FOXP3 a bona fide marker for human regulatory T cells? Eur J Immunol, 38, 925-927 (2008)

Non-Patent Document 44: Kojima, K. et al. Galectin-9 attenuates acute lung injury by expanding CD14-plasmacytoid dendritic cell-like macrophages. Am J Respir Crit. Care Med, 184, 328-339 (2011)

BRIEF SUMMARY OF THE INVENTION

Problem to be Solved by the Invention

Clarification of the above-described galectin-9 activities was mostly achieved by administering or adding recombinant proteins. For example, administration of galectin-9 exhibits a therapeutic effect in mouse collagen-induced arthritis, where galectin-9 inhibits the decrease in Tim-3 positive T cells, the increase in Treg cells, and the production of inflammatory cytokines such as IFN-γ and IL-17 (Non-Patent Document 7). It is noteworthy that galectin-9 knockout mice are highly sensitive to rheumatoid arthritis-inducing stimulation, and in the galectin-9 knockout mice, Tim-3 positive CD4 T cells ($T_H1$ and $T_H17$) are increased and Treg cells are decreased as compared with those in wild-type mice (Non-Patent Document 7). These properties are consistent with the effects of galectin-9 clarified by the administration of recombinant proteins. Accordingly, it is obvious that galectin-9 is secreted as an endogenous immunoregulatory factor and adjusts immune balance. However, a cell that secretes galectin-9 or modulates immunity in vivo has not yet been identified.

Tim-3 is the most extensively studied target of galectin-9. However, all of the wide variety of galectin-9 activities cannot be explained with Tim-3. Indeed, up until the present, CD44 and integrin (which are adhesion factor for activated lymphocytes) and IgE have been identification as targets of galectin-9, and exaggerated immunoreactions by allergies and metastasis of cancer cells are inhibited via these targets (Non-Patent Documents 12, 15 to 16). It can be easily predicted that more targets of galectin-9 would be found in the future as the research advances. Exhibiting a variety of activities through interactions with a plurality of targets as described above is a common property among many lectins. By the way, the above-described targets of galectin-9 are all present on cell membranes. Thus, needless to say, the functions of galectin-9 is exhibited after it is secreted out of the cell and binds to these targets.

However, galectin-9 has no signal peptide and basically is located in the cytoplasm, and its roles in the cytoplasm or nucleus also have been reported (Non-Patent Documents 17 to 18). However, considering the presence of the targets on the cell membrane and the actions of galectin-9 as described above, there must be some galectin-9 secreted out of the cell. Actually, secretion of galectin-9 from a T cell- or mast cell-derived cell line has been reported (Non-Patent Documents 12 and 19). However, the secretion mechanism thereof is totally unknown. Also, since the reported origin of secretion is the cell line, there is no guarantee that cells of the same line similarly secrete galectin-9 in vivo. Most of all, the fact that cells expressing galectin-9 do not necessarily secrete the galectin-9 makes the identification of galectin-9 secreting cells particularly difficult.

Galectin-9 is an important immunoregulatory factor. If galectin-9 secreting cells can be identified, they are expected to be useful as indicators to examine immune balance, so that, for example, they can serve as surrogate markers for diagnosing various immune diseases or determining a therapeutic effect on the same. It is also expected that the galectin-9 secreting cells can be used in cell therapy when used in combination with a technique for purifying the cells, and there is a possibility that the cells can be applied to treatment of intractable diseases such as autoimmune diseases, allergies, and cancers.

As described above, although galectin-9 have a wide variety of immune regulatory activities, much about the details of their action mechanisms remains unknown. Also, cells etc. that secrete galectin-9 or regulate immunoreactions in vivo have not yet been identified. Clarification of the details of immune regulation, e.g., the details of differentiation control of $T_H17$ and Treg cells, by galectin-9, or identification of cells that can exhibit physiological activity based on galectin-9, such as cells that secrete galectin-9 or regulate immunoreactions in vivo, has been desired.

With the foregoing in mind, it is an object of the present invention to provide a cell that can exhibit physiological activity based on galectin-9, a method for producing the cell, and use of the cell.

Means for Solving Problem

In order to achieve the above object, the present invention provides a cell that contains galectin-9, characterized in that the galectin-9 is expressed on a cell surface.

The present invention provides, as a first production method of the cell according to the present invention, a method for producing the cell of the present invention, including: administering galectin-9 to an animal, thus inducing galectin-9 expression on a cell surface of at least one cell in the animal.

The present invention provides, as a second production method of the cell according to the present invention, a method for producing the cell of the present invention, including: culturing one or more cells of an animal in the presence of galectin-9, thus inducing galectin-9 expression on a cell surface of at least one of the cells.

The present invention also provides a pharmaceutical agent containing: at least one selected from the group consisting of: the cell of the present invention; homogenates of the cell; and extracts of the cell.

The present invention also provides a method for diagnosing the presence or absence of galectin-9 or a galectin-9-binding substance in a test cell using at least one selected from the group consisting of: the cell of the present invention; homogenates of the cell; and extracts of the cell.

The present invention also provides a method for treating a disease of an animal or reducing a symptom caused by the disease, including the step of administering to the animal at least one selected from the group consisting of the cell of the present invention; homogenates of the cell; and extracts of the cell.

The present invention also provides a method for regulating immunity of an animal, including the step of: administering the cell of the present invention to the animal.

The present invention also provides a method for detecting the cell of the present invention, including the step of: detecting the galectin-9 expressed on the cell surface of the cell as a marker.

The present invention also provides a method for diagnosing a disease of an animal or a symptom caused by the disease, including the step of: in a tissue of the animal containing or not containing the cell of the present invention, detecting the cell of the present invention qualitatively or quantitatively by the cell detection method of the present invention.

The present invention also provides a method for determining a therapeutic effect on a disease of an animal, including the steps of: treating the disease of the animal; diagnosing the disease or a symptom caused by the disease by the diagnostic method of the present invention before and after the treatment; and comparing diagnostic results obtained before and after the treatment.

The present invention also provides a cell separation method including the steps of: in a tissue of an animal containing the cell of the present invention, detecting the cell by the cell detection method of the present invention; and separating the detected cell from other cells in the tissue of the animal.

Effects of the Invention

As described above, according to the present invention, it is possible to provide a cell that can exhibit physiological activity based on galectin-9, a method for producing the cell, and use of the cell.

BRIEF DESCRIPTION OF DRAWINGS

In FIGS. 1B and 1C, the horizontal axis indicates the number of days elapsed after the first immunization, and the vertical axis indicates the increase rate (%) of the volume of paws. The plot indicated with "Vehicle" shows the results obtained in a control experiment where only a solvent was used (no administration of stabilized human galectin-9), and the plot indicated with "non-arthritis" shows the measurement results regarding arthritis-free rats.

FIG. 2 shows the results obtained when Lewis rats (♀, 6- to 7-week old) were given single subcutaneous administration of stabilized human galectin-9 at each dose indicated in FIG. 2, and the stabilized human galectin-9 in plasma was measured by specific ELISA. The horizontal axis indicates the elapsed time, and the vertical axis indicates the concentration of the stabilized human galectin-9 in plasma.

FIG. 3 shows the effect of galectin-9 on mouse MOG-induced experimental allergic encephalitis (EAE) in still another example of the present invention. (A) FIG. 3A is a graph showing EAE clinical scores over time in female C57BL/6J mice (WT) and galectin-9 knockout mice (Gal-9 KO) of the same line. The horizontal axis indicates the time elapsed after immunization, and the vertical axis indicates the clinical score. (B) FIG. 3B shows tissue micrographs of the spinal cords of the mice (WT and Gal-9 KO (Gal-9$^{-/-}$)) stained with hematoxylin-eosin and immunostained with an anti-CD3 antibody at week 20 after the immunization. (C) Inguinal lymph node cells were prepared from EAE-immunized wild-type mice (WT) and EAE-immunized galectin-9 knockout mice (Gal-9 KO) at week 20 after the immunization and non-sensitized mice (naïve) of the same week old, respectively. FIG. 3C shows the results of staining the cells with CD4, CD25, IL-17, and Foxp3 antibodies. In FIG. 3C, "Naïve" indicates naïve T cells. (D) CD4$^+$CD62L$^+$ naïve T cells were prepared from spleen cells of wild-type mice (WT) and galectin-9 knockout mice (Gal-9 KO). The CD4$^+$CD62L$^+$ naïve T cells were cultured in a 96-well plate coated with an anti-CD3 antibody in the presence of an anti-CD28 antibody (No skewed), or, in addition to the anti-CD28 antibody, further in the presence of human TGF-β 1, mouse IL-2, and mouse IL-6 to induce $T_H17$ cell differentiation ($T_H17$ skewed). The results thereof are shown in FIG. 3D. More specifically, FIG. 3D is a graph showing the results of quantifying the concentration of IL-17A in each culture supernatant obtained after 96 hours of culture by ELISA. (E) FIG. 3E is a graph showing the results of quantifying the amount of IL-10 mRNA in cells having remained after extracting the culture supernatant in the above (D) by real-time RT-PCR. (F) The onset of EAE was induced in female C57BL/6J mice using the system described in the above (A). Stabilized human galectin-9 was administered subcutaneously to the mice (PBS was administered to a control group) on day 14 and day 16 after the immunization, and clinical scores were recorded until day 19 after the immunization. FIG. 3F shows the results of staining spinal cords of the mice with hematoxylin-eosin after the above-described process. In the graph shown in FIG. 3F, the horizontal axis indicates the time elapsed after the immunization, and the vertical axis indicates the clinical score.

FIG. 4 shows graphs showing the results of examining whether or not inhibition of $T_H17$ cell differentiation by galectin-9 depends on a Tim3/Gal-9 interaction in still another example of the present invention. (A) Naïve T cells were subjected to $T_H17$ cell differentiation-inducing stimulation for 96 hours by the method of FIG. 3D with the stabilized human galectin-9 (30 nM) being added for each period indicated in FIG. 4A. FIG. 4A shows the results quantifying the concentration of IL-17A in the culture supernatant by ELISA. The horizontal axis indicates the period of the galectin-9 treatment, and the vertical axis indicates the concentration of IL-17A. (B) Naïve T cells were subjected to $T_H17$ cell differentiation-inducing stimulation for 24 hours in the presence of the stabilized human galectin-9. FIG. 4B shows graphs showing the results of quantifying the mRNA expressions of IL-17F, IL-21, IL-22 and IL23R by real-time RT-PCR. (C) Naïve T cells were cultured for 24 hours under $T_H17$ differentiation-inducing stimulation ($T_H17$ skewed) or the condition excluding TGF-β1 and IL-6 from the same differentiation inducing-stimulation (No skewed). FIG. 4C shows graphs showing the results of analyzing CD4$^+$Tim-3$^+$ cells obtained under the respective conditions by flow cytometry (two graphs the left); and a graph showing the result of conducting an assay on inhibition of $T_H17$ differentiation induction by stabilized human galectin-9 in the presence of a Tim-3 neutralizing antibody (the right graph). (D) Naïve T cells were cultured for 96 hours under $T_H17$ differentiation-inducing stimulation, and stabilized human galectin-9 was added to the cells. FIG. 4D is a graph showing the results of measuring Tim-3 positive cells ($T_H17$ cells) having undergone apoptosis by flow cytometry.

FIG. 5 show graphs showing the results of examining which of N-linked carbohydrate chain and O-linked carbohydrate chain is involved in inhibition of $T_H17$ differentiation induction by galectin-9 in still another example of the present invention. (A)

FIG. 7 shows the results of examining whether or not the adjustment of $T_H17$/Treg balance by galectin-9 depends on IL-2 in still another example of the present invention. (A) Stabilized human galectin-9 (or PBS as a control) was added to naïve T cells, and the naïve T cells were cultured under a $T_H17$ differentiation-inducing condition. FIG. 7A shows the results of measuring the proportion of CD4$^+$CD25$^+$ cells in the cultured cells by flow cytometry. (B) FIG. 7B shows the proportion of CD4$^+$CD25$^+$Foxp3$^+$ cells in the cells obtained in the above (A). (C) Stabilized human galectin-9 (control: PBS) and IL-2 at each concentration indicated in FIG. 7C were added to naïve T cells, and the naïve T cells were cultured under a $T_H17$ differentiation-inducing condition.

FIG. 7C shows the results of quantifying the concentration of IL-17A in each culture supernatants by ELISA. (D) FIG. 7D shows graphs showing the results of measuring the proportion of Treg cells (CD4$^+$CD25$^+$Foxp3$^+$ cells) in the cells cultured under the condition described in the above (C) by flow cytometry. (E) Stabilized human galectin-9 (control: PBS) was added to naïve T cells. The naïve T cells were cultured under a T$_H$17 differentiation-inducing condition, and thereafter, cultured further in the presence of PMA, ionomycin, and brefeldin A. FIG. 7E shows the results of measuring the proportions of IL-17$^+$Foxp3$^-$ cells and IL-17-Foxp3$^+$ cells in the CD4 positive cells by flow cytometry. (F) Naïve T cells were cultured under the condition described in the above (E). FIG. 7F shows graphs showing the results of quantifying the mRNA expressions of CD25 and Foxp3 at each given time point by real-time RT-PCR. The horizontal axis indicates the elapsed time, and the vertical axis indicates the expression level.

FIG. 8 shows the results of examining (identifying) CD4 positive T cells (T$_H$GAL9) expressing galectin-9 on cell surfaces in still another example of the present invention. (A) Naïve T cells were cultured under the respective conditions described above in connection with FIG. 6A or without stimulation (No stim). FIG. 8A shows the results of quantifying the concentration of galectin-9 in each culture supernatant by ELISA. The condition using TCR stimulation only is indicated as "No skewed". (B) Naïve T cells were cultured under the following respective conditions: a T$_H$17 differentiation inducing-condition (T$_H$17 skewed; IL-2, TGF-β1, and IL-6 stimulation in addition to TCR stimulation); the condition excluding IL-6 from the T$_H$17 differentiation inducing-condition (TGF-β1 alone); the condition excluding TGF-β1 from the T$_H$17 differentiation inducing-condition (IL-6 alone); or TCR stimulation only (No skewed). FIG. 8B shows the results of quantifying galectin-9 in each supernatant after the culture by ELISA. (C) Stabilized human galectin-9 (or PBS as a control) was added to naïve T cells, and the naïve T cells were cultured under the following respective conditions: without stimulation (No stim); TCR stimulation only (No skewed); and the T$_H$17 differentiation-inducing stimulation. FIG. 8C shows the results of quantifying galectin-9 in each supernatant after the culture by ELISA. (D) FIG. 8D shows the results of quantifying the amount of galectin-9 mRNA in the cells described in the above (C) by real-time RT-PCR. (E)

FIG. 9 shows the results of examining the functions of T$_H$GAL9 in still another example of the present invention. (A) FIG. 9A shows the results obtained when naïve T cells prepared from spleen cells of mice (the graph on the left) were sorted into cell surface galectin-9 positive cells (T$_H$GAL9 cells: Gal-9$^+$ T$_H$) and cell surface galectin-9 negative cells (non-T$_H$GAL9: Gal-9$^-$ T$_H$) (two graphs in the middle), each of these cell groups was subjected to TCR stimulation, and then galectin-9 secreted in the culture supernatant was quantified by ELISA (the graph on the right). (B) FIG. 9B shows the results of examining the mRNA expressions of cytokines in the above-described cells by real-time RT-PCR. (C) Naïve T cells were cultured under T$_H$17 differentiation-inducing stimulation. The cultured cells were then mixed with T$_H$GAL9 cells (Gal-9$^+$ T$_H$) or non-T$_H$GAL9 (Gal-9$^-$ T$_H$) cells at a mixing ratio of 1:1, after which they were co-cultured under TCR stimulation only. FIG. 9C shows: a graph showing the results of quantifying IL-17A in each culture supernatant by ELISA (the left graph); and a graph showing the results of quantifying the mRNA expression of Foxp3 by real-time RT-PCR (the right graph). (D) The above co-culture was carried out in the presence of lactose as a galectin-9 inhibitor (or sucrose as a control). FIG. 9D shows the results of quantifying the concentration of IL-17A in each culture supernatant by ELISA. (E) FIG. 9E shows the results obtained when the co-culture described in the above (C) was carried out in the presence of an IL-10 neutralizing antibody or a TGF-β neutralizing antibody. (F) Naïve T cells were subjected to T$_H$17 differentiation-inducing stimulation in the presence of IL-10 or stabilized human galectin-9 FIG. 9F shows the results of quantifying the concentration of IL-17A in each culture supernatant by ELISA.

FIG. 10 shows graphs showing the results of examining the production of galectin-9, IL-10, and TGF-β1 from CD25$^+$ T$_H$GAL9 in still another example of the present invention. (A) Naïve CD4 T cells were cultured under TCR stimulation, and the cultured cells were sorted into CD25$^+$ T$_H$GAL9, CD25$^+$ non-T$_H$GAL9, and CD25$^-$ non-T$_H$GAL9. Thereafter, each cell group was cultured further under TCR stimulation.

FIG. 11 shows graphs showing the results of examining the induction of T$_H$GAL9 by the addition of stabilized galectin-9 in still another example of the present invention. (A) Stabilized human galectin-9 (or PBS as a control) was added to naïve CD4 T cells. The naïve CD4 T cells were cultured without stimulation (No stim), under TCR stimulation only (Neutral), or under T$_H$17 differentiation-inducing stimulation (Th17 skewed). FIG. 11A shows the results of examining the expressions of cell surface galectin-9 and CD25 after the culture by flow cytometry. (B) Naïve CD4 T cells were subjected to TCR stimulation in the presence of an IL-10 neutralizing antibody, an IL-10R neutralizing antibody, or a TGF-β neutralizing antibody. FIG. 11B shows the results of examining the emergence of T$_H$GAL9 cells by flow cytometry. (C) IL-10 or stabilized human galectin-9 was added to naïve CD4 T cells, and the naïve CD4 T cells were cultured under TCR stimulation. FIG. 11C shows the results of examining the emergence of T$_H$GAL9 cells after the culture by flow cytometry.

FIG. 12 shows the results of examination to verify a high degree of similarity between T$_H$GAL9 and Tr1 in still another example of the present invention. (A) Cell surface galectin-9 in naïve CD4$^+$ T cells was stained, and in addition, the naïve CD4$^+$ T cells also were stained with the respective antibodies against the reported Tr1 cell markers (LAP, NKG2D, LAG-3 and CTLA-4). FIG. 12C shows the results of examining the expressions of cell surface galectin-9, Tim-3, and CD25 in the cells prepared in the above (B) by flow cytometry. (D) Naïve CD4+ T cells were cultured under Tr1 cell differentiation stimulation by the addition of IL-27. Thereafter, the naïve CD4+ T cells were further subjected to stimulation with PMA and ionomycin. FIG. 12D shows the results of quantifying IL-10 in the culture supernatant by ELISA. (E) FIG. 12E shows the results of quantifying galectin-9 in the culture supernatant in the above (D) by ELISA. (F) The treatment with PMA and ionomycin described in the above (D) was carried out in the presence of brefeldin A (10 µg/ml), thus causing IL-10 to accumulate inside the cells. FIG. 12F shows the results of staining galectin-9 on cell surfaces and IL-10 inside the cells and measuring them by flow cytometry.

FIG. 13 shows the results of examining whether cells having Tr1 markers decrease in galectin-9 knockout mice in still another example of the present invention. (A)

FIG. 14 shows the results of examining the effect of galectin-9 on human $T_H17$/Treg differentiation and identifying human $T_HGAL9$ cells in still another example of the present invention. (A) Stabilized human galectin-9 (or PBS as a control) was added to peripheral blood CD4+ T cells collected from four healthy subjects, and the cells were cultured under TCR stimulation or without stimulation. FIG. 14A shows the results of measuring CD25 positive cells by flow cytometry. (B) FIG. 14B shows the results of measuring the proportion of CD25+Foxp3+in the cells described in the above (A) by flow cytometry. (C) Stabilized human galectin-9 (or PBS as a control) was added to human CD4+ T cells, and the human CD4+ T cells were cultured under $T_H17$ cell differentiation-inducing stimulation. FIG. 14C shows the results of quantifying IL-17 in the culture supernatant by ELISA. (D) Human CD4+ T cells were cultured under TCR stimulation or without stimulation. FIG. 14D shows the results obtained when cell surface galectin-9 and CD25 in the cultured cells were stained, and measured by flow cytometry. (E) Human CD4+ T cells were cultured under TCR stimulation, and then, the cultured cells were sorted into cell surface galectin-9 positive cells (CD25+ $T_HGAL9$) and cell surface galectin-9 negative cells (CD25+ non-$T_HGAL9$). Each cell group was further cultured under TCR stimulation.

FIG. 16 shows graphs showing the results of examining the effectiveness of stabilized human galectin-9 in a serious peritonitis model in still another example of the present invention. The onset of peritonitis was induced by cecal ligation and puncture (CLP), and the survival rate over time was examined. (A)

FIG. 17 shows the results of quantifying cytokines in the culture supernatant by ELISA. The vertical axis indicates the concentration of each cytokine.

FIG. 18 shows the results of measuring the expressions of CD3ε, NK1.1, GL-3, and cell surface galectin-9 in the spleen cells by flow cytometry by staining them with the respective antibodies. CD3+NK1.1+: NKT cells, CD3− NK1.1+: NK cells, CD3+GL-3+: γδT cells. $T_HGAL9$ cells were included in the CD3+NK1.1−Gal-9+ and CD3+GL-3− Gal-9+ fractions. In FIG. 18, "Spleen cells from CLP mouse" means "spleen cells taken out from CLP mouse".

As has been reported, administration of stabilized human galectin-9 to cancer-carrying mice enhances the survival rate of the mice. FIG. 19 shows the results of examining the change in immune cells caused at this time and the expression of galectin-9 on cell surfaces of these immune cells in still another example of the present invention. Mouse fibrosarcoma Meth A cells were introduced into the abdominal cavity of each mouse according to the reported method (Non-Patent Document 32). From immediately after the introduction, stabilized human galectin-9 was administered intraperitoneally three times a week (30 µg/mouse). 7 days after the Meth A transplantation, intraperitoneal cells and spleen cells were taken out from the mice, and the cell surface markers indicated in FIG. 19 were stained. FIG. 19 shows the results of measuring the cell surface markers by flow cytometry. (A)

FIG. 20A shows the results of examining the change in urine protein concentration, and FIG. 20B shows the results of examining the change in weight. In FIG. 20A, the horizontal axis indicates the number of weeks elapsed after the administration, and the vertical axis indicates the concentration of urine protein. All data represent the mean values of n=7 to 10 animals at each give time point. Statistical differences were analyzed using the two-way ANOVA, and differences between groups were assessed using the Bonferroni post-test (*P<0.05, P<0.01, *P<0.001). In FIG. 20B, the horizontal axis indicates the number of days elapsed after the administration, and the vertical axis indicates the amount of increase in weight. All data represent the mean values±SEM of n=6 to 8 animals at each give time point. Statistical differences were analyzed using two-way ANOVA, and differences between groups were assessed using the Bonferroni post-test (*P<0.05, P<0.01, *P<0.001).

In FIG. 21A, the horizontal axis indicates the number of weeks elapsed after the administration, and the vertical axis indicates the change in volume of the pedal edema in hind paws. All data represent the mean values±SEM of n=6 to 10 animals at each give time point. Statistical differences were analyzed using two-way ANOVA, and differences between groups were assessed using the Bonferroni post-test (*P<0.05, P<0.01, *P<0.001). In FIG. 21B, the horizontal axis indicates the dose of stabilized human galectin-9, and the vertical axis indicates the hematocrit value at the end of the experiment (at 22 weeks of age). All data represent the mean values±SEM of n=6 to 8 animals at each give time point. Statistical differences were analyzed using two-way ANOVA, and differences between groups were assessed using the Dunnett's multiple comparison test (*P<0.05, P<0.01, *P<0.001).

FIG. 22A shows the concentration of IgM specific to SRBC. FIG. 22B shows the concentration of the total IgM. FIG. 22C shows the concentration of the total IgG. These concentrations were each measured by ELISA specific to the target. (D) Stabilized human galectin-9 or PBS as a control was administered to MRL/MpJUmmCrj-lpr/lpr mice (♀,8-week old) 3 times/week at a dose of 30 µg/mouse, and blood was collected from each mouse on day 7 after the administration. FIG. 22D shows the results of measuring the concentration of anti-double-stranded DNA antibody (typical self-reactive antibody) in serum by a specific ELISA. In FIG. 22, "Days after SRBC injection" means the number of days elapsed after the intraperitoneal administration of SRBC.

FIG. 24 shows the results of examining whether galectin-9 also acts on B cells in still another example of the present invention. SRBC was intraperitoneally administered to C57BL/6J mice (♀) or galectin-9 knockout mice. Immediately after the administration, the mice were given single intraperitoneally administration of stabilized human galectin-9 (30 µg/mouse) or PBS as a control. At each given time point, blood collection and spleen extirpation were performed with respect to three to five mice. FIG. 24 shows the results of examining B cells by flow cytometry shown in FIG. 23. (A) In FIG. 24B, "Day post immunization" means the number of days elapsed after the immunization. (C)

FIG. 25 shows the results of examining whether B cells expressed galectin-9 on cell surfaces in still another example of the present invention. (A) The spleen cells on day 7 after the SRBC administration were separated into germinal center B cells and other B cells according to the flow cytometry shown in FIG. 23.

FIG. 26A shows an example of the dot plot obtained by gating CD4 positive cells based on the expressions of CXCR5 and ICOS, and also shows the cell surface galectin-9 expression in each subset of quadrant obtained based on the expressions of CXCR5 and ICOS. (B) FIG. 26B shows the change in the proportion of each cell population over time. (C) FIG. 26C shows the results of examining whether the proportion of the CD4 positive cells was changed by administration of stabilized human galectin-9. (D) FIG. 26D shows the results demonstrating that the proportion of the cell surface galectin-9 positive cells in each cell population increased after the SRBC administration. (E) FIG. 26E shows the results demonstrating that the expression level of cell surface galectin-9 (MFI) in each cell population increased after the SRBC administration. In FIG. 26E, "Days after SRBC injection" means the number of days elapsed after the intraperitoneal administration of SRBC.

FIG. 29 shows that administration of galectin-9 allowed prolonged survival of LLC cancer-carrying mice, and pDC-like macrophages increased at this time in still another example of the present invention. (A) Cells of a mouse lung cancer-derived tumor cell line LLC were inoculated into abdominal cavities of mice. After the LLC inoculation, 30 μg of stabilized human galectin-9 (or PBS as a control) was administered intraperitoneally to the mice 3 times/week.

FIG. 30 shows that differentiation of CD11c positive cells with M-CSF was promoted by galectin-9 in a test tube in a Tim-3 independent manner in still another example of the present invention. (A) Mouse bone marrow cells were cultured for 7 days in GM-CSF or M-CSF to promote differentiation thereof into dendritic cells, and the expression of CD11c (one of dendritic cell markers) was examined.

(A) The cells cultured for 7 days in the presence of M-CSF or M-CSF and galectin-9 in the experiment described with reference to FIG. 30 were stained with the antibodies against macrophage markers and dendritic cell markers shown in FIG. 31A.

FIG. 33 shows the results of examining the functions of the pDC-like macrophages allowed to exhibit a more mature phenotype by LPS stimulation in still another example of the present invention.
(A) To pDC-like macrophages matured by being subjected to the LPS stimulation by the method of FIG. 32A, the TLR agonists (control; PBS) indicated on the horizontal axis of FIG. 33A were added. The pDC-like macrophages then were cultured for 18 hours.

MODE FOR CARRYING OUT THE INVENTION

Figure 1A:
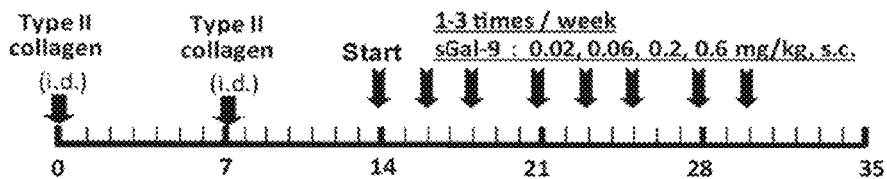
FIG. 1 shows a therapeutic effect of stabilized human galectin-9 in a rat collagen-induced arthritis model in an example of the present invention. As per the schedule shown in FIG. 1A, Lewis rats (♀, 6- to 7-week old) were immunized. From day 14 after the first immunization when the swelling of paws became significant, stabilized human galectin-9 (or PBS as a control) was administered subcutaneously at the dose indicated in FIG. 1A, and the swelling of the paws was monitored over time.
FIG. 1B is a graph showing the results obtained by 3 times/week administration.
FIG. 1C is a graph showing the results obtained by 1 time/week or 2 times/week administration with a dose for each administration being fixed to 0.6 mg/kg.

The present invention will be described more specifically below. It should be noted, however, that the present invention is by no means limited by the following descriptions.

The inventors of the present invention conducted diligent studies, where they focused on clarification of the details of the immune regulation by galectin-9. In particular, they focused on clarification of the details of differentiation control of $T_H17$ and Treg cells and identification of cells that secrete galectin-9 and regulate immunoreactions in vivo. As a result, the inventors of the present invention succeeded in identifying a novel galectin-9-secreting CD4 positive T cell ($T_H$GAL9 cell), and verified that this cell controls the differentiation of $T_H17$ and Treg cells. Also, the inventors of the present invention discovered that the $T_H$GAL9 cells are increased in vitro by the addition of galectin-9. The $T_H$GAL9 cells not only express galectin-9 on cell surfaces but also express a known Tr1 cell marker, and secret IL-10. This suggests the possibility that the $T_H$GAL9 cells might be the same as the Tr1 cells according to the current definition or belong to a subpopulation of the Tr1 cells. In this case, galectin-9 also is useful as a Tr1 cell marker, and would play a very important role in purification of the Tr1 cells and application of the Tr1 cells to treatment. In the present invention, the term "cell surface" is not particularly limited, and may refer to a surface of a cell membrane on the side facing the outside of the cell, for example. That is, the phrase "the state where galectin-9 is expressed on a cell surface" may refer to, but not particularly limited to, the state where galectin-9 is expressed in a cell membrane or on a surface thereof with the whole or part of the galectin-9 being exposed to the outside of the cell, for example.

The inventors of the present invention verified, using a mouse EAE model as one of autoimmune disease models, that the $T_H17$ cell differentiation inhibition and the Treg cell differentiation promotion by galectin-9 depend on IL-2 but do not depend on Tim-3. On the other hand, galectin-9 induced Tim-3-dependent apoptosis in differentiated Tim-3 positive $T_H17$ cells. The inventors of the present invention found out that CD4 positive T cells includes a cell population expressing galectin-9 on cell surfaces. Hereinafter, a CD4 positive T cell expressing galectin-9 on a cell surface may also be referred to as a "$T_H$GAL9 cell". By subjecting $T_H$GAL9 cells to TCR stimulation, it is possible to increase the expression of CD25, and to cause galectin-9 and IL-10 to be secreted thereafter, for example. Treg cells also may secrete IL-10 in some cases. However, $T_H$GAL9 cells do not express Foxp3 as a Treg marker. Hence, $T_H$GAL9 cells are considered to be different from Treg cells. $T_H$GAL9 expressed all the reported IL-10-producing type 1 regulatory T cell (Tr1 cell) markers. However, the expressions of these Tr1 markers are induced in most of CD25 positive CD4 cells by TCR stimulation, so that these Tr1 markers are not decisive Tr1 markers. Interestingly, inside CD4$^+$ T cells other than $T_H$GAL9, galectin-9 also is expressed in an amount equivalent to that in $T_H$GAL9. When $T_H$GAL9 cells are co-cultured with naïve T cells committed to differentiate into $T_H17$ cells, the production of IL-17 is inhibited and Treg cells are increased. These actions are similar to those of recombinant galectin-9. Thus, this strongly suggests that cells that regulate immunity via galectin-9 secretion in vivo are $T_H$GAL9 cells. Furthermore, it was found that $T_H$GAL9 cells having similar properties are present also in humans. The above-described findings show that cell surface galectin-9 is an excellent Tr1 marker, and also that a $T_H$GAL9 cell is a very useful cell that can be applied directly or indirectly to treatment of autoimmune diseases, allergic diseases, tumors, and other diseases.

Moreover, the inventors of the present invention demonstrated that the inhibition of $T_H17$ cell differentiation by the $T_H$GAL9 cell is inhibited by a galectin-9 inhibitor but not inhibited by an IL-10 inhibitor or a TGF-β inhibitor, thereby verifying that galectin-9 is a substance chiefly responsible for this inhibitory activity.

Moreover, the inventors of the present invention further discovered that cells similarly expressing galectin-9 on cell surfaces can be found also in: T cells other than CD4 positive T cells; γδT cells; natural killer cells (NK cells); B cells; and the like, thereby achieving the cell of the present invention. The cell of the present invention is a cell containing galectin-9, characterized in that the galectin-9 is expressed on a cell surface as described above, and other configurations are not particularly limited.

The fact that the cell of the present invention expresses galectin-9 on a cell surface is considered to verify that the cell of the present invention is a cell that secretes galectin-9. In other words, it is considered that the expression of galectin-9 on a cell surface is observed in the course of the process where the galectin-9 inside the cell is secreted out of the cell. It is to be noted, however, that this description merely illustrates one possible mechanism, and the cell of the present invention is by no means limited by this description.

The cell of the present invention ($T_H$GAL9 cell or the like) is a particularly useful cell that can be applied directly or indirectly to, e.g., treatment of autoimmune diseases, allergic diseases, tumors, and other diseases. For example, the cell of the present invention is useful in regulating immunity to prevent and treat illnesses. Furthermore, for example, the cell of the present invention is useful in the medical field for addressing infectious diseases, immune diseases, and organ transplantation, and also is useful as a reagent to be used in the fields of assays, biotechnology, etc.

In the present invention, "galectin-9" is not limited to natural (wild-type) galectin-9. For example, it may be a galectin-9 variant or the like having substantially equivalent activity to the natural (wild-type) galectin-9. The galectin-9 variant may be, for example, a substance that exhibits an activity to bind specifically to a specific carbohydrate chain (such an activity is owned by carbohydrate chain recognition sites of galectin-9), or an activity analogous thereto (such an activity may encompass a qualitative activity and/or a quantitative activity). Galectin-9 (wild-type galectin-9) has an activity to induce apoptosis of specific cells, for example. In the present invention, the galectin-9 variant may have an apoptosis-inducing activity of the wild-type galectin-9 or an activity analogous thereto. Also, the galectin-9 variant may exhibit an activity corresponding to altered or modified biological activity of galectin-9, which is preferable in some cases. In the present invention, galectin-9 variant may serve as a biologically active reagent having properties equivalent to or superior to the wild-type galectin-9 in the field of clinical tests, the field of analyses, or in the medical or pharmaceutical field.

In the present invention, "galectin-9 variant" is not particularly limited, and may be galectin-9 variant described in Patent Document 1 or the like, for example. More specifically, the galectin-9 variant may be as follows, for example. The galectin-9 variant may be, for example: a protein obtained by modification of the linker peptide or a region in the vicinity thereof in the wild-type galectin-9 or a protein having substantially equivalent activity to the wild-type galectin-9, or a salt thereof; a protein having an amino acid sequence obtained by modification of the wild-type galectin-9 or a protein having substantially equivalent activity to the wild-type galectin-9 so as to delete, substitute, or add one or more amino acids in the amino acid sequence of the linker peptide or a region in the vicinity thereof, or a salt thereof, resulting in modified degradation susceptibility of at least the linker peptide as compared with the wild-type galectin-9; a protein having substantially equivalent activity to the wild-type galectin-9 and having a homology of at least 70%, at least 75%, at least 80%, at least 85%, at least 90%, or at least 95% to the amino acid sequence of the wild-type galectin-9, or a salt thereof; or a protein obtained by binding (1) the N-terminal carbohydrate recognition domain (NCRD) of the wild-type galectin-9 or a polypeptide having substantially equivalent activity to the NCRD to (2) the C-terminal carbohydrate recognition domain region (CCRD) of the wild-type galectin-9 or a polypeptide having substantially equivalent activity to the CCRD via (3) a modified linker peptide having an amino acid sequence obtained by deletion, substitution, or addition of one or more amino acids in the amino acid sequence of the linker peptide of the wild-type galectin-9, or a salt thereof.

In preferable aspects, the galectin-9 variant may be the one composed of the following (1), (2), and (3), for example: (1) a polypeptide having the following amino acid sequence and having a lactose binding ability: the amino acid sequence of the following SEQ ID NO: 7 shown as the NCRD of the wild-type galectin-9; an amino acid sequence obtained by deletion, substitution, or addition of one or more amino acids in the amino acid sequence of SEQ ID NO: 7; or an amino acid sequence with a homology of at least 70%, at least 75%, at least 80%, at least 85%, at least 90%, or at least 95% to the amino acid sequence of SEQ ID NO: 7; (2) a polypeptide having the following amino acid sequence and having a lactose binding ability: the amino acid sequence of the following SEQ ID NO: 8 shown as the CCRD of the wild-type galectin-9; an amino acid sequence obtained by deletion, substitution, or addition of one or more amino acids in the amino acid sequence of SEQ ID NO: 8; or an amino acid sequence with a homology of at least 70%, at least 75%, at least 80%, at least 85%, at least 90%, or at least 95% to the amino acid sequence of SEQ ID NO: 8, and having a lactose binding ability, and (3) a polypeptide having, as a linker region linking the above (1) and (2), the following amino acid sequence, and preferably more stabilized against proteases such as matrix metalloprotease than the native (wild-type) galectin-9: the amino acid sequence of the following SEQ ID NO: 9; or an amino acid sequence obtained by deletion, substitution, or addition of one or more amino acids in the amino acid sequence of SEQ ID NO: 9. The linker region (3) encompasses: deletion analogs having an amino acid sequence obtained by deletion of one or more (e.g., 1 to 2, preferably 3 to 4, more preferably 5 to 6, still more preferably 7 to 8, and particularly preferably 1 to 9) amino acid residues in the amino acid sequence of SEQ ID NO: 9; substitution analogs having an amino acid sequence obtained by substitution of one or more (e.g., 1 to 9, preferably 1 to 8, more preferably 1 to 6, still more preferably 1 to 4, and particularly preferably 1 to 2) amino acid residues in the amino acid sequence of SEQ ID NO: 9 with other residues; and addition analogs having an amino acid sequence obtained by addition of one or more (e.g., 1 to 60, preferably 1 to 40, more preferably 1 to 20, more preferably 1 to 10, and particularly preferably 1 to 5) amino acid residues to the amino acid sequence of SEQ ID NO: 9 (provided that those amino acid residues are other than those shown in the part of SEQ ID NO: 10 or 11 obtained by deleting the amino acid sequence of SEQ ID NO: 9 therefrom). Typical examples of the linker region (3) include those having amino acid sequences obtained by modifying the amino acid sequence of SEQ ID NO: 9 so as to substitute amino acids therein with HM, RIP, or a sequence consisting of any two amino acids. The substitution, deletion, or insertion of amino acids may be the one causing no great change in physiological or chemical properties of a polypeptide, or in some cases, it may be the one causing preferable change in the same. A substituent of an amino acid in the amino acid sequence can be selected from other amino acids in the class to which the amino acid belongs. For example, non-polar (hydrophobic) amino acids include alanine, phenylalanine, leucine, isoleucine, valine, proline, tryptophan, and methionine; polar (neutral) amino acids include glycine, serine, threonine, cysteine, tyrosine, asparagine, and glutamine; positively charged amino acids (basic amino acids) include arginine, lysine, and histidine; and negatively charged amino acids (acidic amino acids) include aspartic acid and glutamic acid.

Examples of the linker region (3) further include: those having an amino acid sequence obtained by substitution of amino acid residues in the amino acid sequence of SEQ ID NO: 10 or 11 (excluding those in the part corresponding to the amino acid sequence of SEQ ID NO: 9) with HM, RIP, or a sequence consisting of any two amino acids; and those having an amino acid sequence obtained by deletion of, from amino acid residues in the amino acid sequence of SEQ ID NO: 10 or 11 (excluding those in the part corresponding to the amino acid sequence of SEQ ID NO: 9), all the residues but any six amino acids. Examples of the linker region (3) further include: deletion analogs having an amino acid sequence obtained by deletion of one or more (e.g., 1 to 5, preferably 3 to 10, more preferably 5 to 15, still more preferably 7 to 20, and particularly preferably 1 to 32) amino acid residues from the amino acid sequence of SEQ ID NO: 10 or 11 (e.g., excluding those in the part corresponding to the amino acid sequence of SEQ ID NO: 9, or in the case of SEQ ID NO: 10, those in the part corresponding to the amino acid sequence of SEQ ID NO: 11 may be excluded); substitution analogs having an amino acid sequence obtained by substitution of one or more (e.g., 1 to 9, preferably 1 to 8, more preferably 1 to 6, still more preferably 1 to 4, and particularly preferably 1 to 2) amino acid residues in the amino acid sequence of SEQ ID NO: 10 or 11 with any other residues; and addition analogs having an amino acid sequence obtained by addition of one or more (e.g., 1 to 60, preferably 1 to 40, more preferably 1 to 20, still more preferably 1 to 10, and particularly preferably 1 to 5) amino acid residues to the amino acid sequence of SEQ ID NO: 10 or 11 (provided that those amino acid residues are other than those shown in the part of SEQ ID NO: 10 or 11 obtained by deleting the amino acid sequence of SEQ ID NO: 9 therefrom).

All the mutants described above are encompassed in the present invention, as long as they retain the domain structure or the carbohydrate-binding ability characterizing the natural (wild-type) human galectin-9 protein, for example. Also, it is considered that the peptide or polypeptide of the present invention may encompass those having substantially the same primary structure conformations as the natural human galectin-9 proteins and those having a part of such conformations. Furthermore, it is also considered that the peptide or polypeptide of the present invention may encompass those having substantially equivalent biological activities to the natural human galectin-9 proteins. Furthermore, the peptide or polypeptide of the present invention can be one of naturally-occurring mutants. In the present invention, examples of human-derived proteins (or peptides or polypeptides) include those having an amino acid sequence with a homology higher than 60% or, in some cases, higher than 70%, more preferably at least 80% or 90% to an amino acid sequence selected from the group consisting of SEQ ID NOs: 1 to 3 listed in the Sequence Listing of WO 02/37114 A1. In the present invention, part of a human-derived protein may be any peptide as part of the human-derived protein (i.e., a partial peptide of the protein) as long as it has substantially equivalent activity to the galectin-9 protein of the present invention. Examples of the partial peptide of the protein according to the present invention include those having an amino acid sequence consisting of, among amino acid residues contained in the amino acid sequence constituting human galectin-9, at least 5 amino acid residues, preferably at least 20 amino acid residues, more preferably at least 50 amino acid residues, still more preferably at least 70 amino acid residues, yet more preferably at least 100 amino acid residues, and in some cases, at least 200 amino acid residues. Preferably, these amino acid residues are continuous, or, for example, these amino acid residues have the same homology as described above, with respect to the corresponding region in the amino acid sequence of any one of SEQ ID NOs: 1 to 3 in the Sequence Listing of WO 02/37114 A1.

```
                                                  (SEQ ID NO: 7)
Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Ser Gly Thr Arg Phe Ala Val Asn
            35                  40                  45

Phe Gln Thr Gly Phe Ser Gly Asn Asp Ile Ala Phe His Phe Asn Pro
        50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
                100                 105                 110

Met Val Asn Gly Ile Leu Phe Val Gln Tyr Phe His Arg Val Pro Phe
                115                 120                 125
```

-continued
```
His Arg Val Asp Thr Ile Ser Val Asn Gly Ser Val Gln Leu Ser Tyr
    130                 135                 140

Ile Ser Phe Gln
145
                                                        (SEQ ID NO: 8)
Thr Pro Ala Ile Pro Pro Met Met Tyr Pro His Pro Ala Tyr Pro Met
1               5                   10                  15

Pro Phe Ile Thr Thr Ile Leu Gly Gly Leu Tyr Pro Ser Lys Ser Ile
            20                  25                  30

Leu Leu Ser Gly Thr Val Leu Pro Ser Ala Gln Arg Phe His Ile Asn
        35                  40                  45

Leu Cys Ser Gly Asn His Ile Ala Phe His Leu Asn Pro Arg Phe Asp
    50                  55                  60

Glu Asn Ala Val Val Arg Asn Thr Gln Ile Asp Asn Ser Trp Gly Ser
65                  70                  75                  80

Glu Glu Arg Ser Leu Pro Arg Lys Met Pro Phe Val Arg Gly Gln Ser
                85                  90                  95

Phe Ser Val Trp Ile Leu Cys Glu Ala His Cys Leu Lys Val Ala Val
                100                 105                 110

Asp Gly Gln His Leu Phe Gln Tyr Tyr His Arg Leu Arg Asn Leu Pro
            115                 120                 125

Thr Ile Asn Arg Leu Glu Val Gly Gly Asp Ile Gln Leu Thr His Val
        130                 135                 140

Gln Thr
145
                                                        (SEQ ID NO: 9)
Thr Gln Thr Val Ile His Thr Val Gln Ser Ala Pro Gly Gln Met Phe
1               5                   10                  15

Ser
                                                        (SEQ ID NO: 10)
Asn Pro Arg Thr Val Pro Val Gln Pro Ala Phe Ser Thr Val Pro Phe
1               5                   10                  15

Ser Gln Pro Val Cys Phe Pro Pro Arg Pro Arg Gly Arg Arg Gln Lys
            20                  25                  30

Pro Pro Gly Val Trp Pro Ala Asn Pro Ala Pro Ile Thr Gln Thr Val
        35                  40                  45

Ile His Thr Val Gln Ser Ala Pro Gly Gln Met Phe Ser
    50                  55                  60

(SEQ ID NO: 11)
Pro Pro Gly Val Trp Pro Ala Asn Pro Ala Pro Ile Thr Gln Thr Val
1               5                   10                  15

Ile His Thr Val Gln Ser Ala Pro Gly Gln Met Phe Ser
            20                  25
```

In the present invention, when a galectin-9 variant has "substantially equivalent" activity to the wild-type (natural) galectin-9, it means, for example, that the galectin-9 variant retains the carbohydrate recognizing activity of the natural galectin-9. From a different viewpoint, when the galectin-9 variant has "substantially equivalent" activity to the wild-type (natural) galectin-9, it means, for example, that they have substantially the same protein activities, which more specifically means, e.g., predetermined cytotoxic activity, apoptosis-inducing activity, anti-inflammatory activity, anti-allergic activity, immunomodulating activity, carbohydrate chain binding activity, physiological activity, and biological activity. Furthermore, the meaning of the term also may encompass the case where they have activities of substantially the same quality, examples of which include binding activity, cytotoxic activity, and apoptosis-inducing activity. When activities have substantially the same quality, it means that these activities are qualitatively homogeneous, which means, for example, physiologically, pharmacologically, or biologically homogeneous. For instance, it is preferable that the activities such as the binding activity, cytotoxic activity, and apoptosis-inducing activity are equivalent (e.g., about 0.001- to about 1000-fold, preferably about 0.01- to about 100-fold, more preferably about 0.1- to about 20-fold, and still more preferably about 0.5- to about 2-fold), but quantitative factors such as the extents of these activities, molecular weights of the proteins, etc. may be different.

Other objects, features, advantages, and aspects of the present invention would be apparent to those skilled in the art from the following descriptions. It should be understood, however, that the following descriptions and descriptions in other parts of the specification including specific examples etc. are directed to preferred embodiments of the present invention and given merely for illustrative purposes. Those skilled in the art would easily understand that various changes and/or alterations (or modifications) of the present invention may be made without departing from the spirit and scope of the present invention as disclosed herein, based on knowledge from the following descriptions and other parts of the specification. All of the patent documents and reference documents listed herein are cited for illustrative purposes, and the entire disclosures thereof should be interpreted as being incorporated herein by reference.

In the present invention, a CD4 positive T cell that expresses galectin-9 on a cell surface was discovered together with the fact that this cell secretes galectin-9 to control the balance between $T_H17$ cells and Treg, and the cell was named "$T_H$GAL9 cell". It was found that the $T_H$GAL9 cell produces IL-10 and expresses Latency-associated peptide (LAP), NKG2D, lymphocyte activation gene-3 (LAG-3), and Cytotoxic T-Lymphocyte Antigen 4 (CTLA-4) on a cell surface. This suggests the possibility that the $T_H$GAL9 cell may be the same as a Foxp3 negative inhibitory T cell, i.e., a Tr1 cell (Non-Patent Documents 20 to 22) or belong to a subpopulation thereof.

Tr1 cells play an important role in immunological tolerance induced by plasmacytoid dendritic cells (Non-Patent Documents 20, 23 to 25, 15 to 18). In vitro, they are induced by subjecting naïve $CD4^+$ T cells to TCR stimulation in the presence of IL-27 or Vitamin D3/dexamethasone (Non-Patent Documents 26 to 29). Although the above-described LAP, NKG2D, LAG-3, and CTLA-4 are known as cell surface markers of the Tr1 cells, they are also expressed by $CD4^+CD25^+$ cells, which do not produce IL-10. Thus, a reliable Tr1 cell marker would be highly expressed inhibitory cytokine IL-10, which is considered to be chiefly responsible to the function of the Tr1 cell. However, the production of IL-10 can be seen not only in Tr1 cells but also in other cell groups including Treg cells, so that IL-10 cannot serve as a decisive Tr1 marker (Non-Patent Documents 30 to 31). Moreover, at present, no techniques are available that allows cells to be purified alive in a simple manner using the expression of IL-10 present inside the cells as an indicator. These facts render the Tr1 research and application thereof difficult.

In the present invention, as described above, immune cells expressing galectin-9 on cell surfaces, other than $T_H$GAL9, also were discovered. The possibility also is suggested that not only $T_H$GAL9 cells but also these cell groups can be used as surrogate markers in diagnosis, or can be applied to cell therapy after being purified using cell surface galectin-9.

The present invention provides cells that secretes galectin-9, as well as techniques applying the same. For example, the present invention provides type 1 T regulatory cells that secrete Gal-9 and IL-10, as well as techniques applying the same. The present invention provides techniques for identifying novel T cells ($T_H$GAL9 cells) that can secrete galectin-9 and making these cells available. The present invention also provides techniques for controlling the differentiation into $T_H17$ cells and Treg cells utilizing $T_H$GAL9 cells. The $T_H$GAL9 cells express not only galectin-9 on cell surfaces but also known Tr1 cell markers, and can secret IL-10, for example. The present invention also provides a technique for purifying Tr1 cells using galectin-9 as a Tr1 cell marker and also applying the thus-purified Tr1 cells to treatment. The present invention also provides a technique for inducing the increase in CD25 expression and secretion of galectin-9 and IL-10 by subjecting $T_H$GAL9 cells to TCR stimulation. The present invention also provides a technique for inhibiting the production of IL-17 and/or increasing Treg cells by co-culturing $T_H$GAL9 cells with naïve T cells committed to differentiate into $T_H17$ cells. The present invention also provides a technique for regulating immunity in vivo using $T_H$GAL9 cells. The present invention also provides a cell sorting technique for sorting out regulatory immune cells using cell surface galectin-9 as a marker, and a Tr1 cell sorting technique for sorting out IL-10-producing type 1 regulatory T cells (Tr1 cells) using cell surface galectin-9 as a marker.

The cells discovered in the present invention, e.g., a $T_H$GAL9 cell, are useful in the field of clinical tests as a reagent having biological activity, such as a diagnostic agent or a therapeutic agent, in the field of analysis, or in the medical or pharmaceutical field.

The method for separating (or isolating) the cells of the present invention (e.g., $T_H$GAL9 cells) from a tissue of a living organism (animal) is not particularly limited, and those skilled in the art can carry out the method without undue experimentation based on the descriptions in the specification and drawings of the present application, and common general technical knowledge at the time of filing the present application. For example, the method for separating (or isolating) the cells of the present invention (e.g., $T_H$GAL9 cell) from a tissue of a living organism (animal) may be a method for separating (or isolating) the cells by staining them with an anti-galectin-9 antibody and then separating (or isolating) the stained cells by sorting, as described in the following examples.

Also, the method for producing the cells of the present invention (e.g., $T_H$GAL9 cells) is not particularly limited, and may be, for example, a method for separating (or isolating) the cells of the present invention from an animal tissue in which the cells of the present invention already are present. In addition to or instead of this, the cell production method of the present invention may include the step of causing cells not expressing galectin-9 to express galectin-9 on cell surfaces, thus transforming the cells to the cells according to the present invention. This step can be performed in vivo or in vitro, for example. The method for performing this step in vivo may be, for example, as in the first production method of the present invention, administering galectin-9 to an animal, thus inducing expression of galectin-9 on cell surfaces of at least part of cells of the animal. The method for performing this step in vitro may be, for example, as in the second production method of the present invention, culturing one or more cells of an animal in the presence of galectin-9, thus inducing galectin-9 expression on a cell surface of at least one of the cells. The second production method of the present invention may be configured so that, for example, the cells of the animal include at least one cell expressing galectin-9 on a cell surface, and by culturing the cells in the presence of galectin-9, the proportion of the cell expressing galectin-9 on the cell surface is increased.

The term "diagnostic agent" as used herein refers to any agent that contributes to one or more diagnostic actions used in diagnostic applications of the present invention. These diagnostic applications may include a method for determining the presence of galectin-9-producing cells or a method for determining the presence of cells providing a galectin-9-binding substance. The diagnostic agent may be, for example, any agent that contains one selected from the group consisting of cells expressing galectin-9 on cell surfaces and homogenates of the cells.

The term "therapeutic agent" as used herein may refer to any agent that accomplishes or contributes to the accomplishment of one or more therapeutic actions used in therapeutic applications of the present invention. For example, in the case where a therapeutic agent is a cell expressing galectin-9 on a cell surface or a homogenate of the cell, the therapeutic agent can be administered to a mammal. The therapeutic agent may be the one that achieves its therapeutic purpose alone or in combination with any other agent (e.g., an agent to be used together with administration of galectin-9 variant and is applicable to other known treatments for, e.g., a particular tumor or autoimmunity; or a gene delivery vehicle that can cause galectin-9 expression easily in a mammal). For example, the therapeutic agents may contain a galectin-9 variant developed for other purposes, and may further contain an agonist of galectin-9 or an agent that modify or modulate the activities of galectin-9. The therapeutic agents can be, for example, a low molecular weight organic compound or substance, a peptide, a peptide-like compound or substance, a polynucleotide coding for a galectin-9 variant polypeptide, a galectin-9 variant polypeptide, or a transformed cell expressing a chimera or mutant of galectin-9 variant that is stabilized toward protease more than the native galectin-9.

The term "patient" as used herein may refer to any living organism to which any treatment or preventive care can be applied. Examples of the patient include, but not limited to, eukaryotes. For example, an eukaryote as a patient may be a vertebrate. Thus, for example, the patient preferably is a mammal. The mammal can be a human, for example.

General methods for production and use of the therapeutic agent and/or diagnostic agent according to the present invention will be described below. In one aspect, the present invention provides a technique for treating diseases, illnesses, and abnormal conditions caused by the deficiency or absence of physiological or biological activity owned by galectin-9. The treatment technique includes, for example, the step of providing a therapeutic agent containing the cells of the present invention (e.g., $T_H$GAL9 cells or the like) and/or the step of administering an effective amount of therapeutic agent containing the cells of the present invention (e.g., $T_H$GAL9 cells or the like) to a mammal having any of the above described diseases etc. The cell of the present invention (e.g., $T_H$GAL9 cell or the like) may be used so as to exhibit: cytotoxic activity against malignant tumor cells; apoptosis-inducing activity against malignant tumor cells; anti-tumor activity (anti-cancer activity) against malignant tumor cells; apoptosis-inducing activity against activated T cells, especially against CD4 positive T cells; immunomodulating activity; anti-inflammatory action; and anti-allergic action. Thus, it is expected that the cell of the present invention can be useful as an anti-tumor agent (anti-cancer agent), an anti-allergic agent, an immunomodulatory agent, an anti-autoimmune disease agent, an anti-inflammatory agent, and an alternate agent for adrenocortical steroid hormones.

The above-described treatment technique encompasses a method for treating an autoimmune disease characterized by a large amount of activated T-cells. The terms "autoimmune disease" and "autoimmunity" both refer to a disorder characterized by autoimmunity in mammals (a response of an immune system against self-components). An autoimmune response can develop into symptoms showing clinical signs. Strictly speaking, transplantation rejection is not an autoimmunoreaction. However, when a patient has surgery to replace or graft cells, tissue, or an organ to treat his symptoms, the body undergoing allogeneic transplantation can react immunologically against a foreign graft. "Transplantation rejection" occurs if, during allogeneic transplantation of cells, tissue, or an organ from one member of a species to another, the receptor (recipient) causes an immune response sufficient to reject the transplanted cells, tissue, or organ.

Examples of "tumor" that can be treated by the method and therapeutic agent according to the present invention may include malignant tumors. For example, tumors that may metastasize are malignant tumors. Generally, there are two main categories of malignant tumors, namely, epithelial malignant tumors and non-epithelial malignant tumors. In some cases, malignant tumors may be classified into cancers, sarcoma, leukemia, etc. However, when ordinary people simply say "cancers", it refers to malignant tumors in most cases. The term "cancers" as used herein may be interpreted broadly, and should not be interpreted as merely referring to epithelial malignant tumors. The term "cancers" as used herein may encompass epithelial malignant tumors and non-epithelial malignant tumors (including those that are tumorigenic and non-tumorigenic tumorigenic). Examples of the cancers include skin cancers (which may include melanomas), breast cancers, ovarian cancers, uterine cancers, malignant testicular tumors, prostate cancers, bladder cancers, kidney cancers, thyroid cancers, pharyngeal and laryngeal cancers, tongue cancers, maxillary cancers, esophageal cancers, stomach cancers, colon and rectal cancers, lung and bronchial cancers, liver cancers (including hepatocellular cancers and intrahepatic bile duct cancers), extrahepatic bile duct and gallbladder cancers, pancreatic cancers, leukemia, malignant lymphoma, plasmacytoma, osteosarcoma, chondrosarcoma, leiomyosarcoma, rhabdomyosarcoma, liposarcoma, fibrosarcoma, malignant hemangioma, malignant hemangioendothelioma, and brain tumors (including meningioma, glioma, astrocytoma, etc.). It should be understood, however, that examples of the cancers are not limited thereto, and also may encompass cancers for which any favorable result can be obtained by the use of the cell of the present invention (e.g., $T_H$GAL9 cell or the like), and further, cancers which yield any physiological or biological response when the cell of the present invention (e.g., $T_H$GAL9 cell or the like) is involved therein.

Examples of the "autoimmune diseases" that can be treated by the method and therapeutic agent according to the present invention include multiple sclerosis, Hashimoto's thyroiditis, systemic lupus erythematosus (SLE), Goodpasture's syndrome, pemphigus, receptor autoimmunity, autoimmune hemolytic anemia, autoimmune thrombocytopenic purpura, osteoarthritis, chronic rheumatoid arthritis, scleroderma with anticollagen antibodies involved, mixed connective tissue diseases, polymyositis, pernicious anemia, idiopathic Addison's disease, spontaneous infertility, glomerulonephritis, bullous pemphigoid, adrenergic drug resistance, chronic active hepatitis, primary biliary cirrhosis, autoimmune-based endocrine gland failure, vitiligo, vasculitis, post-myocardial infarction, post-cardiotomy syndrome, urticaria, atopic dermatitis, autoimmune-based asthma, autoimmune-based inflammatory reactions, granulomatous disorders, ankylosing spondylitis, post-streptococcal glomerulonephritis, autoimmune hemolytic anemia, encephalitis, autoimmunoreactions secondary to lymphoma, degenerative disorders, and atrophic disorders. Examples of autoimmune diseases involving autoimmunity against receptors include Graves' disease, myasthenia gravis, and insulin resistance. Examples of autoimmune diseases involving adrenergic drug resistance include asthma and cystic fibrosis.

Other autoimmune diseases to which the present invention is applicable include those for which animal models exist. Examples of such autoimmune diseases include Sjögren's syndrome (autoimmune dacryoadenitis or immune-mediated sialadenitis), autoimmune myocarditis, primary biliary cirrhosis (PBC), inflammatory heart diseases, mercury-induced renal autoimmunity, insulin-dependent diabetes (type I diabetes or IDD), post-thymectomy autoimmunity, central nervous system (CNS) demyelination disorders, CNS lupus, narcolepsy, immune-mediated PNS disorders, osteoarthritis, chronic rheumatoid arthritis, uveitis, medullary cystic fibrosis, autoimmune hemolytic diseases, autoimmune vasculitis, ovarian autoimmune diseases, and scleroderma. Examples of autoimmune diseases characterized by central nervous system (CNS) demyelination disorders include multiple sclerosis (MS). A peripheral nervous system (PNS) autoimmune disease may be Guillain-Barre syndrome (GBS), for example.

The present invention discloses a method for treating a mammal afflicted with a disease or illness selected from: tumors including malignant tumors such as cancers; allergic diseases; inflammations; immune abnormality; and autoimmune diseases including activated lymphocytes (in particular, activated T cells, and the activated lymphocytes may include activated B cells) by administrating a therapeutic agent containing at least one selected from the group consisting of the cells of the present invention (e.g., $T_H$GAL9 cells and the like); homogenates of the cells; and extracts of the cells (e.g., the therapeutic agent may be a composition containing, as a therapeutically active ingredient: the cell of the present invention (e.g., $T_H$GAL9 cell or the like); or a stimulating agent for stimulating the cell). Autoimmune diseases that can be treated by the method and composition of the present invention include any autoimmune diseases and transplantation rejections (e.g., including, but not limited to, those autoimmune diseases listed herein).

When the present invention is used to obtain cytotoxic actions on tumor cells including malignant tumor cells such as cancer cells, to obtain anti-allergic actions, to obtain anti-inflammatory actions, to normalize immune abnormality, or to induce apoptosis of activated lymphocytes (which may include activated T cells, in particular), the present invention should be interpreted in the same way as in the case of the above-described autoimmunity.

A substance containing at least one selected from the group consisting of the cells of the present invention (e.g., $T_H$GAL9 cells and the like); homogenates of the cells; and extracts of the cells has high potential to serve as an anti-tumor agent, an anti-allergic agent, an immunomodulatory agent, an anti-autoimmune disease agent, an anti-inflammatory agent, and an agent utilizing an activity similar to that of adrenocortical steroid hormone, and is considered to exhibit biological activity useful for the following pathological symptoms and diseases.

Inflammatory diseases include a variety of acute and chronic inflammations occurring in various organs, allergic and autoimmune inflammations, and infectious diseases.

Examples of the acute and chronic diseases include a wide variety of inflammations. Specifically, examples of inflammations in the lungs include bronchitis, bronchopneumonia, interstitial pneumonia, pneumonitis, bronchiolitis, and acute mediastinitis. Examples of inflammations in other organs include pericarditis, endocarditis, myocarditis, stomatitis, angular stomatitis, tonsillitis, pharyngitis, laryngitis, esophagitis, peritonitis, acute gastritis, chronic gastritis, acute enteritis, appendicitis, ischemic colitis, drug-induced colitis, proctitis, various acute and chronic hepatitis (such as hepatitis A, hepatitis B, hepatitis C, fulminant hepatitis, and chronic hepatitis), cirrhosis, cholecystitis, acute and chronic pancreatitis, acute and chronic nephritis, membranous glomerulonephritis, glomerulonephritis, IgA nephropathy, a variety of cystitis, encephalomyelitis, mastitis, dermatitis, superficial keratitis, xerotic keratitis, a variety of otitis media and rhinitis, sinusitis, nasal polyp, gingivitis, periodontitis, and paradentitis.

Also, a substance containing at least one selected from the group consisting of the cells of the present invention (e.g., $T_H$GAL9 cells and the like); homogenates of the cells; and extracts of the cells can be effective for, for example, neurogenic inflammation (e.g., neurogenic gastritis, neurogenic cystitis, and the like). For instance, it has been verified that galectin-9 strongly inhibits inflammatory responses in capsaicin-induced neurogenic skin inflammation models. Capsaicin is a substance that stimulates peripheral nerves, thereby causing neurogenic inflammation and pain. Capsaicin stimulates the release of substance P, which is a neuropeptide stored by sensory C fiber endings. Substance P induces release of histamine from mast cells, thereby causing vasodilatation, which may result in edema. Sensory nerves are stimulated by the released histamine. As a result, an enhancement cycle is established in which substance P is released from C fiber endings and acts on surrounding mast cells, thereby causing more histamine to be released. Galectins exert inhibitory actions on this pathogenic process.

Further, capsaicin binds to a capsaicin receptor (vanilloid receptor) as a pain sensor in sensory nerve endings, thus causing pain. Pain is caused by activation of sensory nerve endings with chemical stimulation (by acid or the like), thermal stimulation (by hot water or the like), or excessive mechanical stimulation (by a blow or the like). The capsaicin receptor also is involved in pain caused by such stimulation. Therefore, it is suggested that galectin-9 may inhibit capsaicin receptor-mediated activation of nerve endings. Thus, galectin-9 has much promise in analgesic applications including relief of pain associated with cancers and inflammations.

Examples of the allergic inflammatory diseases include systemic anaphylaxis, bronchial asthma, hypersensitivity pneumonitis, pollinosis, allergic rhinitis, allergic conjunctivitis, immune complex-induced allergic diseases, and angioneurotic edema.

Examples of the autoimmune inflammations (autoimmune diseases) include: systemic diseases (chronic rheumatoid arthritis, systemic lupus erythematosus, polyarteritis nodosa, scleroderma, polymyositis and dermatomyositis, Sjögren's syndrome, Behcet's disease, and the like); nervous system diseases (multiple sclerosis, myasthenia gravis, HAM (HTLV-1 myelopathy), amyotrophic lateral sclerosis, and the like); endocrine diseases (Basedow's disease, Hashimoto's disease, type 1 diabetes, and the like); blood diseases (idiopathic thrombocytopenic purpura, autoimmune hemolytic anemia, aplastic anemia, and the like); respiratory diseases (sarcoidosis, pulmonary fibrosis, and the like); gastrointestinal diseases (ulcerative colitis, Crohn's disease, and the like); hepatic diseases (autoimmune hepatitis, primary biliary cirrhosis, primary sclerosing cholangitis, autoimmune cholangitis, and the like); and renal and urinary system diseases (anti-neutrophil cytoplasmic antibody associated nephritis, vasculitis, Goodpasture's syndrome, anti-glomerular basement membrane antibody disease, and the like).

Infectious diseases collectively refer to diseases resulting from damage to cells, tissue, and organs of living organisms by pathogens. Regarding infectious diseases, the following book can be referred to: Supervisor: Rikuo MACHINAMI, Editor: Junichi HATA & Atsuhiko SAKAMOTO, "Hyoujun Byourigaku, 2nd Edition", Igaku-Shoin Ltd., published on Mar. 15, 2002. Pathogens that cause infectious diseases in human include: 1) bacteria (including spirochetes, chlamydiae, and rickettsiae); 2) viruses; 3) fungi; 4) plants (algae); 5) protozoa; 6) parasites (trematodes, cestodes, nematodes); and 7) arthropods. Major diseases caused by the respective pathogens include: bacterial infections (cholera, pest, *Escherichia coli* infection, and the like); spirochete infections (leptospirosis, and the like); chlamydial infections (psittacosis, and the like); rickettsial infections (epidemic typhus, tetanus, and the like); viral infections (zoster, viral hemorrhagic fever, rabies, and the like); fungal infections (candidiasis, cryptococcosis, aspergillosis, and the like); protozoan infections (amebic dysentery, malaria, toxoplasmosis, and the like); parasitic infections (trematodiasis, nematodiasis, and the like); and other infectious diseases such as mycoplasma infections (mycoplasma pneumonia and the like) and mycobacterial infections (tuberculosis, atypical mycobacterial infection, and the like).

Sarcomas and cancers include brain tumors (glioblastoma multiforme and the like), spinal cord tumors, maxillary sinus cancer, pancreatic ductal adenocarcinoma, gingival cancers, tongue cancers, lip cancers, nasopharyngeal cancers, oropharyngeal cancers, hypopharyngeal cancers, laryngeal cancers, thyroid cancers, parathyroid cancers, lung cancers, pleural tumors, carcinomatous peritonitis, carcinomatous pleurisy, esophageal cancers, stomach cancers, large bowel cancers, bile duct cancers, gallbladder cancers, pancreatic cancers, liver cancers, kidney cancers, bladder cancers, prostate cancers, penile cancers, testicular tumors, adrenal cancers, cervical cancers, endometrial cancers, vaginal cancers, vulvar cancers, ovarian cancers, chorioepithelioma, malignant bone tumors, soft tissue sarcomas, breast cancers, skin cancers, malignant melanoma, basal cell tumors, leukemia, myelofibrosis involving myeloid metaplasia, malignant lymphoma, Hodgkin's disease, plasmacytoma, and glioma.

According to the present invention, for example, as described above, it is possible to diagnose a disease of an animal or a symptom caused by the disease by detecting, in a tissue of the animal containing or not containing the cell of the present invention, the cell of the present invention qualitatively or quantitatively by the cell detection method of the present invention. The disease of the animal is not particularly limited, and can be any of the above-described diseases, for example. Furthermore, according to the present invention, for example, as described above, it is possible to determine a therapeutic effect on a disease of an animal by a method including the steps of treating the disease of the animal; diagnosing the disease or a symptom caused by the disease by the diagnostic method of the present invention before and after the treatment; and comparing diagnostic results obtained before and after the treatment. The disease of the animal is not particularly limited, and can be any of the above-described diseases, for example.

EXAMPLES

The present invention will be described specifically below with reference to examples, which are provided in order to present information on specific embodiments of the present invention only for illustrative purposes. These illustrative examples are provided to give explanations on specific embodiments of the present invention, and should not be construed as in any sense limiting or restricting the scope of the invention disclosed herein. It should be understood that, in the present invention, various embodiments can be made or executed within the spirit, scope, and concept disclosed herein.

The following examples can be carried out by those skilled in the art without undue experimentation based on specific descriptions in the respective examples and common general technical knowledge at the time of filing the present application. In the following examples, if a mechanism by which an observed phenomenon occurs is considered, it should be understood that such a mechanism merely is one conceivable example, and does not limit the present invention by any means.

<Materials and Methods Used in Experiments>

In the following, particularly important materials and methods used in experiments will be described.
(Recombinant Galectin-9)

Every recombinant galectin 9 used in the examples was stabilized human galectin 9 (G9NC(null)) prepared according to reported methods (Non-Patent Documents 12 and 33, and Patent Document 1). The authentic sample exhibited a purity of at least 95% according to SDS-PAGE and a protein purity test with Coomassie Brilliant Blue staining. The amount of endotoxin contained therein was not more than 0.1 ng per 1 mg of the stabilized human galectin, according to the kinetic turbidimetric Limulus test. The binding affinity of the stabilized human galectin-9 to mouse Tim-3 is equivalent to that of mouse galectin-9. Molar concentrations were calculated assuming a molecular weight of 33065.

The stabilized human galectin-9 (G9NC(null)) preparation method described in Patent Document 1 is as follows.
(A) Construction of Galectin-9 Variant Expression Vector
The expression vector was constructed using the following (1) to (3):
(1) cDNA prepared from a poly(A)$^+$ RNA fraction of Jurkat cells
(2) pET-11a vector (STRATAGENE)
(3) PCR primers:

```
G9NCRD1:
                                    (SEQ ID NO: 1)
CGTCCTCATATGGCCTTCAGCGGTTCCCAG

G9NCRD6:
                                    (SEQ ID NO: 2)
CGACCGCATATGCTGGAAGCTGATGTAGGACAG

G9CCRD5:
                                    (SEQ ID NO: 3)
CGTCCTCATATGACTCCCGCCATCCCACCTATG

G9CCRD6:
                                    (SEQ ID NO: 4)
CGACCGGGATCCCTATGTCTGCACATGGGTCAG
```

The Jurkat cells (T cell-derived cells) were obtained from American Type Culture Collection (ATCC). The cell line was maintained in a RPMI-1640 medium (Sigma, St. Louis, USA) containing 10% FCS at 37° C. under 5% $CO_2$. Total RNA extraction from the Jurkat cells was carried out in the following manner. The Jurkat cells cultured in the 10% FBS-containing RPMI-1640 medium were collected by centrifugation, and washed twice with 10 ml of PBS. To the washed cell pellets, ISOGEN (trade name, NIPPON GENE CO., LTD.) was added (15 ml per $2\times10^8$ cells). Then, in accordance with the manual (NIPPON GENE CO., LTD.), total RNA was extracted therefrom. Purification of poly(A)$^+$ RNA from the total RNA and synthesis of cDNA were carried out in the following manner. The total RNA extracted from the Jurkat cells was dissolved in DEPC-treated water at a concentration of 1 mg/ml. poly(A)$^+$ RNA was purified from the total RNA using a PolyA Ttract mRNA Isolation System (trade name, Promega) in accordance with its manual. The purified poly(A)$^+$ RNA was dissolved in DEPC-treated water at a concentration of 5 µg/20 µl. cDNA was synthesized from 5 µg of the poly(A)$^+$ RNA using a First-Strand cDNA Synthesis Kit (trade name, Amersham Biosciences) in accordance with its manual (as a primer, Not I-d(T)$_{18}$ was used).

Next, the N-terminal carbohydrate recognition domain (NCRD) and the C-terminal carbohydrate recognition domain (CCRD) of galectin-9 were inserted into the NdeI-BamHI site of a pET-11a vector in a manner outlined in the following. Thus, an expression vector for a modified galectin-9 (G9NC(null)) lacking the linker peptide was produced.

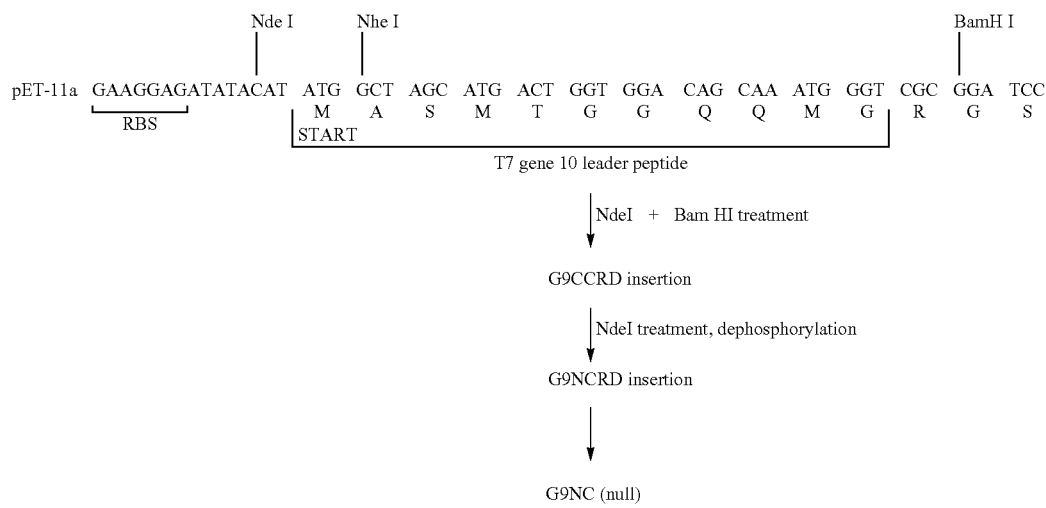

T7 gene 10 leader peptide

↓ NdeI + Bam HI treatment

G9CCRD insertion

↓ NdeI treatment, dephosphorylation

G9NCRD insertion

↓

G9NC (null)

First, from the galectin-9 cDNA, the following (1) and (2) were obtained: (1) cDNA corresponding to the C-terminal CRD of human galectin-9; and (2) cDNA corresponding to the N-terminal CRD of human galectin-9. More specifically, the cDNA corresponding to the C-terminal CRD of human galectin-9 (G9CCRD) was amplified from the cDNA using the PCR primers G9CCRD5 and G9CCRD6. G9CCRD was cleaved with restriction enzymes (NdeI+BamHI), and inserted into the pET-11a vector treated with the same restriction enzymes. Thus, pET-G9CCRD was obtained. PCR was conducted using a KOD DNA polymerase kit (TOYOBO Code No. KOD-101). A PCR reaction mixture (dNTP mix, 25 mM MgCl$_2$, 10× Buffer, KOD DNA polymerase (0.05 u), primers, and a template cDNA) was reacted under the following PCR cycle conditions: the reaction mixture was treated at 94° C. for 2 minutes, then was subjected to 25 cycles of treatment (with a treatment at 98° C. for 15 seconds, at 65° C. for 2 seconds, and at 74° C. for 30 seconds as one cycle), and finally, the reaction was terminated at 4° C. The PCR amplified fragment was inserted into the vector using a Ligation high kit (TOYOBO Code No. LGK-101). To cause a reaction, the PCR-amplified fragment was mixed with the vector at a molar ratio of insert:vector=about 5:1, and then the resultant DNA solution was mixed with a reagent "Ligation high". The amount (volume) of the reagent was ½ of the total amount (volume) of the DNA solution. The reaction was allowed to proceed at 16° C. for 16 hours (O/N), thereby achieving insertion.

Also, the cDNA corresponding to the N-terminal CRD of human galectin-9 (G9NCRD) was amplified from the galectin-9 cDNA using PCR primers G9NCRD1 and G9NCRD6. G9NCRD was cleaved with a restriction enzyme (NdeI). Into the pET-G9CCRD that had been treated with the same restriction enzyme (NdeI) and then further dephosphorylated, the resultant fragment was inserted. Thus, pET-G9NC (null) was obtained. The PCR amplification and incorporation into the vector were carried out in the same manner as in the above. The pET-G9NC (null) codes for a polypeptide having an amino acid sequence obtained by substitution of 29 amino acids from Pro-149 to Ser-177 in the amino acid sequence of human M-type galectin-9 with the His-Met sequence. In other words, the pET-G9NC (null) has a base sequence of the following SEQ ID NO: 5, which codes for a polypeptide having an amino acid sequence of the following SEQ ID NO: 6.

```
                                                          (SEQ ID NO: 5)
atg gcc ttc agc ggt tcc cag gct ccc tac ctg agt cca gct gtc ccc   48
Met Ala Phe Ser Gly Ser Gln Ala Pro Tyr Leu Ser Pro Ala Val Pro
1               5                   10                  15 ttt tct ggg act att caa gga ggt ctc cag gac gga ctt cag atc act   96
Phe Ser Gly Thr Ile Gln Gly Gly Leu Gln Asp Gly Leu Gln Ile Thr
            20                  25                  30 gtc aat ggg acc gtt ctc agc tcc agt gga acc agg ttt gct gtg aac  144
Val Asn Gly Thr Val Leu Ser Ser Ser Gly Thr Arg Phe Ala Val Asn
        35                  40                  45 ttt cag act ggc ttc agt gga aat gac att gcc ttc cac ttc aac cct  192
Phe Gln Thr Gly Phe Ser Gly Asn Asp Ile Ala Phe His Phe Asn Pro
    50                  55                  60 cgg ttt gaa gat gga ggg tac gtg gtg tgc aac acg agg cag aac gga  240
Arg Phe Glu Asp Gly Gly Tyr Val Val Cys Asn Thr Arg Gln Asn Gly
65                  70                  75                  80 agc tgg ggg ccc gag gag agg aag aca cac atg cct ttc cag aag ggg  288
Ser Trp Gly Pro Glu Glu Arg Lys Thr His Met Pro Phe Gln Lys Gly
                85                  90                  95
```

-continued

```
atg ccc ttt gac ctc tgc ttc ctg gtg cag agc tca gat ttc aag gtg   336
Met Pro Phe Asp Leu Cys Phe Len Val Gln Ser Ser Asp Phe Lys Val
        100                 105                 110 atg gtg aac ggg atc ctc ttc gtg cag tac ttc cac cgc gtg ccc ttc   384
Met Val Asn Gly Ile Leu Phe Val Gln Tyr Phe His Arg Val Pro Phe
    115                 120                 125 cac cgt gtg gac acc atc tcc gtc aat ggc tct gtg cag ctg tcc tac   432
His Arg Val Asp Thr Ile Ser Val Asn Gly Ser Val Gln Len Ser Tyr
130                 135                 140 atc agc ttc cag cat atg act ccc gcc atc cca cct atg atg tac ccc   480
Ile Ser Phe Gln His Met Thr Pro Ala Ile Pro Pro Met Met Tyr Pro
145                 150                 155                 160 cac ccc gcc tat ccg atg cct ttc atc acc acc att ctg gga ggg ctg   528
His Pro Ala Tyr Pro Met Pro Phe Ile Thr Thr Ile Leu Gly Gly Leu
                165                 170                 175 tac cca tcc aag tcc atc ctc ctg tca ggc act gtc ctg ccc agt gct   576
Tyr Pro Ser Lys Ser Ile Leu Leu Ser Gly Thr Val Leu Pro Ser Ala
            180                 185                 190 cag agg ttc cac atc aac ctg tgc tct ggg aac cac atc gcc ttc cac   624
Gln Arg Phe His Ile Asn Leu Cys Ser Gly Asn His Ile Ala Phe His
        195                 200                 205 ctg aac ccc cgt ttt gat gag aat gct gtg gtc cgc aac acc cag atc   672
Leu Asn Pro Arg Phe Asp Glu Asn Ala Val Val Arg Asn Thr Gln Ile
    210                 215                 220 gac aac tcc tgg ggg tct gag gag cga agt ctg ccc cga aaa atg ccc   720
Asp Asn Ser Trp Gly Ser Glu Glu Arg Ser Leu Pro Arg Lys Met Pro
225                 230                 235                 240 ttc gtc cgt ggc cag agc ttc tca gtg tgg ctc ttg tgt gaa gct cac   768
Phe Val Arg Gly Gln Ser Phe Ser Val Trp Ile Leu Cys Glu Ala His
                245                 250                 255 tgc ctc aag gtg gcc gtg gat ggt cag cac ctg ttt gaa tac tac cat   816
Cys Leu Lys Val Ala Val Asp Gly Gln His Leu Phe Glu Tyr Tyr His
            260                 265                 270 cgc ctg agg aac ctg ccc acc atc aac aga ctg gaa gtg ggg ggc gac   864
Arg Leu Arg Asn Leu Pro Thr Ile Asn Arg Len Glu Val Gly Gly Asp
        275                 280                 285 ctc cag ctg acc cat gtg cag aca tag                               891
Ile Gln Leu Thr His Val Gln Thr
    290                 295

(SEQ ID NO: 6)
Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Gly Thr Arg Phe Ala Val Asn
            35                  40                  45

Phe Gln Thr Gly Phe Ser Gly Asn Asp Ile Ala Phe His Phe Asn Pro
        50                  55                  60

Arg Phe Glu Asp Gly Gly Tyr Val Val Cys Asn Thr Arg Glh Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140
```

-continued

```
Ile Ser Phe Gln His Met Thr Pro Ala Ile Pro Pro Met Met Tyr Pro
145                 150                 155                 160

His Pro Ala Tyr Pro Met Pro Phe Ile Thr Thr Ile Leu Gly Gly Leu
                165                 170                 175

Tyr Pro Ser Lys Ser Ile Leu Leu Ser Gly Thr Val Leu Pro Ser Ala
                180                 185                 190

Gln Arg Phe His Ile Asn Leu Cys Ser Gly Asn His Ile Ala Phe His
                195                 200                 205

Leu Asn Pro Arg Phe Asp Glu Asn Ala Val Val Arg Asn Thr Gln Ile
        210                 215                 220

Asp Asn Ser Trp Gly Ser Glu Glu Arg Ser Leu Pro Arg Lys Met Pro
225                 230                 235                 240

Phe Val Arg Gly Gln Ser Phe Ser Val Trp Ile Leu Cys Glu Ala His
                245                 250                 255

Cys Leu Lys Val Ala Val Asp Gly Gln His Leu Phe Glu Tyr Tyr His
                260                 265                 270

Arg Leu Arg Asn Leu Pro Thr Ile Asn Arg Leu Glu Val Gly Gly Asp
        275                 280                 285

Ile Gln Leu Thr His Val Gln Thr
    290                 295
```

(B) Expression and Purification of Galectin-9 Variant Recombinant Protein

The expression plasmid vector pET-G9NC (null) obtained in the above-described process (A) was introduced into *E. coli* (BL21 (DE3)). The introduction was carried out by electroporation. More specifically, competent BL21 (DE3) was mixed with an aqueous plasmid vector solution, and the resultant mixture was subjected to electroporation at a voltage of 1.8 kV for transfection.

The expression of the recombinant protein was induced by culturing the *E. coli* in a 2×YT medium containing 2% (w/v) glucose and 100 μg/ml ampicillin, and then adding 0.1 M isopropyl-β-D-thiogalactopyranoside to the medium (final concentration: 0.1 mM) at a time point when the absorbance of the medium at 600 nm reached 0.7. After the *E. coli* was cultured at 20° C. for 18 hours, the bacterial cells were collected by centrifugation, and then suspend in 10 mM Tris-HCl (pH 7.5) containing 0.5 M NaCl, 1 mM DTT, and 1 mM PMSF. The resultant suspension was subjected to sonication for 10 minutes. Thereafter, 10% (w/v) Triton X-100 was added to the suspension (final concentration: 1%), and the resultant mixture was stirred at 4° C. for 30 minutes. The mixture was centrifuged at 15,000×g for 30 minutes, and the resultant supernatant was subjected to affinity chromatography using lactose-agarose to purify the recombinant protein in the supernatant. Cellufine ET clean L (CHISSO) was used to remove endotoxin, and whether or not the endotoxin had been removed was checked by a kinetic turbidimetric *Limulus* test using a Toxinometer.

Figure 28:
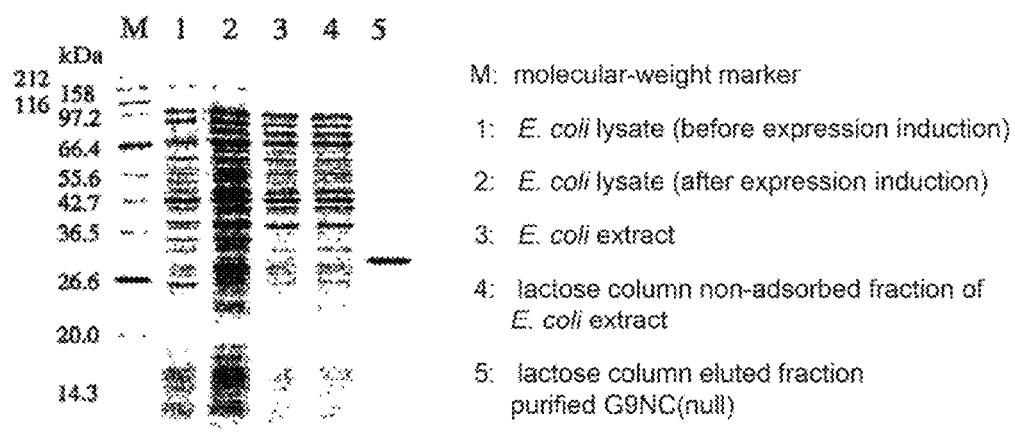
FIG. 28 shows electrophoretic patterns obtained using a galectin-9 variant recombinant protein in still another example of the present invention.

As a result, an authentic sample of the recombinant protein with high purity was obtained with a relatively high yield. The result of electrophoresis of the thus-obtained recombinant protein was shown in FIG. 28. SDS-PAGE conditions were as follows: gel: Acrylamide-BIS (12% gel), electrophoresis buffer: 25 mM Tris-192 mM glycine-0.1% SDS, electrophoretic conditions: 180 V, 45 min., and staining: CBB, 60° C./30 min. The electrophoresis sample was adsorbed on Strata Clean™ Resin (Stratagene), and the concentration thereof was adjusted to 0.2 mg/ml using 1× sample buffer (62.5 mM Tris-HCl, pH 6.8, 2% (w/v) SDS, 5% (W/V) 2-ME, Glycerol). The mixture was heat-treated at 98° C./3 min, and then was subjected to electrophoresis with the amount of the protein per lane being about 2 μg. The purified G9NC (null) could be stored stably at 4° C. for at least 600 days.

(Antibody)

The following antibodies were used for cell staining: an anti-mouse CD4-FITC antibody (Becton Dickinson or eBioscience, San Diego, Calif.), an anti-mouse Tim-3-PE antibody (eBioscience), an anti-mouse galectin-9-Alexa 488 antibody (clone 108A2, GalPharma), an anti-mouse galectin-9-PE antibody (clone 108A2, Biolegend), an anti-mouse CD25-APC antibody (Biolegend), an anti-mouse Foxp3-APC antibody (eBioscience), anti-human/mouse LAP-PE antibody (R&D Systems), an anti-mouse NKG2D-PE antibody (Biolegend), an anti-mouse LAG-3-PE antibody (Biolegend), an anti-mouse CTLA-4-PE antibody (Biolegend), an anti-mouse IL-17 antibody—(for FACS), an anti-mouse PDCA-1-APC antibody (Biolegend), an anti-mouse CD11c-Alexa 488 antibody (Biolegend), an anti-mouse CD19 antibody (Biolegend), an anti-mouse GL-7 antibody (Biolegend), an anti-mouse CXCR4 antibody (Biolegend), an anti-mouse ICOS-PE antibody (eBiosciences), an anti-mouse CXCR5-APC antibody (BD Pharmingen), an anti-human galectin-9-Alexa 488 antibody (clone 9M1-3, GalPharma), an anti-human CD4-FITC antibody (Biolegend), an anti-human CD4-PE antibody (Biolegend), an anti-human CD25-APC antibody (Biolegend), an anti-human/mouse Foxp3-PE antibody (Biolegend), an anti-mouse IL-10 antibody (Biolegend), an anti-mouse IL-10 neutralizing antibody (R&D Systems), an anti-mouse IL-10R neutralizing antibody (R&D Systems), and an anti-mouse TGF-β neutralizing antibody (R&D Systems).

(Other Reagents)

Apoptosis measurement was carried out using an Annexin V-EGFP Apoptosis Detection kit (Medical & Biological Laboratories, Nagoya, Japan). For staining of intracellular antigens, a BD Cytofix/Cytoperm Kit (Becton Dickinson) was used to immobilize cells and make cell membranes permeable. These kits were used in accordance with instructions for use provided by the manufacturers.

(Flow Cytometry)

Stained cells were measured using a FACS Calibur (Becton Dickinson), and the obtained data was analyzed using FlowJo software (Tree Star, Ashland, Oreg.). A FACS Aria (Becton Dickinson) was used when cell sorting was necessary.

(ELISA)

The concentration of human galectin-9 was quantified according to the reported method (Non-Patent Document 34).

The concentration of mouse galectin-9 was quantified according to the reported method (Non-Patent Document 16), in which the following three points were modified for improvement: (1) the anti-mouse galectin-9 antibody used for coating a plate was changed to clone 108A2 (GalPharma); (2) as the antibody for detection, an anti-mouse galectin-9 polyclonal antibody (GalPharma) labeled with biotin was used; and (3) accompanying the change in the antibody for detection, horseradish peroxidase-labeled streptavidin (Endogen) was used instead of the third antibody to cause a color-developing reaction. This system specifically detects mouse galectin-9, and no reaction is caused even if a measurement sample contains stabilized human galectin-9 at a concentration of 30 nM. Mouse or human IL-17A, mouse TNF-α, mouse IL-12, mouse IFN-γ, and mouse IL-13 were detected using appropriate DuoSets (R&D Systems), respectively; mouse IL-10 was detected using a Mouse IL-10 ELISA MAX Standard (Biolegend); anti-mouse SRBC IgM was detected using a Mouse Anti-SRBC IgM ELISA Kit (Life Diagnostics); a mouse total IgM antibody and a mouse total IgG antibody were detected using a Mouse Total IgM ELISA Kit and a Mouse Total IgG ELISA Kit (both available from Bethyl), respectively; and an anti-dsDNA antibody was detected using a Lbis anti-dsDNA-mouse ELISA KIT (Shibayagi Co., Ltd.). These kits were used in accordance with instructions for use provided by the manufacturers.

(Animals)

C57BL/6J mice and MRL/MpJUmmCrj-lpr/lpr mice were purchased from Charles River Laboratories Japan, Inc. (Yokohama, Japan); and galectin-9 knockout mice and mouse galectin-9 transgenic mice of the same line were purchased from GalPharma (Takamatsu, Japan). Lewis rats (LEW/Ssn) were purchased from Japan SLC, Inc. (Hamamatsu, Japan). The mice used in this research were kept under standard conditions in a day-and-night-rhythm of 12 h light and 12 h dark and with free access to food and water, and they received humane care in accordance with the national law and international guidelines. The study protocol was approved by the Animal Care and Use Committee of Kagawa University.

The method for the experiments will be described below.
<Isolation and Culture of Mouse Naïve T Cells>

$CD4^+CD62L^+$ naïve T cells were isolated from spleen cells obtained from 8- to 10-week old male C57BL/6J mice using a $CD4^+CD62L+$ T cell Isolation Kit (Miltenyi Biotec, Bergisch Gladbach, Germany) in accordance with instructions for use provided by the manufacturer. Thus, naïve T cells with a purity of at least 94% were obtained. The thus-obtained naïve T cells were suspended in a RPMI 1640 medium (Sigma-Aldrich, St. Louis, Mo.) containing 10% heat-inactivated fetal bovine serum, penicillin G (10 IU/ml, Sigma-Aldrich), and streptomycin (100 µg/ml, Sigma-Aldrich). The resultant suspension was inoculated into a 96-well plate (Becton Dickinson) coated with an anti-CD3 antibody (1 µg/ml) at a density of $2 \times 10^5$ cells/0.1 ml/well. An anti-CD28 antibody (2 µg/ml, Becton Dickinson) was added to the plate, and thereafter, the naïve T cells were cultured in a $CO_2$ incubator at 37° C. for 72 to 96 hours. For induction of differentiation into $T_H17$ cells, human TGF-β1 (3 ng/ml, R&D systems), mouse IL-2 (5 ng/ml, R&D systems), and mouse IL-6 (20 ng/ml, R&D systems) were added to this system. For induction of differentiation into $T_H1$ cells, mouse IL-12 (10 mg/ml, R&D systems) and anti-IL-4 antibody (10 µg/ml, Becton Dickinson) were added. For induction of differentiation into $T_H2$ cells, mouse IL-4 (20 mg/ml, R&D systems) and anti-IL-12 antibody (10 µg/ml, Becton Dickinson) were added. For Tr1 differentiation, using a 96-well plate coated with an anti-CD3 antibody (10 µg/ml), the naïve T cells were cultured for 3 days in the presence of an anti-CD28 antibody (2 µg/ml) and IL-27 (25 ng/ml). In some of the experiments, the naïve T cells were cultured in the presence of stabilized human galectin-9 (30 nM), lactose (3, 10, or 30 mM), sucrose (3, 10, or 30 mM), an anti-Tim-3 neutralizing antibody (10 µg/ml, eBioscience), or rat IgG2a (10 µg/ml, eBioscience).

<Action of $T_HGAL9$ Cells on Differentiation into $T_H17$ Cells>

CD25 negative $T_HGAL9$ ($CD25^-CD4^+$ T cells expressing galectin-9 on cell surfaces) and non-$T_HGAL9$ cells (cell surface $galectin-9^-/CD25^-/CD4^+$ T cells) were isolated by sorting (cell purity: at least 97%). On the other hand, the naïve T cells were cultured under $T_H17$ differentiation-inducing conditions for 6 hours, thereby committing the naïve T cells to differentiate into $T_H17$. Thereafter, the cultured cells were collected, and mixed with the CD25 negative $T_HGAL9$ cells or the non-$T_HGAL9$ cells at a mixing ratio of 1:1 ($5 \times 10^4$ cells:$5 \times 10^4$ cells). Then, they were cultured for 90 hours under TCR stimulation only. For inhibition of the action of galectin-9, 30 mM lactose was added to the system.

<Isolation and Culture of Human CD4 T Cells>

Peripheral-blood mononuclear cells were isolated by overlaying peripheral blood collected from a healthy subject on a gravity separation solution (LYNIPHOSEPAR, Nakalai Tesque, Kyoto, Japan) and then subjecting them to centrifugation in accordance with instructions for use provided by the manufacturer. From the thus-obtained peripheral-blood mononuclear cells, CD4 T cells were isolated using a $CD4^+$ T Cell Isolation Kit II (Miltenyi Biotec) in accordance with instructions for use provided by the manufacturer. For TCR stimulation of the $CD4^+$ T cells, the cells were cultured in the same manner as in the case of the mouse naïve T cells. Specifically, the $CD4^+$ T cells were suspended in a RPMI 1640 medium containing 10% heat-inactivated fetal bovine serum, penicillin G, and streptomycin, and the resultant suspension was inoculated into a 96-well plate coated with an anti-CD3 antibody (1 µg/ml) at a density of $2 \times 10^5$ cells/0.1 ml/well. An anti-CD28 antibody (2 µg/ml, Becton Dickinson) was added to the plate, and thereafter, the $CD4^+$ T cells were cultured for 96 hours.

To separate human $T_HGAL9$ cells and human non-$T_HGAL9$ cells from the thus-obtained cultured cells, the cells were stained with an anti-human galectin-9-Alexa 488 antibody (clone 9M1-3, GalPharma), and sorted using a FACS Aria. The cell purity after the sorting was at least 97%. The cells were cultured for another 96 hours under the TCR stimulation before applying them to the experiments. Differentiation of the human $CD4^+$ T cells into $T_H17$ cells was induced by the reported method (Non-Patent Document 35). Briefly, the $CD4^+$ T cells were cultured for 9 days in the presence of human IL-2 (5 ng/ml, R&D systems) in addition to the above-described TCR stimulation, and further, in the presence of human IL-1β (50 ng/ml, R&D systems), the combination of the same IL-1β and IL-6, or the combination of the same IL-1β and mouse IL-23 (50 ng/ml, R&D systems).

<Real-Time RT-PCR> mRNA was quantified according to the reported real-time RT-PCR, in which the amplified nucleic acid was stained with SYBR Green I and measured using a ABI PRISM 7000 sequence detector (Applied Biosystems, Foster City, Calif.) (Non-Patent Document 36). Primers were purchased from TAKARA BIO INC. (Otsu, Japan). A specific mRNA expression level was represented as the ratio with respect to the internal standard, which is the mRNA expression level of glyceraldehyde-3-phosphate dehydrogenase (GAPDH) quantified by the same real-time RT-PCR.

<Statistical Analysis>

For statistical analysis of data, analysis software Prism (Graphpad software) was used. The presence or absence of a statistically-significant difference was determined by the nonparametric two-tailed Mann-Whitney test, the Logrank test, the 2-way ANOVA, etc., and p values of less than 0.05 ($p<0.05$) were considered significant. All the numerical values show in bar graphs or line graphs indicate the mean±SEM (n>3).

<Experimental Results and Consideration>
<Stabilized Human Galectin-9 Exhibits Long-Lasting Therapeutic Effect on Rat Arthritis>

Figure 1B:
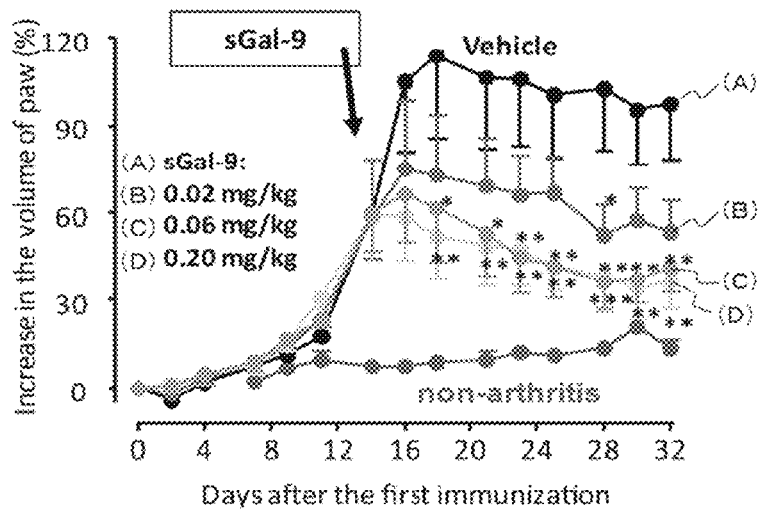
Figure 1C:
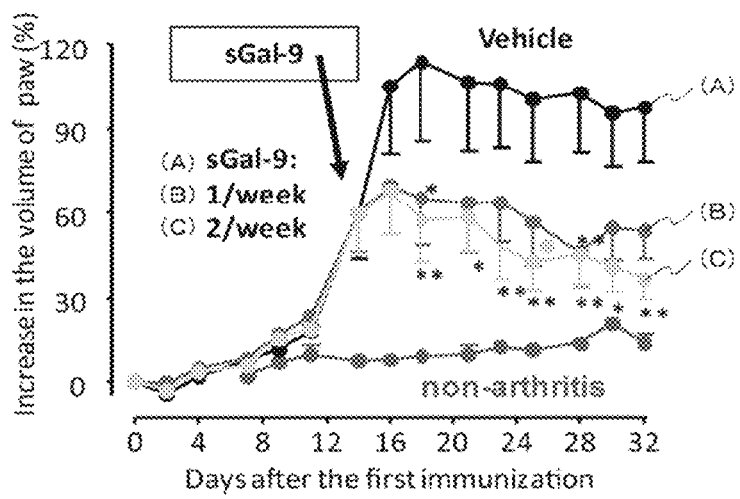

FIG. 1 shows a therapeutic effect of the stabilized human galectin-9 on rat collagen-induced arthritis. A collagen solution used for immunization was prepared at the time of use in the following manner. Bovine Collagen type II (BCII; Collagen Research Center) was mixed with Muramyl dipeptide (MDP; Peptide Institute) so that their concentrations were 1.6 mg/ml and 0.4 mg/ml, respectively. The resultant mixture was mixed with incomplete Freund's adjuvant (IFA; Difco) of the same volume, and then emulsified. 1 ml of this collagen solution was administered intradermally to the back of each Lewis rat (♀, 6- to 7-week old) (day 0). The intradermal administration was carried out in a distributed manner to multiple sites of the back of each rat (at least 10 sites/rat). On day 7 after the administration, a collagen solution prepared in the same manner was administered as a booster to the base of the tail of each rat (0.3 ml/rat). From day 7 after the booster administration, the stabilized galectin-9 was administered subcutaneously at the indicated doses as per the indicated schedule (FIG. 1A). Swelling of paws associated with the onset of the arthritis was measured independently by two observers using a plethysmometer (Muromachi Kikai Co., Ltd). The total volume of both hind paws of each rat was measured over time, and was represented as a change rate (%) on the basis of the initial value. When the stabilized human galectin-9 was administered subcutaneously three times a week in the present model, the already developed swelling of the joints decreased in a dose-dependent manner, and substantially perfect therapeutic effect was achieved at a dose of 0.06 mg/kg (FIG. 1B). Next, with the dose of the stabilized human galectin-9 being fixed to 0.6 mg/kg, the difference in therapeutic effect was compared between the case of the 1 time/week administration and the 2 times/week administration. As a result, the obtained therapeutic effects were substantially the same (FIG. 1C). It is well known that subcutaneous injection can sustain drug efficacy. For example, in the case of an antibody drug, the drug is released into the blood gradually when it is administered subcutaneously. Thus, the drug circulates around the body longer as compared with the case of systemic administration.

<Pharmacokinetics of Stabilized Human Galectin-9 in Subcutaneous Administration>

Thus, the pharmacokinetics of the stabilized galectin-9 in the case of subcutaneous administration was examined. Lewis rats (♀, 6- to 7-week old) were given single subcutaneous administration of the stabilized human galectin-9 at each dose indicated in FIG. 1. Plasma was collected over time (before administration (0 minutes), and 5 minutes, 15 minutes, 30 minutes, 1 hour, 2 hours, 4 hours, 8 hours, 16 hours, 24 hours, 48 hours, and 72 hours after the administration), and the concentration of the stabilized galectin-9 in blood was measured by specific ELISA. As a primary antibody in the ELISA, an anti-human galectin-9 monoclonal antibody 9S2-3 was used. This antibody recognizes the N-terminal carbohydrate recognition domain of galectin-9 and does not react with human galectin-9 denatured with SDS. Hence, it is considered that this antibody recognizes a protein with a correct conformation. As a secondary antibody in the ELISA, an anti-human galectin-9 CT rabbit polyclonal antibody was used. This antibody was prepared by immunizing a rabbit with the C-terminal carbohydrate recognition domain region of human galectin-9, and cross-reactions against other galectins were removed by absorption. Also, the present ELISA does not cross-react with mouse and rat galectins-9. That is to say, the present ELISA can measure complete stabilized human galectin-9 with no decomposition or denaturation.

Based on the concentrations of the stabilized human galectin-9 in blood, pharmacokinetic analysis was carried out according to the moment analysis method using moment analysis software (provided by Kenji Tabata, Fujisawa Pharmaceutical Co., Ltd., Graduate School and Faculty of Pharmaceutical Sciences, Kyoto University). As a result, as can be seen from FIG. 2 and Table 2, the concentrations of the stabilized galectin-9 in blood were very low, and when the stabilized galectin-9 was administered at a dose of 0.6 mg/kg (which is a dose at which a sufficient therapeutic effect was obtained in the arthritis model described above), the maximum concentration thereof in blood was 0.943 ng/ml; $t_{1/2}$ was 7.6 hours; and MRT was 12.5 hours. It has been revealed that, in order to obtain an IL-17 production inhibitory effect of the stabilized galectin-9 in vitro, the concentration of the stabilized galectin-9 needs to be at least 10 nM (about 0.3 µg/ml), and the statistically-significant difference is exhibited when the concentration of the stabilized galectin-9 is 30 nM (about 1 µg/ml) (Non-Patent Document 7). That is, it is unlikely that stabilized human galectin-9 released in blood exhibits a drug efficacy, and it is presumed that stabilized human galectin-9 gives an effect on immune cells while it is present at a relatively high concentration, specifically, while it is at the administration site and it passes through lymphatic vessels or lymph nodes. Also, it was verified by the present experiment and other pharmacokinetic tests that stabilized galectin-9 is eliminated from the body rapidly after the administration. Thus, it is considered that the long-lasting drug efficacy of stabilized galectin-9 is supported by cells on which the stabilized galectin-9 acted within a short time after its administration, and is not obtained by the direct action of the stabilized galectin-9. Although it is obvious that cells that produce and release galectin-9 to regulate immunity are present in vivo as described in the "Background Art" section, identification thereof is very difficult. Identification of a cell that secretes galectin-9 to regulate immunity and the clarification of the details of the action mechanism of galectin-9 are critical goals, and attaining these goals would make particularly significant contributions to medical science and industries.

<Galectin-9 is Endogenous Factor that Inhibits EAE>

FIG. 3 shows a therapeutic effect of galectin-9 on MOG-induced experimental allergic encephalitis (EAE). It is known that the onset of encephalitis in this model occurs in a Th17-dependent manner. (A) The onset of EAE was induced in female C57BL/6J mice (WT) or galectin-9 knockout mice (Gal-9 KO) of the same line. The mice were immunized by subcutaneous administration of 150 µg of MOG (35-55) peptide prepared in CFA containing 300 µg of *Mycobacterium tuberculosis* (H37RA, Difo). On the day of the administration and 2 days after the administration, 200 ng of pertussis toxin (List Biological Laboratory) was administered intravenously to the mice, and clinical scores were recorded over time by visual observation. The clinical scores were determined according to the following criteria.

clinical score 0: no abnormalities
clinical score 1: hypotonicity in tail
clinical score 2: paraparesis of hind paws
clinical score 3: paraplegia of hind paws
clinical score 4: quadriplegia
clinical score 5: nearly dead or dead (B) Spinal cords of the mice at week 20 after the immunization were stained with hematoxylin-eosin and immunostained with an anti-CD3 antibody. In the spinal cords of the galectin-9 knockout mice (Gal-9$^{-/-}$), cell infiltration and tissue destruction were more serious as compared with those in the spinal cords of the wild-type mice (WT). Most of the infiltrated cells were CD3 positive, from which it is speculated that they were T cells.

(C) Spleen cells were prepared from the EAE-immunized wild-type mice (WT) and EAE-immunized galectin-9 knockout mice (Gal-9 KO) at week 20 after the immunization, and non-immunized mice (naïve) of the same week old, and stained with CD4, CD25, IL-17, and Foxp3 antibodies. In the galectin-9 knockout mice, CD4$^+$CD25$^+$IL-17$^+$ cells increased significantly as compared to those in the wild-type mice, whereas CD4$^+$CD25$^+$Foxp3$^+$ cells decreased significantly.

(D) Naïve T cells were prepared from spleen cells of the wild-type mice (WT) and the galectin-9 knockout mice (Gal-9 KO). The naïve T cells were inoculated into a 96-well plate (Becton Dickinson) coated with an anti-CD3 antibody at a density of 2×10$^5$ cells/0.1 ml/well. An anti-CD28 antibody (2 µg/ml, Becton Dickinson) was added to the plate, and thereafter, the naïve T cells were cultured for 96 hours (No skewed). For induction of differentiation into T$_H$17 cells, human TGF-β1 (3 ng/ml, R&D systems), mouse IL-2 (5 ng/ml, R&D systems), and mouse IL-6 (20 ng/ml, R&D systems) were added to this system, and the cultured cells were cultured for another 96 hours under this condition (T$_H$17 skewed). The concentration of IL-17A in each culture supernatant was quantified by ELISA. As a result, the expression of IL-17A was induced markedly by the T$_H$17 differentiation-inducing stimulation, and the induction level was significantly higher in the galectin-9 knockout mice than in the wild-type mice.

(E) After the culture supernatant had been extracted in the above described step, the amount of IL-10 mRNA in the remaining cells was quantified by the real-time RT-PCR. The expression level of the IL-10 mRNA was represented as the ratio with respect to the internal standard, which was the signal of glyceraldehyde-3-phosphate dehydrogenase (GAPDH) measured by the same real-time RT-PCR. The expression level of the IL-10 mRNA was significantly lower in the galectin-9 knockout mice than in the wild-type mice in both the conditions of "No skewed" and "T$_H$17 skewed".

(F) Using the system described in the above (A), the onset of EAE was induced in wild-type female C57BL/6J mice. On day 14 and day 16 after the immunization, the stabilized human galectin-9 was administered subcutaneously to the mice at a dose of 0.3 µg/mouse or 3 µg/mouse. To a control group, PBS was administered. Clinical scores were recorded until day 19 after the immunization. Thereafter, the spinal cords of the mice were stained with hematoxylin-eosin. The stabilized human galectin-9 exhibited a tendency of decreasing the clinical score when it was administered at a dose of 0.3 µg/mouse, and provided statistically significant decrease in the clinical score when it was administered at a dose of 3 µg/mouse (P<0.05, the 2-way ANOVA).

In the galectin-9 knockout mice, symptoms of the experimental allergic encephalitis (EAE) induced with the MOG (33-55) were more serious and lasted longer than in the wild-type mice (FIG. 3A). In the wild-type mice, substantially no infiltration was caused in CD3 positive cell in a localized region at week 20 after the onset of EAE, whereas CD3 positive cell infiltration was apparent in the knockout mice (FIG. 3B). In the spleens of the knockout mice at week 20 after the onset, CD4$^+$CD25$^+$ cells, which produce IL-17, were increased and Foxp3 positive cells were decreased as compared with those in the wild-type mice (FIG. 3C). Furthermore, when differentiation into T$_H$17 was induced in the naïve T cells (CD4$^+$CD62L$^+$CD25$^-$) of the knockout mice, the IL-17 production was increased clearly as compared to that in the wild-type cells (FIG. 3D). On the other hand, the mRNA expression of IL-10 were decreased in the knockout mice (FIG. 3E). Thus, a therapeutic effect of the galectin-9 in the EAE model was then examined. As a result, it was found that, when the galectin-9 was administered subcutaneously twice a week from day 14 after the immunization where the symptoms became prominent, the clinical symptoms and histological findings were improved clearly even if the dose thereof was 0.3 µg (FIG. 3F).

These results demonstrate that galectin-9 adjusts the Th17/Treg balance as an endogenous immunoregulatory factor. Thus, the consequence derived from the previously reported experimental results regarding mouse arthritis (Non-Patent Document 7) was further verified and confirmed in EAE.

<Inhibition of T$_H$17 Cell Differentiation by Galectin-9 does not Depend on Tim3>

FIG. 4 shows an effect of galectin-9 to inhibit T$_H$17 cell differentiation in a Tim3/Gal-9 interaction-independent manner.

(A) CD4$^+$CD62L$^+$ naïve T cells prepared from C57BL/6J mice according to the method described with reference to FIG. 3D were subjected to T$_H$17 cell differentiation-inducing stimulation. The CD4$^+$CD62L$^+$ naïve T cells were cultured in the presence of 30 nM stabilized human galectin-9 or PBS as a control for each period indicated in FIG. 4A with the start of the stimulation being 0 hours. Thereafter, the cells were washed in a medium, and kept being subjected to the T$_H$17 cell differentiation-inducing stimulation. The culture supernatant was extracted 96 hours after the start of the stimulation, and the concentration of IL-17 in the medium was quantified by the above-described ELISA. When the stabilized human galectin-9 was present from 0 to 18 hours after the T$_H$17 cell differentiation induction, T$_H$17 cell differentiation was inhibited markedly. On the other hand, the stabilized human galectin-9 treatment carried out for 24 hours before the differentiation induction was found to be ineffective.

(B) In the cells cultured in the presence of the above-described 30 nM stabilized human galectin-9 during the first 24 hours from the start of the $T_H17$ cell differentiation induction and the cells cultured in the presence of the PBS as a control, the mRNA expressions of IL-17F, IL-21, IL-22, and IL23R were quantified by the real-time RT-PCR. The mRNA expressions of all of them were significantly decreased by the stabilized human galectin-9.

(C) The naïve T cells were cultured for 24 hours under the $T_H17$ differentiation-inducing stimulation ($T_H17$ skewed), and CD4$^+$Tim-3$^+$ cells were measured by flow cytometry. As a control, the naïve T cells were cultured for 24 hours under the condition excluding TGF-β1 and IL-6 from the above-described differentiation inducing-stimulation (No skewed). In either case, the expression of Tim-3 cells was almost undetectable. A test regarding inhibition of $T_H17$ differentiation induction by the stabilized human galectin-9 was carried out under the above-described condition (FIG. 4A: 0-96), and an anti-Tim-3 neutralizing antibody (10 μg/ml, αTim-3) or an isotype control antibody (10 μg/ml, IgG2a) was added while the stabilized human galectin-9 was present. IL-17A in the supernatant obtained after 96 hours of culture was quantified by ELISA. As a result, the anti-Tim-3 antibody did not inhibit the action of the stabilized human galectin-9.

(D) The naïve T cells were cultured for 96 hours under the $T_H17$ differentiation-inducing stimulation. Thereafter, the stabilized human galectin-9 (30 nM) was added to a cell population containing differentiated $T_H17$ cells. 4 hours later, Tim-3 positive cells, i.e., $T_H17$ cells, having undergone apoptosis were detected by flow cytometry. Also, the same experiment was carried out under the condition where an anti-Tim-3 antibody (10 μg/ml, αTim-3) or an isotype control antibody (10 μg/ml, IgG2a) was added together with the stabilized human galectin-9. The stabilized human galectin-9 induced apoptosis of the $T_H17$ cells, and the effect thereof was significantly inhibited by the anti-Tim-3 antibody. This result suggests that galectin-9 induces apoptosis of differentiated $T_H17$ cells in a Tim-3-dependent manner.

IL-17 production is induced strongly when the naïve T cells were cultured for 4 days in a plate coated with an anti-CD3 antibody under the stimulation with an anti-CD28 antibody, IL-2, TGF-β1, and IL-6. The addition of 30 nM galectin-9 to this $T_H17$ differentiation inducing-system revealed that: when the galectin-9 treatment was performed within 18 hours from the start of the differentiation, the IL-17 production was inhibited markedly; and when the galectin-9 treatment was performed within the first 24 hours from the start of the differentiation, the IL-17 production inhibitory effect obtained was equivalent to that obtained when the galectin-9 treatment was performed throughout the 4 days (FIG. 4A). In contrast, no inhibitory effect was obtained when the galectin-9 treatment was performed 24 hours before the $T_H17$ differentiation induction (FIG. 4A). The mRNA levels of IL-17F, IL-21, IL-22, and IL-23R involved in $T_H17$ differentiation were examined. As a result, when the galectin-9 treatment was performed for 24 hours after the start of the $T_H17$ differentiation, not only the expression of IL-17A but also the expressions of all of these $T_H17$ related genes were inhibited (FIG. 4B), whereby the possibility is suggested that this might be the cause of the inhibition of the $T_H17$ cell differentiation. Galectin-9 is a ligand of Tim-3, and it induces apoptosis through an interaction with a Tim-3-expressing $T_H1$ cell (Non-Patent Document 4). Since it has been reported that $T_H17$ cells express Tim-3 (Non-Patent Documents 5 to 6), the possibility that Tim-3 might be involved in the inhibition of the $T_H17$ differentiation by galectin-9 was examined. However, it was found that 24 hours after the start of the $T_H17$ cell differ-entiation induction where the galectin-9 starts to exhibit a differentiation inhibitory action, Tim-3-expressing cells were almost undetectable (FIG. 4C), and besides, the inhibition of the $T_H17$ differentiation by the galectin-9 was not canceled by the addition of the Tim-3 neutralizing antibody (FIG. 4C). On the other hand, on day 4 after the differentiation induction, 5% to 10% of the T cells expressed Tim-3. The galectin-9 induced apoptosis in these $T_H17$ cells, and the anti-Tim-3 neutralizing antibody significantly inhibited this effect of the galectin-9 (FIG. 4D). These results strongly suggest that Tim-3 is not involved in the inhibition of $T_H17$ cell differentiation by galectin-9, but is involved in the induction of apoptosis of activated $T_H17$ cells expressing Tim-3.

<O-Linked Carbohydrate Chain is Involved in Inhibition of $T_H17$ Differentiation Induction by Galectin-9>

FIG. 5 shows the results suggesting that not the N-linked carbohydrate chain but the O-linked carbohydrate chain is involved in the inhibition of $T_H17$ differentiation induction by galectin-9.

(A) Naïve T cells were cultured under $T_H17$ differentiation-inducing stimulation, and stabilized human galectin-9 (30 nM) or PBS as a control was added within the first 24 hours. During the first 24 hours, lactose (an inhibitor of galectin) was added at a concentration of 3 mM, 10 mM, or 30 mM, and 96 hours later, and the concentration of IL-17A in the culture supernatant was quantified. As a control of the lactose, sucrose, which does not act on galectin-9, was used. The inhibitory action of the stabilized human galectin-9 was eliminated by the lactose in a concentration-dependent manner. This demonstrates that the lectin activity of stabilized human galectin-9 is necessary for inhibition of $T_H17$ differentiation.

(B) Under the same conditions as described in the above (A), swainsonine (2 μg/ml) as an N-glycosylation inhibitor or Benzyl N-acetyl-α-D-galactosaminide (Benzyl-α-GalNAc, 2 mM) as an O-glycosylation inhibitor was added instead of the lactose. 96 hours later, the concentration of IL-17A in the culture supernatant was quantified. As a result, in the case where the swainsonine was added, the effect of the stabilized human galectin-9 remained significantly, but in the case where the Benzyl-α-GalNAc was used, the significant difference in the effect of the stabilized human galectin-9 was no longer observed. This result implies that a glycoprotein having undergone O-glycosylation is involved in the $T_H17$ differentiation inhibition by galectin-9.

Figure 5A:
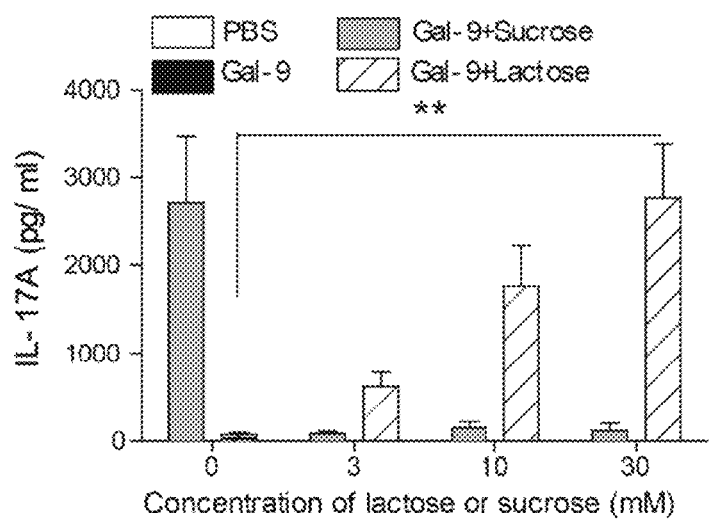
FIG. 5A shows the results of a $T_H17$ differentiation induction assay carried out in the presence of stabilized human galectin-9 and lactose (galectin inhibitor) at each concentration indicated in FIG. 5A. Sucrose was used as a control of lactose. The horizontal axis indicates the concentration of the lactose or sucrose, and the vertical axis indicates the concentration of IL-17A.
Figure 5B:
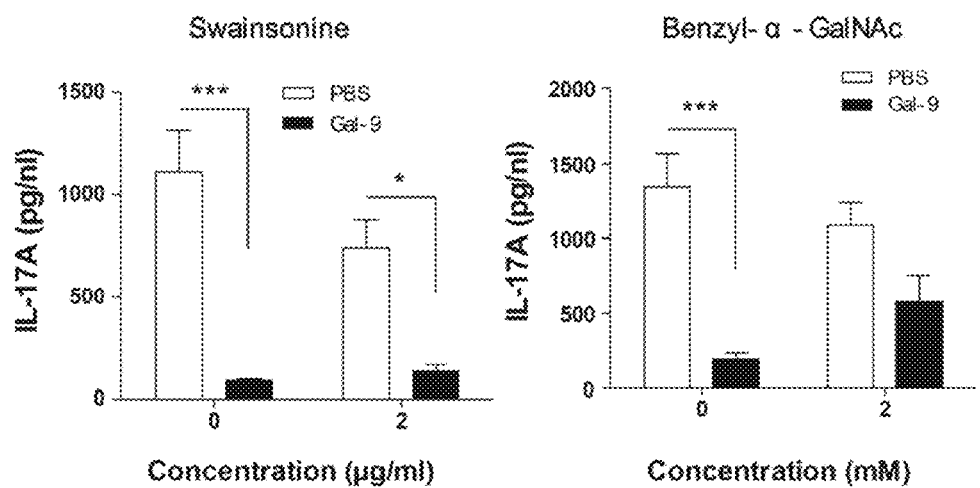
FIG. 5B is a graph showing the results obtained when the $T_H17$ differentiation induction assay described in the above (A) was carried out in the presence of swainsonine (2 μg/ml) as an N-glycosylation inhibitor or Benzyl N-acetyl-α-D-galactosaminide (Benzyl-α-GalNAc, 2 mM) as an O-glycosylation inhibitor. The horizontal axis indicates the concentration of swainsonine or Benzyl-α-GalNAc, and the vertical axis indicates the concentration of IL-17A.

Inhibition of $T_H17$ cell differentiation by galectin-9 was examined in the presence of lactose, which is a low-molecular ligand of galectin-9. As a result, the $T_H17$ differentiation inhibitory effect of the galectin-9 decreased in a manner dependent on the concentration of the lactose added, whereas sucrose, which does not bind to galectin-9, had no effect on this inhibitory effect (FIG. 5A). This result suggests that the lectin activity of galectin-9 is necessary for the inhibition of $T_H17$ differentiation, and the galectin-9 acts on a target cell by binding to polysaccharides expressed by the target cell. Thus, in order to clarify which of O-glycan and N-glycan is the target of galectin-9, Benzyl-α-GalNAc as an O-glycan inhibitor and swainsonine as an N-glycan inhibitor were used. As a result, the $T_H17$ differentiation inhibitory activity of the galectin-9 was inhibited significantly by the Benzyl-α-GalNAcniyotte (FIG. 5B). It is already known that N-glycan plays an important role in apoptosis induction by galectin-9 (Non-Patent Documents 4 and 37). However, the result implies that O-glycan plays an important role in inhibition of $T_H17$ cell differentiation.

<Action of Galectin-9 on Differentiation into $T_H1$, $T_H2$, and $T_H17$ Cells>

FIG. 6 shows an effect of Gal-9 on differentiation into $T_H1$, $T_H2$, and $T_H17$ cells.

(A) 30 nM stabilized human galectin-9 (or PBS as a control) was added to naïve T cells. The naïve T cells were cultured for 96 hours under stimulation inducing differentiation into each of $T_H1$, $T_H2$, or $T_H17$, or under only TCR stimulation by an anti-CD3 antibody and an anti-CD28 antibody (No skewed). Thereafter, the expression of mRNA specific to each $T_H$ subtype was quantified by the real-time RT-PCR. The stabilized human galectin-9 did not give any effect on the expressions of the mRNAs specific to $T_H1$ and $T_H2$ cells, whereas it significantly inhibited mRNA expressions of IL-17A and RORγt specific to $T_H17$ cells only.

(B) mRNAs of IFN-γ and IL-4 under the $T_H17$ differentiation-inducing conditions in the above-described experiment were measured, which revealed that the expressions of both the IFN-γ and IL-4 mRNAs were not changed by the stabilized human galectin-9. Although it is known that $T_H17$ differentiation is inhibited by these cytokines, the above result suggests that the effect of galectin-9 is not for increasing the expressions of these cytokines.

Figure 6A:
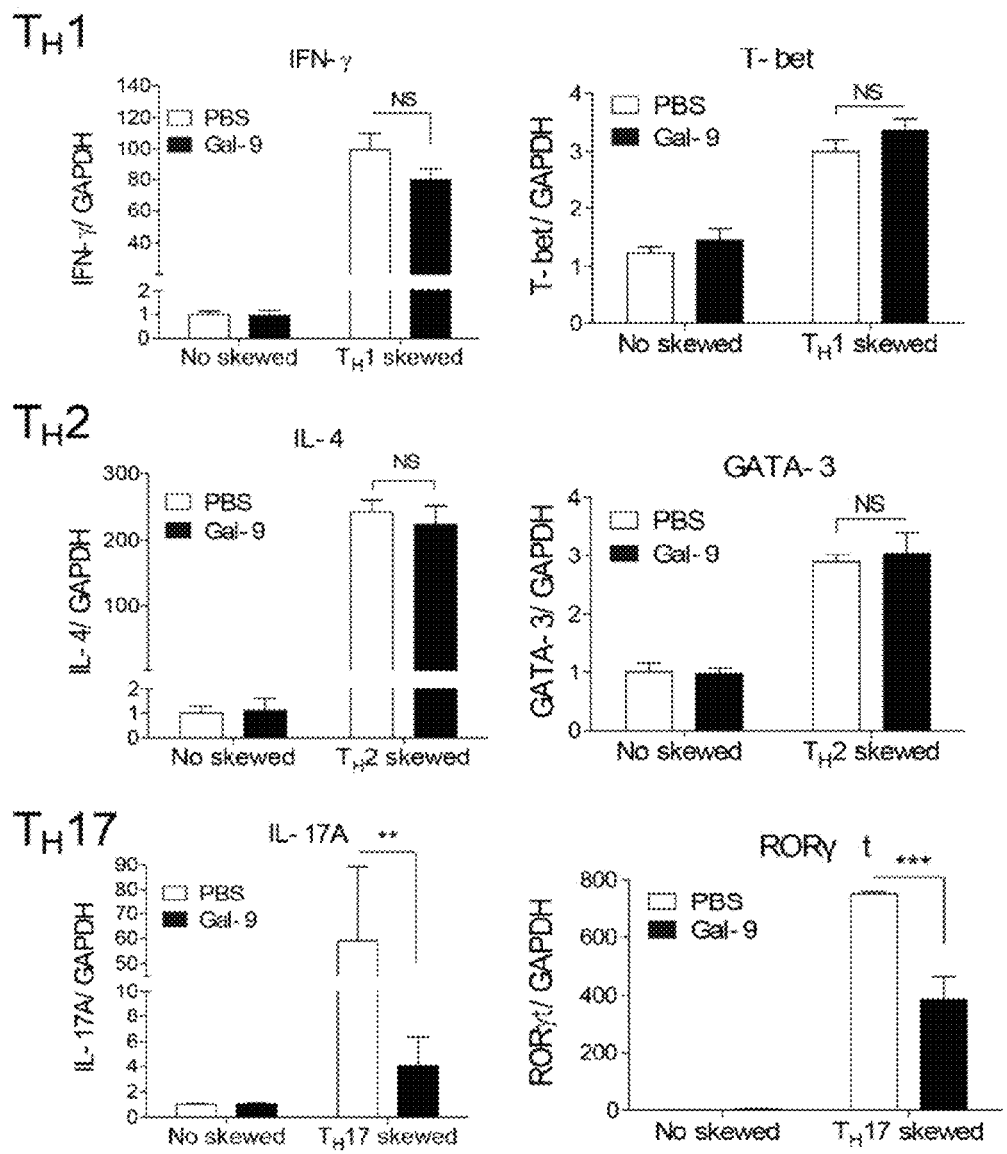
FIG. 6A show graphs showing the results of quantifying the differentiations into the respective cells based on the mRNA expressions specific to the respective Tx subtypes. In the graphs of FIG. 6A, "No skewed" indicates the results obtained when only TCR stimulation was used. (B) FIG. 6B show graphs showing the mRNA expressions of IFN-γ and IL-4 in the cells having undergone the $T_H17$ differentiation induction in the presence of the stabilized galectin-9 in the above (A).
Figure 6B:
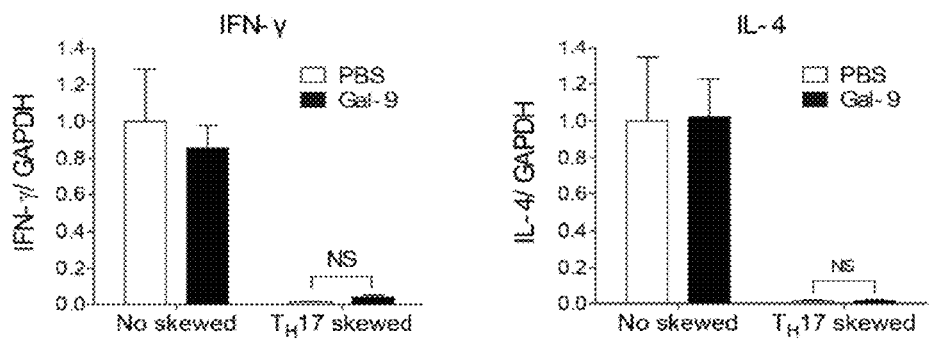
FIG. 6 show graphs showing the results of measuring the effect of Gal-9 on $T_H1$, $T_H2$, and $T_H17$ cell differentiation in still another example of the present invention. (A) Stabilized human galectin-9 (or PBS as a control) was added to an assay system for inducing the differentiation of naïve T cells into $T_H1$, $T_H2$, or $T_H17$ cells.

It was found that the inhibition of helper T-cell differentiation by galectin-9 is specific to $T_H17$ cells, and is ineffective against $T_H1$ cell differentiation by IL-12 and against $T_H2$ cell differentiation by IL-4. Also, regarding the expressions of transcription factors specific to the differentiation of each of $T_H1$, $T_H2$, and $T_H17$, galectin-9 could inhibit only the transcription factor RORγ of $T_H17$ (FIG. 6A). It is known that, when the differentiation into $T_H1$ or $T_H2$ is enhanced, the differentiation into $T_H17$ cells is inhibited (Non-Patent Document 38). However, in the $T_H17$ differentiation inducing-system containing galectin-9, mRNAs of IFN-γ and IL-4 were not enhanced, so that the enhancement of $T_H1$ and $T_H2$ was removed from possible causes (FIG. 6B).

<Galectin-9 Inhibits IL-17 Production in IL-2 Dependent Manner and Enhances Expressions of CD25 and Foxp3>

FIG. 7 shows the results demonstrating that increase in expressions of CD25 and Foxp3 by galectin-9 depend on IL-2.

(A) 30 nM stabilized human galectin-9 (or PBS as a control) was added to naïve T cells, which were then cultured for 24 hours under the $T_H17$ differentiation-inducing condition. By the addition of the stabilized human galectin-9, the proportion of CD4$^+$CD25$^+$ cells was increased significantly. This also was reflected in the increase in mRNA of CD25.

(B) After the naïve T cells were cultured for 96 hours under the condition described in the above (A), the proportion of CD4$^+$CD25$^+$Foxp3$^+$ cells was examined. As a result, the proportion of the CD4$^+$CD25$^+$Foxp3$^+$ cells was increased significantly by the addition of the stabilized galectin-9.

(C) 30 nM stabilized human galectin-9 (control: PBS) and IL-2 at each concentration indicated in FIG. 7C were added to naïve T cells, which were then cultured for 96 hours under the $T_H17$ differentiation-inducing condition. Thereafter, the concentration of IL-17A in each culture supernatant was quantified. The galectin-9 exhibited an IL-17A production inhibitory action only in the presence of IL-2. On the other hand, IL-2 independently exhibited a tendency of inhibiting IL-17A production. However, this inhibitory action was weak, and no statistically-significant difference was observed even when the concentration of IL-2 was 100 ng/ml.

(D) The proportion of Treg cells in the cells cultured for 96 hours under the condition described in the above (C) was measured. The stabilized galectin-9 increased CD4$^+$CD25$^+$Foxp3$^+$ cells, i.e., Treg cells, only in when IL-2 was added.

(E) 30 nM stabilized human galectin-9 (control: PBS) was added to naïve T cells, which were then cultured for 96 hours under the $T_H17$ differentiation-inducing condition. Thereafter, they were cultured for another 6 hours in the presence of PMA (50 ng/ml), ionomycin (1 μg/ml), and brefeldin A (10 μg/ml). The proportions of IL-17$^+$Foxp3$^-$ cells and IL-17$^-$Foxp3$^+$ cells in the CD4 positive cells were measured by flow cytometry. As a result, the galectin-9 induced decrease in IL-17$^+$Foxp3$^-$ cells and increase in IL-17-Foxp3$^+$ cells.

(F) Naïve T cells were cultured under the condition described in the above (E), and mRNA expressions of CD25 and Foxp3 at each time point indicated in FIG. 7F were quantified by the real-time RT-PCR. The CD25 expression started to increase from 24 hours after the start of the $T_H17$ differentiation-inducing stimulation, whereas it took 72 hours until the Foxp3 expression started to increase. The mRNA expressions of both CD25 and Foxp3 were increased significantly by the addition of the stabilized galectin-9.

The galectin-9 increased the CD4$^+$CD25$^+$ cells and the mRNA level of CD25 under the $T_H17$ cell differentiation-inducing condition (FIG. 7A), and increased the CD4$^+$CD25$^+$Foxp3$^+$ cells even under the $T_H17$ cell differentiation condition (FIG. 7B). This suggests galectin-9 has a potent Treg cell differentiation-inducing action. It has been reported that IL-2 as a CD25 ligand inhibits the $T_H17$ cell differentiation (Non-Patent Document 39). Also in the system for inducing the $T_H17$ cell differentiation actually used in the present example, IL-17 production was inhibited by IL-2 in a concentration-dependent manner. However, the effect of IL-2 alone was weak (FIG. 7C), and was enhanced synergistically by the addition of the galectin-9 (FIG. 7C). The enhancement of Foxp3 expression by the galectin-9 was induced only in the presence of IL-2 (FIG. 7D). By inducing the $T_H17$ cell differentiation, about 7% of the CD25 positive CD4 cells became Foxp3$^-$IL-17A$^+$ cells, and about 25% of the same became Foxp3$^+$IL-17A$^-$ cells. By the addition of the galectin-9, the proportion of the CD25 positive CD4 cells that became Foxp3$^-$IL-17A$^+$ cells decreased to about 2%, and the proportion of the CD25 positive CD4 cells that became Foxp3$^+$IL-17A$^-$ cells increased to about 50% (FIG. 7E). The CD25 expression in this system was enhanced from 24 hours after the induction of the differentiation, whereas it took 72 hours until the Foxp3 expression was enhanced. The expression levels of both CD25 and Foxp3 were increased by the galectin-9 (FIG. 7F).

<Identification of Cell Surface Gal-9 Positive Cells>

FIG. 8 shows the results of identifying $T_H$ cells that expresses galectin-9 on cell surfaces.

(A) Naïve T cells were cultured for 96 hours under the respective conditions described above in connection with FIG. 6A and without stimulation (No stim), and the concentration of galectin-9 in each culture supernatant was quantified by ELISA. Galectin-9 secretion increased when the cells were cultured under TCR stimulation (No skewed) only and under the conditions for inducing the differentiation into $T_H1$ and $T_H2$ cells, but was inhibited under the condition for inducing the differentiation into $T_H17$.

(B) The system for inducing the differentiation of the naïve T cells into $T_H17$ contained IL-2, TGF-β1, and IL-6, in addition to TCR stimulation. This complete system ($T_H17$ skewed) was modified as follows, and naïve T cells were cultured for 96 hours under each of the following conditions: the condition excluding IL-6 from the complete system (TGF-β1 alone); the condition excluding TGF-β1 from the complete system (IL-6 alone), and TCR stimulation only (No skewed). Thereafter, the galectin-9 contained in each supernatant was quantified by ELISA. By the addition of IL-6, the concentration of the galectin-9 was decreased markedly. On the other hand, TGF-β1 added to the system also exhibited a tendency of decreasing the concentration of the galectin-9, but did not provide any significant difference. (C) 30 nM stabilized human galectin-9 (or PBS as a control) was added to naïve T cells, which were then cultured for 96 hours under each of the following conditions: without stimulation (No stim); TCR stimulation only (No skewed); and Tx 17 differentiation-inducing stimulation. Thereafter, the galectin-9 in the supernatant was quantified by ELISA. This ELISA was specific to mouse galectin-9, and was not interfere with the 30 nM stabilized human galectin-9 added. The stabilized human galectin-9 increased galectin-9 secretion from the naïve T cells cultured under these conditions.

(D) Using the cells described in the above (C), the amount of galectin-9 mRNA was quantified by the real-time RT-PCR. As a result, no statistically-significant difference was observed among the cells cultured under the respective conditions shown in FIG. 8D.

(E) On the other hand, the cell surface galectin-9 and CD25 in the cells described in the above (A) were stained, and measured by flow cytometry. As a result, the proportion of the cells expressing galectin-9 on cell surfaces was a little less than 2% of the CD4 positive cells under the unstimulated condition, and increased to about 4% under the $T_H1$, $T_H2$ differentiation inducing-stimulation or TCR stimulation. In contrast, the proportion of the same remained a little less than 2% under the $T_H17$ differentiation-inducing condition. The proportion of the cell surface galectin-9 positive cells under the respective differentiation stimulations agreed well with the secretion of galectin-9.

(F) The above-described cells were sorted into cell surface galectin-9 positive and cell surface galectin-9 negative cells, and mRNA of the galectin-9 in each cell group was quantified by the real-time RT-PCR. As a result, no statistical difference was observed between these cell groups. After these cells were immobilized and subjected to a treatment for making the cell membranes permeable, they were stained with an anti-galectin-9 antibody so as to stain every galectin-9 contained in the cells. The stained galectin-9 was measured by flow cytometry. Also in this case, no statistical difference was observed between these cell groups.

As revealed by the previous experiments, $T_H17$ differentiation is inhibited strongly by the addition of galectin-9. Also, as already reported, differentiation into $T_H17$ cells is inhibit when cells are cultured under TCR stimulation only or under $T_H1$ and $T_H2$ cell differentiation condition. Thus, the concentrations of galectin-9 in the culture supernatant obtained by culturing the naïve T cells under these conditions were then examined. As a result, the concentration of the galectin-9 was high under the $T_H1$ and $T_H2$ cell differentiation conditions, whereas the galectin-9 was inhibited under the $T_H17$ cell differentiation condition (FIG. 8A). Thus, it was found that TGF-β and IL-6 are necessary for inducing $T_H17$ cell differentiation, and IL-6 inhibits the secretion of galectin-9 (FIG. 8B). As already described above, the addition of recombinant galectin-9 inhibited the $T_H17$ differentiation even under the $T_H17$ cell differentiation condition. This addition of recombinant galectin-9 also enhanced the secretion of endogenous galectin-9 (FIG. 8C). For supplemental information, the added recombinant galectin-9 was human recombinant galectin-9, which also exhibits physiological activity in mouse cells, but is undetectable in the ELISA for measuring the galectin-9 in the culture supernatant. Furthermore, no significant difference was observed between the amount of galectin-9 mRNA obtained under the $T_H17$-inducing condition and under $T_H17$-non-inducing condition, even though the secretion amount of galectin-9 was different between these conditions (FIG. 8D).

Figure 8E:
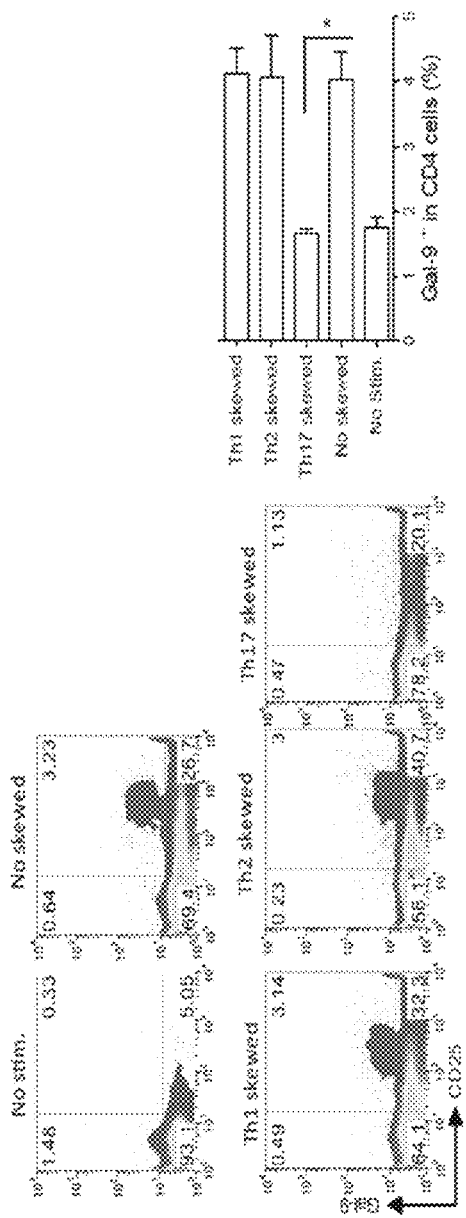
FIG. 8E shows the results obtained when cell surface galectin-9 and CD25 in the cells cultured under the respective conditions in the above (A) were stained and measured by flow cytometry. (F) The cells cultured under the unskewed condition (No skewed) in the above (E) were sorted into cell surface galectin-9 positive (Gal-9$^+$) cells and cell surface galectin-9 negative (Gal-9$^-$) cells.
Figure 8F:
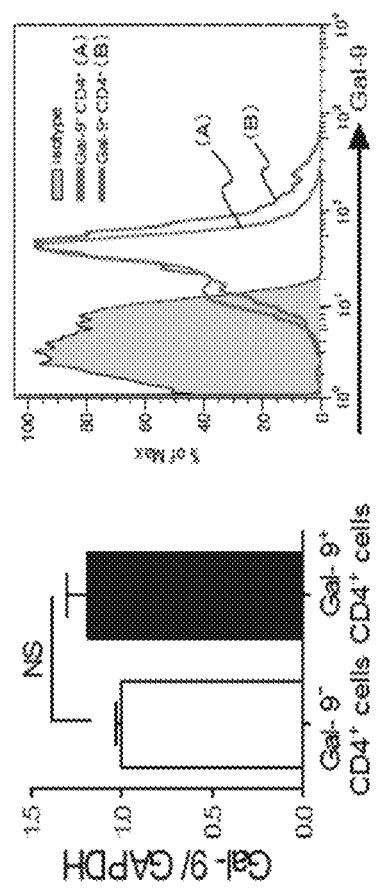
FIG. 8F shows: a graph showing the results of quantifying mRNA of galectin-9 by real-time RT-PCR (the left graph); and a graph showing the results obtained when these cells were immobilized and subjected to a treatment for making the cell membranes permeable and then stained with an anti-galectin-9 antibody to stain every galectin-9 contained in the cells, and the stained galectin-9 was measured by flow cytometry.

From these results, it was found that galectin-9-secreting cells are present in the unskewed system and the $T_H1$ and $T_H2$ differentiation-inducing system. Galectin-9 does not have any signal peptide. The mechanism by which galectin-9 is secreted is totally unknown, but there is no doubt that galectin-9 passes through a cell membrane either directly or via any vehicle from cytoplasm where it is located predominantly. The inventors of the present invention considered that, on cell surfaces of galectin-9-secreting cells, galectin-9 in an intermediate stage of its secretion might be detected. Thus, they stained the galectin-9-secreting cells using an anti-galectin-9 antibody. As a result, the inventors of the present invention successfully detected cell populations expressing galectin-9 on cell surfaces. By the way, this galectin-9 staining was carried out in the presence of lactose. Galectin-9 binds to glycolipids and glycoproteins abundant on cell surfaces. Thus, the staining in the above-described manner was performed in order to discriminate target cells from cells having galectin-9 secondary bound to their cell surfaces after being secreted. As a result of preliminary experiments, it was confirmed that 30 mM lactose completely inhibited the secondary binding of galectin-9 to the cells, whereas it did not interfere with antigen-antibody reactions. Thus, the staining of galectin-9 on cell surfaces was performed always in the presence of 30 mM lactose. A little less than 2% of naïve T cells before being subjected to TCR stimulation expressed galectin-9 on cell surfaces, and as a matter of course, most of them were $CD25^-$ cells (FIG. 8E). By TCR stimulation, $CD25^+$ cells were increased, and at the same time, galectin-9 positive cells also were increased to be about 4% of the $CD25^+$ cell population (FIG. 8E). In contrast, under the $T_H17$ cell differentiation-inducing condition, $CD25^+$ cells and $CD25^+Gal-9^+$ cells were decreased clearly (FIG. 8E). Galectin-9 secretion in the respective Tx cell differentiation systems (FIG. 8A) correlated well with the proportion of the cells expressing galectin-9 on cell surfaces (FIG. 8E), which strongly suggests the possibility that galectin-9-secreting cells might be these cell populations expressing galectin-9 on cell surfaces. Based on the assumption that it is likely that galectin-9-secreting cells express a high level of galectin-9, $CD4^+CD25^+$ T cells were separated and purified by flow cytometry depending on the presence or absence of galectin-9 expression on cell surfaces, and the amount of galectin-9 mRNA in each cell group was examined by the real time RT-PCR. As a result, contrary to the expectation, there was no significantly difference between these cell groups (FIG. 8F). Every galectin-9 present inside and outside of the cells of the respective cell groups was stained using a kit for making cell membranes permeable (BD Cytofix/Cytoperm). As a result, no difference in galectin-9 expression was observed between these cell groups (FIG. 8F). These results agreed well with the results shown in FIG. 8D. However, there arose the necessity of clarifying the relationship between the expression of cell surface galectin-9 and the secretion of galectin-9 through further experiments. Hereinafter, a CD4 T cell expressing galectin-9 on a cell surface tentatively is referred to as $T_HGAL9$.

<Activity of $T_HGAL9$ Cells>

FIG. 9 shows the results demonstrating that: $T_HGAL9$ cells secrete galectin-9 by TCR stimulation and increase the expressions of IL-10 and TGF-β; and $T_HGAL9$ controls the $T_H17/Treg$ balance.

(A) Naïve T cells were prepared from mouse spleen cells, and sorted into cell surface galectin-9 positive cells ($T_H$GAL9 cells: Gal-9$^+$ $T_H$) and cell surface galectin-9 negative cells (non-$T_H$GAL9 cells: Gal-9$^-$ $T_H$). The cells in each cell group were cultured for 96 hours with or without TCR stimulation (an anti-CD28 antibody was added in an anti-CD3 antibody-coated plate), and galectin-9 secreted in each culture supernatant was quantified by ELISA. Galectin-9 secretion was induced by the TCR stimulation only in the $T_H$GAL9 cells.

(B) The mRNA expressions of cytokines in each cell group were examined by the real-time RT-PCR. The $T_H$GAL9 cells exhibited higher expressions of IL-10 and TGF-β than the non-$T_H$GAL9 cells, whereas the $T_H$GAL9 cells exhibited lower expressions of IL-4 and IL-17A than the non-$T_H$GAL9 cells.

(C) The naïve T cells were cultured for 6 hours under $T_H$17 differentiation-inducing stimulation. Then, the cultured cells were mixed with the $T_H$GAL9 cells (Gal-9$^+$ $T_H$) or the non-$T_H$GAL9 cells (Gal-9$^-$ $T_H$) at a mixing ratio of 1:1. Thereafter, they were co-cultured for 90 hours under TCR stimulation only. IL-17A secreted in the culture supernatant was quantified by ELISA. On the other hand, the mRNA expression of Foxp3 was quantified by the real-time RT-PCR. By the addition of the $T_H$GAL9 cells, IL-17A secretion was inhibited, whereas Foxp3 expression was increased.

(D) The above-described co-culture was carried out in the presence of 30 mM lactose (or sucrose as a control) for competitive inhibition of galectin-9. By the addition of the lactose, the inhibition of IL-17A production by the $T_H$GAL9 cells was canceled. This result suggests that, although $T_H$GAL9 cells produce inhibitory cytokines IL-10 and TGF-β, galectin-9 plays an essential role in inhibition of $T_H$17 differentiation.

(E) In order to prove that IL-10 and TGF-β contribute to the $T_H$17 differentiation inhibitory action by $T_H$GAL9 only slightly, neutralizing antibodies against IL-10 and TGF-β were added to the $T_H$17 inhibitory system used in the co-culture of $T_H$GAL9 in the above (C) both at a concentration of 10 μg/ml. As a result, these neutralizing antibodies did not inhibit the action of $T_H$GAL9.

(F) In order to further clarify the contribution of IL-10, recombinant IL-10 was added to the assay system used in the above (C), and the action thereof on the IL-17 production was examined. IL-10 did not exhibit any statistically significant inhibitory effect in the examined concentration range.

The CD4 T cells expressing cell surface galectin-9 found in the experiment described with reference to FIG. 8 were tentatively referred to as $T_H$GAL9 cells, which were assumed to be the cells that secrete galectin-9 and control the $T_H$17/Treg balance. However, the galectin-9 expression in the $T_H$GAL9 cells actually was not significantly higher than those in other T cells (FIG. 8F). In the experiments described with reference to FIG. 9, the $T_H$GAL9 was purified by sorting and the properties thereof were examined, which revealed the fact that the $T_H$GAL9 actually release galectin-9. The $T_H$GAL9 exhibited high expressions of inhibitory cytokines IL-10 and TGF-β, whereas the expressions of IL-4 and IL-17 were significantly low. Furthermore, the fact that $T_H$GAL9 inhibits $T_H$17 and promotes Treg differentiation was verified by the co-culture experiments. IL-10, which is expressed at a high level by $T_H$GAL9, is the most typical inhibitory cytokine, and it has been reported that IL-10 inhibits $T_H$17 differentiation (Non-Patent Document 40). However, the experiments (D, E) using the inhibitors and the experiment (F) using the recombinant IL-10 demonstrated that galectin-9 is a substance chiefly responsible for a drug efficacy for inhibiting the $T_H$17 differentiation induction at least in the assay system used in the experiments described with reference to FIG. 9. By the way, the concentration of galectin-9 secreted by the $T_H$GAL9 in the culture supernatant was about 150 pg/ml in the experimental results shown in FIG. 9A, and this is much lower than the concentration at which the stabilized galectin-9 exhibits a drug efficacy (30 nM: 1 μg/ml). Thus, it is presumed that $T_H$GAL9 in the state of being very close to or in contact with a target cell interacts with the target cell using paracrine or cell surface galectin-9, thereby acting on the target cell. When galectin-9 is present at a high concentration, it induces cell death in many cells. Accordingly, indiscriminate galectin-9 secretion would be dangerous, so that it is presumed that $T_H$GAL9 recognizes a target cell upon contact therewith and then exhibits the controlling actions by galectin-9.

Figure 10A:
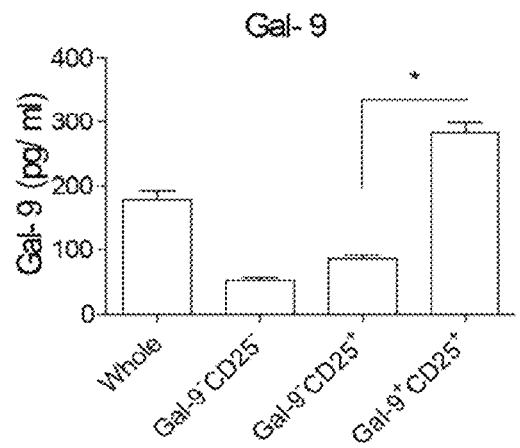
FIG. 10A shows the results of quantifying the concentration of galectin-9 in each culture supernatant by ELISA. (B)
Figure 10B:
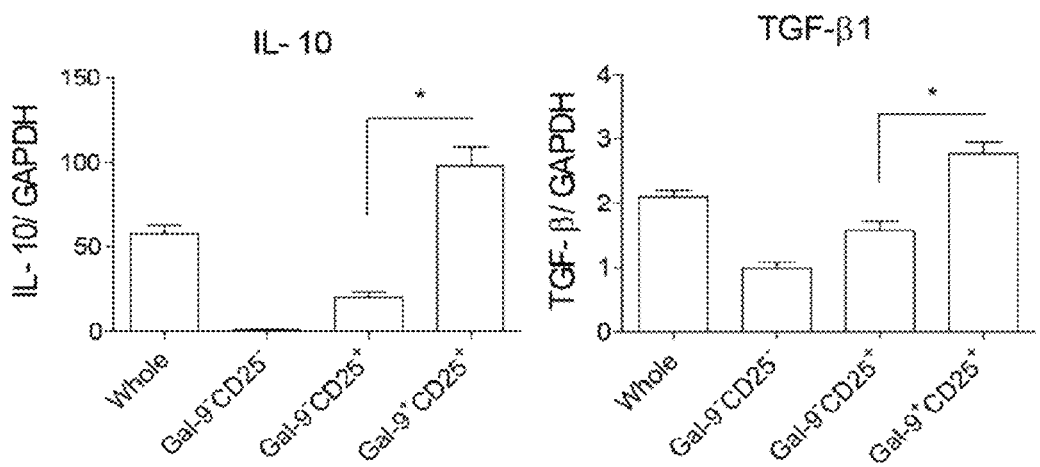
FIG. 10B shows the results of quantifying the expressions of IL-10 and TGF-β1 in each cell group described in the above (A) by real-time RT-PCR.

FIG. 10 shows the results demonstrating that CD25$^+$ $T_H$GAL9 produces IL-10 and TGF-β1 by TCR stimulation.
(A) Naïve CD4 T cells were cultured for 96 hours under TCR stimulation, and the cultured cells were sorted into CD25$^+$ $T_H$GAL9, CD25$^+$ non-$T_H$GAL9, and CD25$^-$ non-$T_H$GAL9. The cells in each cell group were cultured for another 96 hours under TCR stimulation, and galectin-9 in each culture supernatant was quantified by ELISA.
(B) The expressions of IL-10 and TGF-β1 in the cells described in the above (A) were quantified by the real-time RT-PCR.

As a result, by subjecting the $T_H$GAL9 cells to repetitive TCR stimulation, increase in galectin-9 secretion and increase in mRNA expressions of IL-10 and TGF-β were observed.

<Addition of Stabilized Galectin-9 Increases $T_H$GAL9>
FIG. 11 shows the results demonstrating that $T_H$GAL9 was increased by the addition of the stabilized galectin-9.
(A) FIG. 11A shows the results obtained when CD25 and cell surface galectin-9 in the cells used in the experiment described with reference to FIG. 8C were stained, and measured by flow cytometry. The added stabilized human galectin-9 also acted on unstimulated naïve CD4 T cells, and increased Gal-9$^+$CD25$^-$ cells. $T_H$GAL9 decreased under the $T_H$17 differentiation-inducing condition (FIG. 8E), whereas the proportion of $T_H$GAL9 was increased significantly by the addition of the stabilized galectin-9. Also, by the addition of the stabilized human galectin-9, the proportion of Gal-9$^+$CD25$^-$ cells secreting a large amount of galectin-9 was increased significantly in a TCR stimulation-dependent manner. On the other hand, by the addition of the stabilized galectin-9, the proportion of the Gal-9$^-$CD25$^+$ cells also was increased in a TCR stimulation-dependent manner. This cell population contained Treg, so that it is considered that these results were caused by the Treg differentiation promoting action of galectin-9.
(B) $T_H$GAL9 produces not only galectin-9 but also IL-10 and TGF-β. In order to examine the possibility that these cytokines may be involved in the increase in $T_H$GAL9 by TCR stimulation, naïve CD4 T cells were subjected to TCR stimulation in the presence of an IL-10 neutralizing antibody, an IL-10R neutralizing antibody, or a TGF-β neutralizing antibody, and the emergence of $T_H$GAL9 cells was examined by flow cytometry. The results thereof are shown in FIG. 11B. Neutralization of these cytokines had no effect on the increase in $T_H$GAL9.
(C) It is known that IL-10 promotes the differentiation of Tr1, which is an inhibitory T cell, and there is a possibility that IL-10 may affect the increase in $T_H$GAL9. From the results obtained in the above (B), it is considered that IL-10 contributes only slightly at least to the increase in $T_HGAL9$ by TCR stimulation. Thus, this time, IL-10 (or stabilized human galectin-9 as a control) was added to naïve CD4 T cells, which were then cultured under TCR stimulation, and the emergence of $T_HGAL9$ cells was examined by flow cytometry. As a result, in the system of the present experiment, the increase in $T_HGAL9$ by IL-10 was not observed.

<Comparison Between $T_HGAL9$ Cells and Tr1 Cells>

FIG. 12 shows the results of comparison between $T_HGAL9$ cells and Tr1 cells. IL-10-producing type 1 regulatory T cells (Tr1 cells) regulate immunity in various situations, and the possibility of applying Tr1 cells to treatment of autoimmune diseases and cancers is in discussion. Although some markers are proposed for this Tr1 cell at present, the most distinctive feature of this cell is that it secretes a large amount of IL-10. The $T_HGAL9$ cells discovered by the inventors of the present invention also produce IL-10. Thus, the $T_HGAL9$ cells were compared with the Tr1 cells. The already reported mouse Tr1 cell markers include: LAP (Non-Patent Document 21); NKG2D (Non-Patent Document 20); LAG-3 (Non-Patent Document 22); and CTLA-4 (Non-Patent Document 41). Furthermore, it is considered that Tr1 cells do not express Foxp3, as opposed to Treg cells (Non-Patent Documents 42 to 43). Thus, the expressions of Tr1 cell markers were examined before and after TCR stimulation of naïve CD4⁺ T cells.

(A) The reported Tr1 cell markers, namely, LAP, NKG2D, LAG-3, and CTLA-4 of naïve CD4⁺ T cells were stained so as to examine the association with $T_HGAL9$ cells by flow cytometry. $CD25^- T_HGAL9$ cells expressed all of these Tr1 cell markers, whereas $CD25^-$ non-$T_HGAL9$ cells expressed none of them.

(B) These cells were subjected to TCR stimulation, and the same measurement was performed with respect to the T cell population found to be CD25 positive. As a result, nearly all the CD25 positive CD4 cells expressed the Tr1 markers. For the Foxp3 staining, naäve CD4⁺ T cells cultured in the presence of TGF-β1 and IL-2 in addition to the TCR stimulation were used.

(C) FIG. 12C shows the results of staining cell surface galectin-9 and Tim-3 of the cells described in the above (B), which revealed that $T_HGAL9$ did not express Tim-3.

(D, E, F) Naïve CD4⁺ T cells were subjected to TCR stimulation in the presence or absence of IL-27 (25 ng/ml), and cultured for 3 days to promote induction of differentiation into Tr1. Part of the culture supernatant after 3 days of culture was collected, and the concentration of IL-10 (FIG. 12D) and the concentration of galectin-9 (FIG. 12E) were quantified by ELISA. The remaining cells were stimulated with PMA (50 ng/ml) and ionomycin (1 µg/ml) for 4 hours in the presence of brefeldin A (10 µg/ml). Thereafter, IL-10 inside the cells and galectin-9 on cell surfaces were stained and measured by flow cytometry (FIG. 12F).

Figure 12A:
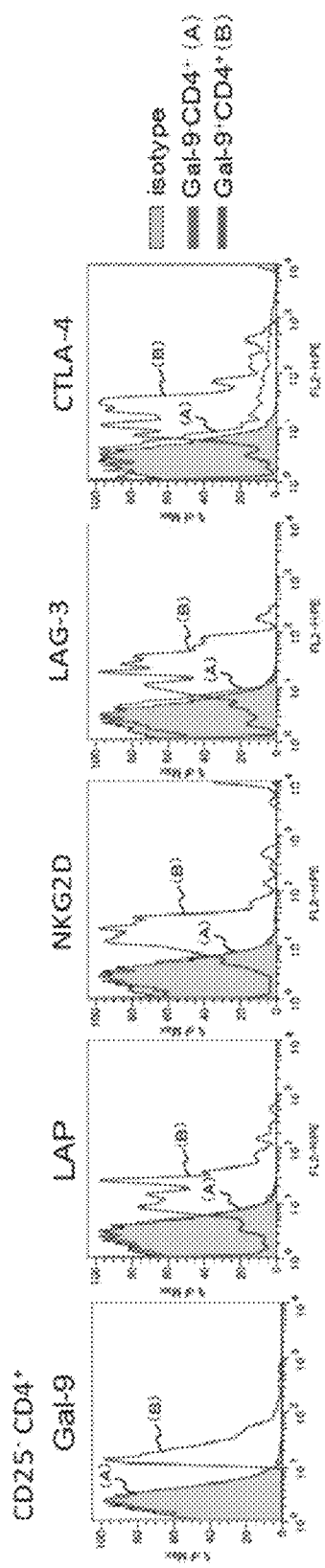
FIG. 12A shows the results of examining them by flow cytometry. (B) Naïve CD4$^+$ T cells were subjected to TCR stimulation, and the T cell population found to be CD25 positive was subjected to the same cell straining as in the above (A) and Foxp3 staining.
Figure 12B:
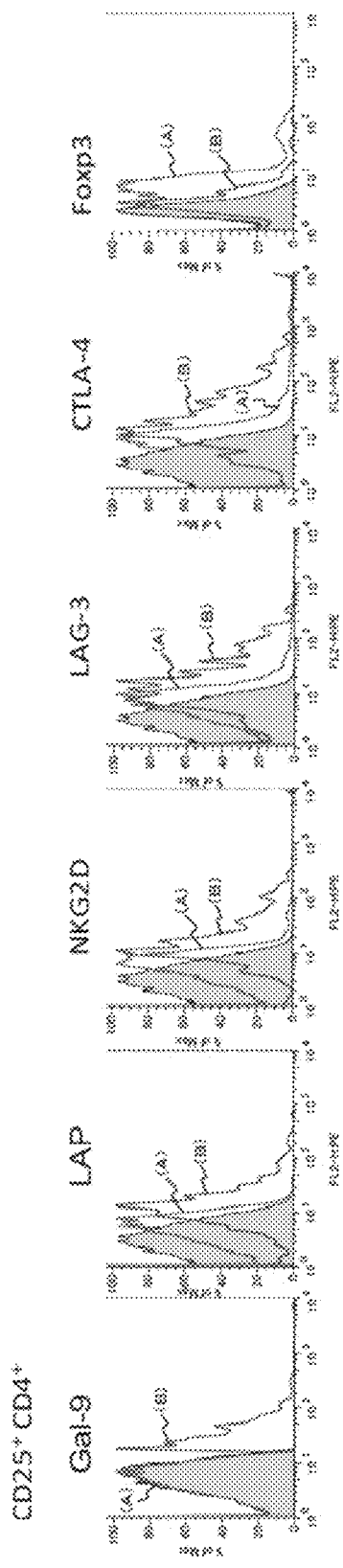
FIG. 12B shows the results of examining them by flow cytometry. (C)

The $CD25^- T_HGAL9$ cells before being subjected to the TCR stimulation expressed all the known Tr1 cell markers, but the expressions of these markers were not observed in the $CD25^-CD4^+$non-$T_HGAL9$ cells expressing no galectin-9 on cell surfaces (FIG. 12A). This result demonstrates that $T_HGAL9$ and Tr1 are very similar cells. On the other hand, in the cells induced to express CD25 by the TCR stimulation, most of the cells expressed the above-described Tr1 cell markers, though their expression levels were different from one another (FIG. 12B). These markers, reported originally as Tr1 markers, also are cell activation markers. Hence, it seems rather natural that the expressions of these markers (though the expression levels varied among the markers) were observed in the TCR-stimulated cells. The $T_HGAL9$ cells did not express Foxp3, whereby it was confirmed that the $T_HGAL9$ cells were different from Treg cells (FIG. 12B). Also, in the $T_HGAL9$ cells, the expression of Tim-3 was not observed (FIG. 12C). $T_HGAL9$ and Tr1 have similar properties, and this suggests the possibility that $T_HGAL9$ may be the same as Tr1 or belongs to a subgroup of Tr1. Thus, this time, naïve T cells were cultured for 3 days under TCR stimulation in the presence of IL-27 as one of Tr1 differentiation factors. As a result, it was found that, by the addition of IL-27, secretions of IL-10 and galectin-9 were increased significantly (FIGS. 12D and 12E). Furthermore, the cells having undergone the differentiation induction were separated into two groups, i.e., a cell surface galectin-9 positive group and a cell surface galectin-9 negative group, and the IL-10 expression levels in the respective groups were compared with each other. As a result, about 50% of the galectin-9 positive-cell population expressed IL-10, whereas 20% or less of the galectin-9 negative cell population expressed IL-10 (FIG. 12F). This result demonstrates that $T_HGAL9$ is a call having very similar properties to Tr1. Indeed, $T_HGAL9$ satisfies the current definition of Tr1, and in that sense, it can be said that $T_HGAL9$ is a subgroup of Tr1. Heretofore, it has been considered that many of the immune regulatory activities of Tr1 depend on IL-10. However, as shown in FIG. 9, not IL-10 but galectin-9 is essential in the control of $T_H17$/Treg balance. By the way, some of the reported Tr1-inducing methods use a high concentration of IL-10, and these methods require a few weeks of cell culturing. In the examination of the increase in $T_HGAL9$ by IL-10 in the experiment described with reference to FIG. 11C, the culture time was 96 hours. Thus, there is a possibility that the culture time in this experiment might be too short to allow IL-10 to exhibit an effect.

Thus, in order to further clarity the relationship between $T_HGAL9$ and Tr1, cells carrying Tr1 markers were examined in galectin-9 knockout mice, and the results thereof are shown in FIG. 13.

Figure 13A:
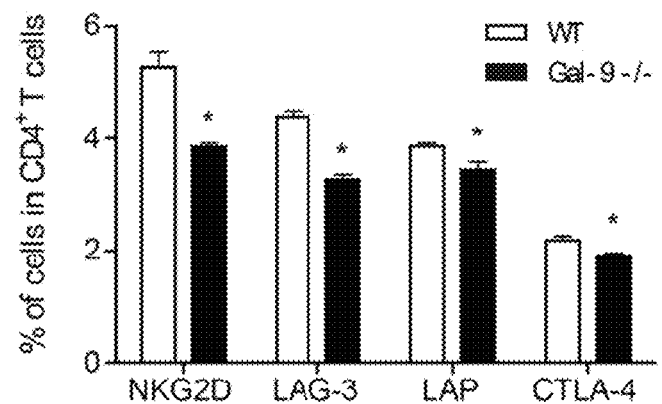
FIG. 13A shows the results of measuring the expressions of CD4, NKG2D, LAG-3, LAP, and CTLA-4 in spleen cells of the galectin-9 knockout mice and the wild-type mice by flow cytometry. (B) Naïve CD4 T cells of the galectin-9 knockout mice and the wild-type mice were cultured under TCR stimulation only (No skewed) or under $T_H17$ differentiation-inducing stimulation (Th17 skewed).

(A) FIG. 13A shows the results obtained when CD4 and NKG2D, LAG-3, LAP, or CTLA-4 in spleen cells of galectin-9 knockout mice and wild-type mice were stained and measured by flow cytometry. In the galectin-9 knockout mice, the proportions of the cells positive for the respective Tr1 markers were decreased as compared to those in the wild-type mice.

Figure 13B:
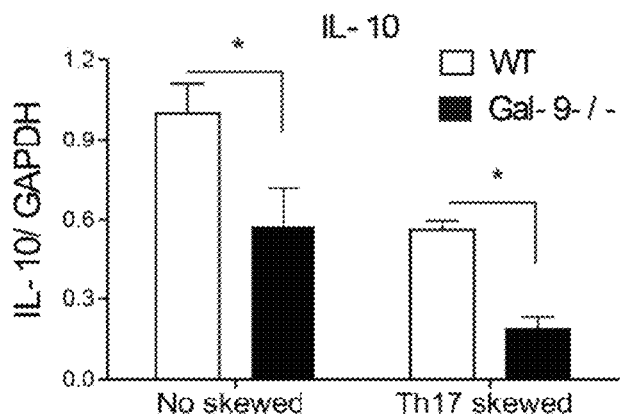
FIG. 13B shows the results of examining the mRNA expression of IL-10 by real-time RT-PCR. (C) Cells cultured under the unskewed condition (No skewed) described in the above (B) were treated with PMA and ionomycin in the presence of brefeldin A (10 µg/ml), and IL-10 that had accumulated inside the cells were stained.

(B) FIG. 13B shows the results obtained when naïve CD4 T cells of galectin-9 knockout mice and wild-type mice were cultured under TCR stimulation only (No skewed) or under $T_H17$ differentiation-inducing stimulation (Th17 skewed). The mRNA expression of IL-10 was examined by the real-time RT-PCR. In the galectin-9 knockout mice, the production of IL-10 was decreased significantly.

Figure 13C:
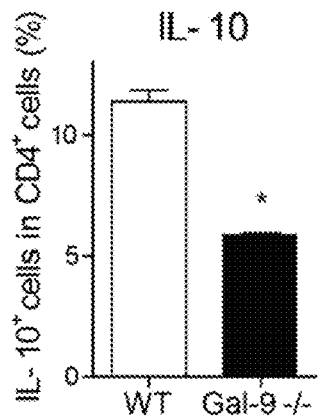
FIG. 13C shows the results of measuring IL-10 by flow cytometry.

(C) FIG. 13C shows the results obtained when the cells cultured under the unskewed condition (No skewed) in the experiment described in the above (B) were treated with PMA (50 ng/ml) and ionomycin (1 µg/ml) for 4 hours in the presence of brefeldin A (10 µg/ml), after which IL-10 having accumulated inside the cells was stained and measured by flow cytometry. In the galectin-9 knockout mice, the IL-10 positive cells were decreased significantly.

These results all demonstrate that $T_HGAL9$ and Tr1 are very similar cells, and according to the current definition of Tr1, $T_HGAL9$ is the same as Tr1 or a subgroup of Tr1.

Table 1 below shows the results of examining the proportion of cell surface galectin-9 positive cells ($T_HGAL9$) in CD4 positive T cells collected from various organs. In Table 1, "Organs" means the "organs"; "Thymus" means the "thymus"; "LN" means the "lymph node"; "Spleen" means the "spleen"; "Peyer's patch" means the "Peyer's patch"; and "PBMC" means "peripheral blood mononuclear cells". Also, "Phenotype" means the "phenotype", and "cells" means the "cells". In the thymus, a large number of T cells are in an immature state showing double positive for CD4 and CD8, so that only CD4 SP (CD4 single positive) T cells were examined in the present experiment. Also, the presence of $T_H$GAL9 cells was examined in various lymphoid organs. As a result, it was found that about ¼ of the CD4 single positive cells were $T_H$GAL9 cells in the thymus; and about 4%, 7%, 15%, and 7% of $CD4^+CD25^-$ T cells derived from the lymph node, spleen, peripheral blood and Peyer's patch, respectively, were $T_H$GAL9 cells.

TABLE 1

| Organs | Phenotype | % of Gal-9+ CD25− cells | SD |
|---|---|---|---|
| Thymus | in CD4 SP | 24.6 | 0.4 |
| LN | in CD4 | 3.6 | 0.4 |
| Spleen | in CD4 | 6.5 | 0.8 |
| Peyer's patch | in CD4 | 14.8 | 0.7 |
| PBMC | in CD4 | 7.2 | 0.9 |

<Effects of Galectin-9 on Human $T_H$17/Treg Differentiation and Identification of Human $T_H$GAL9 Cells>

It is well known that the immune system of humans is not the same as that of mice. Accordingly, there is no guarantee that galectin-9 functions clarified in this research using mice and mouse cells also apply to humans. Thus, in considering clinical applications of galectin-9, it is essential to verify that: galectin-9 controls the $T_H$17/Treg balance also in humans; and humans also have $T_H$GAL9 cells. FIG. 14 shows the results of examining the effects of galectin-9 on human T cells and identifying $T_H$GAL9 cells.

(A) To peripheral blood $CD4^+$ T cells obtained from four healthy subjects, stabilized human galectin-9 (30 nM) or PBS as a control was added. The cells were cultured under TCR stimulation for 96 hours. CD25 was stained and measured by flow cytometry.

(B) CD25 and Foxp3 of the cells obtained in the above (A) were stained, and the expressions of CD25 and Foxp3 were measured by flow cytometry.

(C) To human $CD4^+$ T cells, stabilized human galectin-9 (30 nM) or PBS as a control was added. The cells were cultured for 9 days under the $T_H$17 differentiation-inducing stimulation. The IL-17 concentration in the culture supernatant was quantified by ELISA.

(D) Human $CD4^+$ T cells were cultured for 96 hours under TCR stimulation or without stimulation. Cell surface galectin-9 and CD25 of the cells were stained, and measured by flow cytometry.

(E) Human $CD4^+$ T cells were cultured for 96 hours under TCR stimulation. The cultured cells were then sorted into cell surface galectin-9 positive cells ($CD25^+$ $T_H$GAL9) and cell surface galectin-9 negative cells (CD25+ non-$T_H$GAL9). The cells in each cell group were cultured for another 96 hours under TCR stimulation. Galectin-9 in each culture supernatant was quantified by ELISA. On the other hand, the mRNA expressions of the respective cytokines indicated in FIG. 14E were measured by the real-time RT-PCR.

Figure 14E:
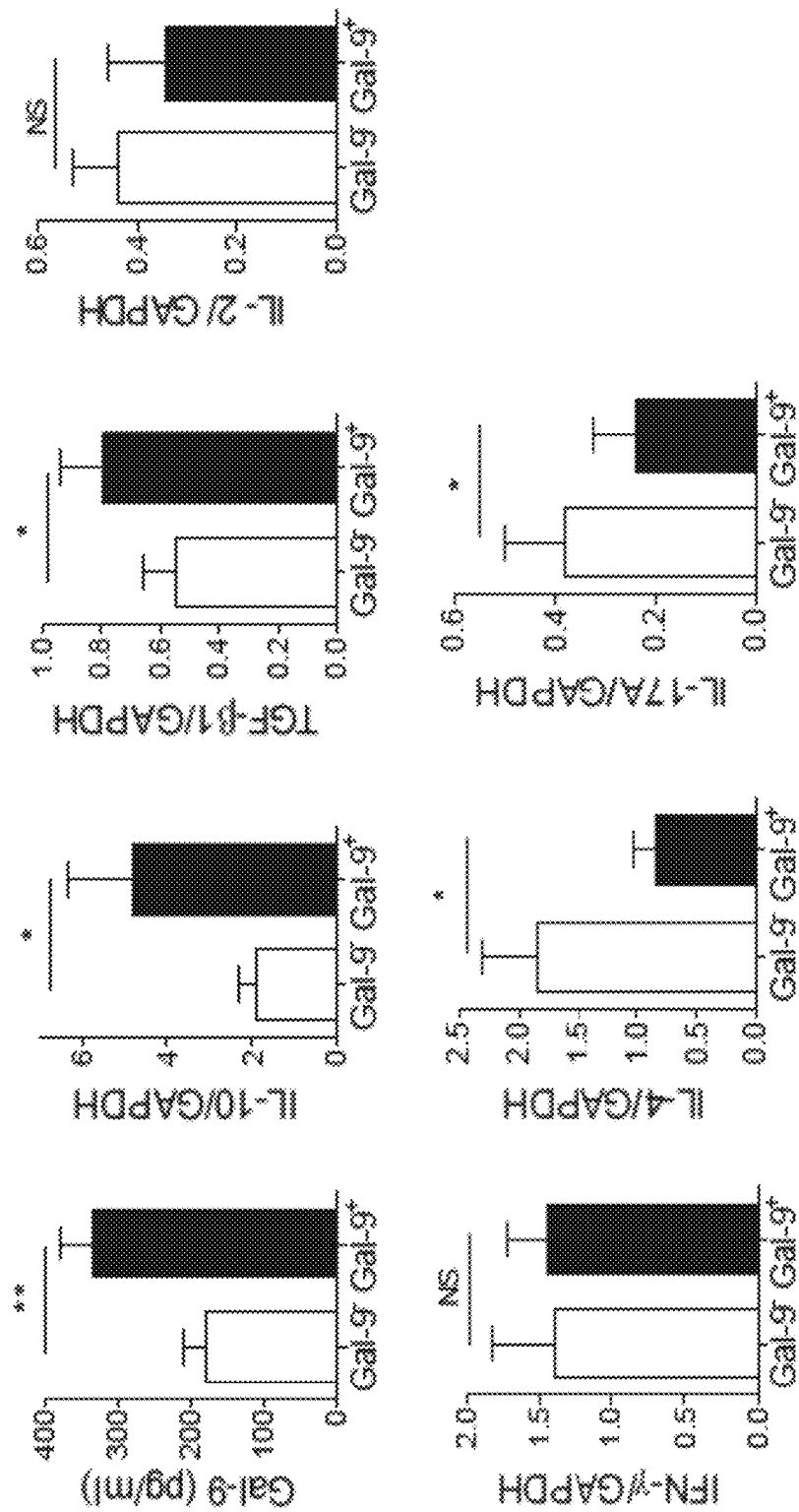
FIG. 14E shows the results of quantifying galectin-9 in the supernatant by ELISA and measuring the mRNA expression of each cytokine by real-time RT-PCR.

When the $CD4^+$ T cells obtained from the human peripheral blood were cultured in the presence of galectin-9, the proportions of the CD25 positive cells and $CD25^+Foxp3^+$ cells were increased by galectin-9, and the increase was further enhanced by TCR stimulation (FIGS. 14A to 14B). Next, galectin-9 was added to the human $T_H$17 differentiation inducing-system, and the $T_H$17 differentiation was examined with the release of IL-17 as an indicator. As a result, IL-17 secretion was inhibited by the galectin-9 (FIG. 14C). These findings are the same as those obtained regarding the galectin-9 functions clarified using the mouse cells. Also, the peripheral bloods of the healthy subjects contained 1% to 4% $CD4^+CD25^-$ T cells expressing galectin-9 on cell surfaces, and the TCR stimulation markedly increased $CD4^+CD25^+$ T cells expressing galectin-9 on cell surfaces (FIG. 14D). These cells secreted a significantly larger amount of galectin-9 than the $CD4^+CD25^+$ T cells not expressing galectin-9 on cell surfaces, and also exhibited higher mRNA expressions of IL-10 and TGF-β (FIG. 14E). On the other hand, there was no significant difference in mRNA expressions of IL-2 and INF-γ between these cell groups, and the mRNA expressions of IL-4 and IL-17 were lower rather in the cells expressing galectin-9 on cell surfaces (FIG. 14E). These results verify that galectin-9 exhibits the same functions in humans and mice, and humans also have $T_H$GAL9 cells.

According to the present example, it was verified that $T_H$GAL9 secretes galectin-9 and can serve as a cell for adjusting $T_H$17/Treg balance. The fact that galectin-9 exhibits the same actions in mice and humans is a very important finding in clinical application of galectin-9, especially stabilized galectin-9. Moreover, from the fact that $T_H$GAL9 is present also in humans, it is considered that immune regulation by galectin-9 is well conserved across animal species. $T_H$GAL9 can be detected by detecting galectin-9 on a cell surface. Thus, as shown in FIG. 9A, the cells can be isolated and purified alive, which allows techniques applying these cells to be developed easily. Moreover, it was found that $T_H$GAL9 can be increased by adding stabilized galectin-9, which led to the discovery of one technique for increasing the cell expected to be useful in various applications in future in vitro. T cells other than $T_H$GAL9 also express equivalent galectin-9, but they do not secrete galectin-9. It is presumed that only $T_H$GAL9 can secrete galectin-9 owing to the secretion mechanism of this cell. If this secretion mechanism can be controlled, a novel immune regulation method can be provided. The discovery of $T_H$GAL9 would make a valuable contribution to the clarification of the galectin-9 secretion mechanism. For example, one possible method is performing exhaustive expression profiling at an mRNA level or a protein level using $T_H$GAL9 and other T cells. Also, there is a possibility that $T_H$GAL9 can be used as a surrogate marker to determine immune balance indirectly. For example, $T_H$GAL9 can serve as an indicator in: diagnosing various immune diseases, cancers, and infectious diseases; diagnosing the sensitivity to these diseases; and examining effects of drugs.

<Cells Expressing Galectin-9 on Cell Surfaces, Other than $T_H$GAL9>

It has been revealed that administration of stabilized human galectin-9 exhibits a drug efficacy not only in the above-described autoimmune disease models but also various disease models. In these cases, there is a possibility that the administered galectin-9 might trigger the induction of cells that secrete galectin-9 including $T_H$GAL9 galectin-9. $T_H$GAL9 was identified as a cell expressing galectin-9 on a cell surface, and it was verified that $T_H$GAL9 has a galectin-9-secreting ability. The inventors of the present invention considers that galectin-9 on a cell surface is detected while it is in an intermediate stage of its secretion, and it is thus expected that galectin-9-expressing cells other than $T_H$GAL9 can be searched for using the cell surface galectin-9 expression as an indicator. The state where galectin-9 is exposed at least on a cell surface results from the fact that the galectin-9 already has been translocated through the cell membrane, and in a broad sense, the galectin-9 in this state is "secreted". Thus, in various disease models, the presence of a cell group expressing galectin on cell surfaces was examined.

<Effect of Stabilized Galectin-9 in Peritonitis Model and Cell Surface Galectin-9 Expressing Cells Induced at this Time>

Figure 15:
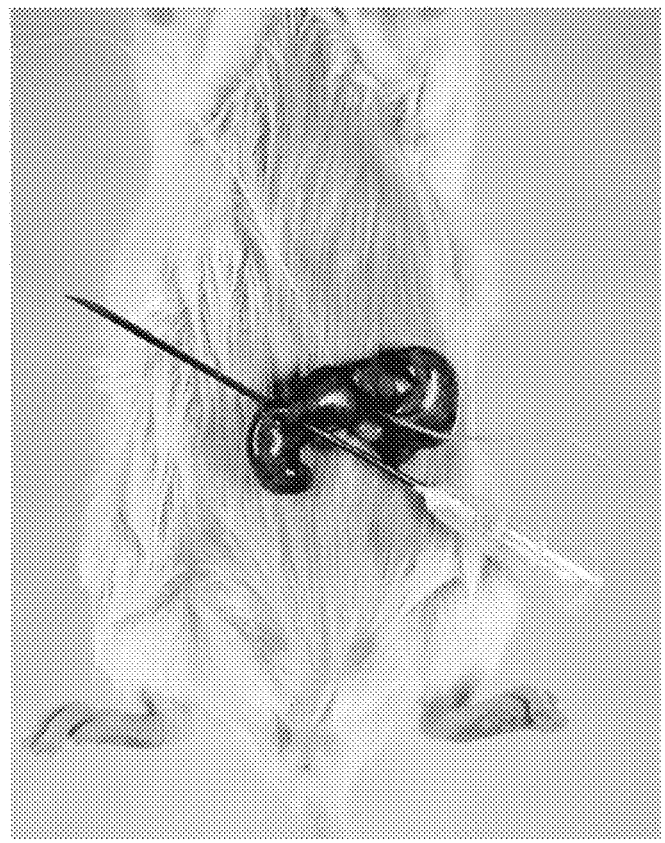
FIG. 15 is a photograph showing one example of a mouse subjected to cecal ligation and puncture (CLP), which is a serious peritonitis model.

FIG. 15 shows a mouse subjected to cecal ligation and puncture (CLP) to cause peritonitis as a serious peritonitis model. In the present experiment, BALB/c mice were used. In this disease model, the ligated cecum of each mouse was punctured with a G21 needle, and the survival of the mice after this treatment was examined over time.

FIG. 16 shows the results of examining the effectiveness of administration of stabilized human galectin-9 in CLP. This finding was made by Akihiro Matsukawa, a professor of the medical school of Okayama University, and already reported in academic conferences etc. Thus, only the overview of the result will be described herein. The onset of peritonitis was induced in the mice by CLP, and the survival rate of the mice was examined over time. (A) Comparison between C57BL/6J wild-type mice (WT) and mouse galectin-9 transgenic mice (Gal-9 Tg). (B) The survival rate in the case where the WT mice were subjected to CLP, and at the same time, they were given single intravenous administration of the stabilized human galectin-9 (30 µg/mouse; or PBS as a control). (C) The survival rate in the case where the WT mice were subjected to a CLP treatment, and 24 hours after the treatment, they were given single intravenous administration of the stabilized human galectin-9 (30 µg/mouse; or PBS as a control). (D) The survival rate in the case where the WT mice were subjected to a CLP treatment, and 24 hours after the treatment, they were given single subcutaneous administration of the stabilized human galectin-9 (30 µg/mouse; or PBS as a control). (E) The survival rate in the case where nude mice were subjected to CLP, and at the same time, they were given single subcutaneous administration of the stabilized human galectin-9 (30 µg/mouse; or PBS as a control).

Figure 16A:
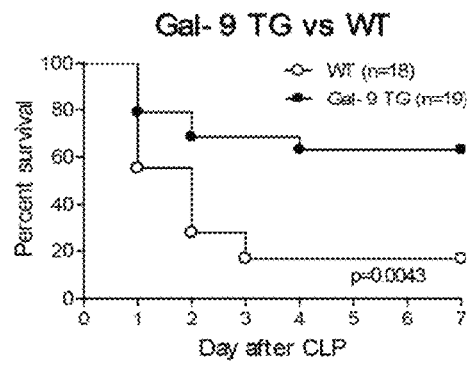
FIG. 16A shows comparison between C57BL/6J wild-type mice (WT) and mouse galectin-9 transgenic mice (Gal-9 Tg). (B)
Figure 16B:
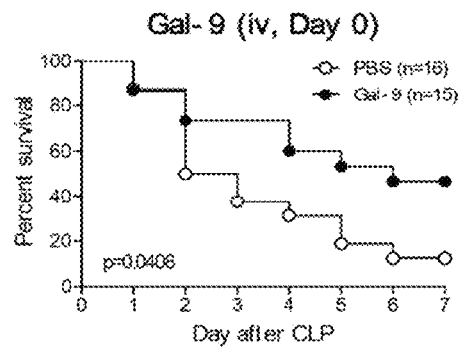
FIG. 16B shows the survival rate in the case where the WT mice were subjected to CLP, and at the same time, they were given single intravenous administration of the stabilized human galectin-9 (30 µg/mouse; or PBS as a control). (C)
Figure 16C:
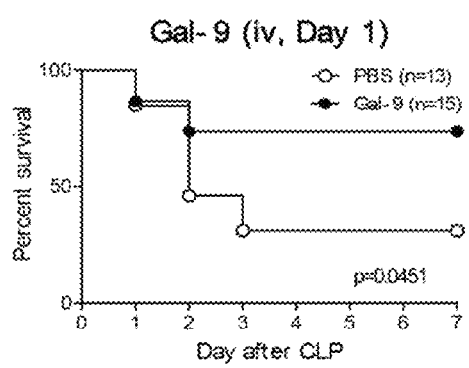
FIG. 16C shows the survival rate in the case where the WT mice were subjected to a CLP treatment, and 24 hours after the treatment, they were given single intravenous administration of the stabilized human galectin-9 (30 µg/mouse; or PBS as a control). (D)
Figure 16D:
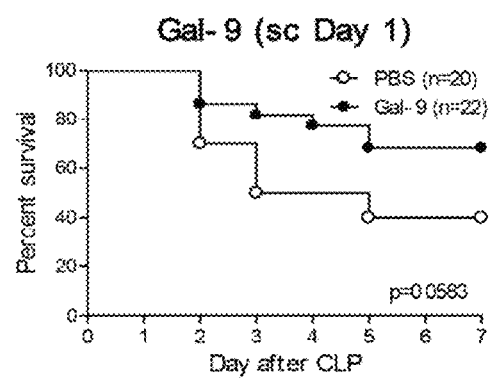
FIG. 16D shows the survival rate in the case where the WT mice were subjected to a CLP treatment, and 24 hours after the treatment, they were given single subcutaneous administration of the stabilized human galectin-9 (30 µg/mouse; or PBS as a control). (E)
Figure 16E:
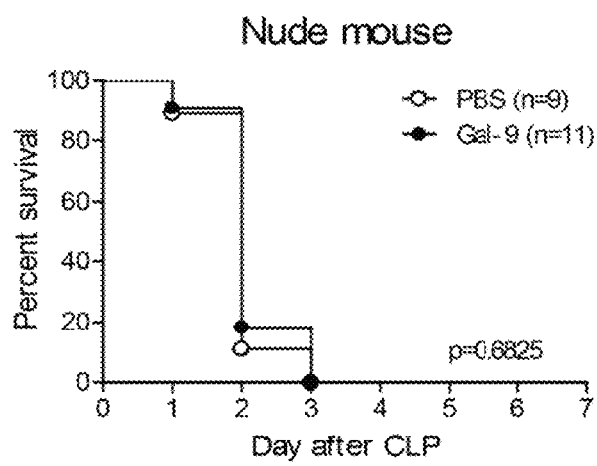
FIG. 16E shows the survival rate in the case where nude mice were subjected to CLP, and at the same time, they were given single subcutaneous administration of the stabilized human galectin-9 (30 µg/mouse; or PBS as a control). In each graph, the horizontal axis indicates the number of days elapsed after the CLP treatment, and the vertical axis indicates the survival rate.

Also in this serious peritonitis, the survival rate of the mice was improved significantly by the single administration of the stabilized galectin-9 immediately after CLP or 24 hours after CLP. However, this effect was not observed in the nude mice (FIG. 16E). These results strongly suggest that stabilized galectin-9 exhibits its action via a T cell.

Figure 17:
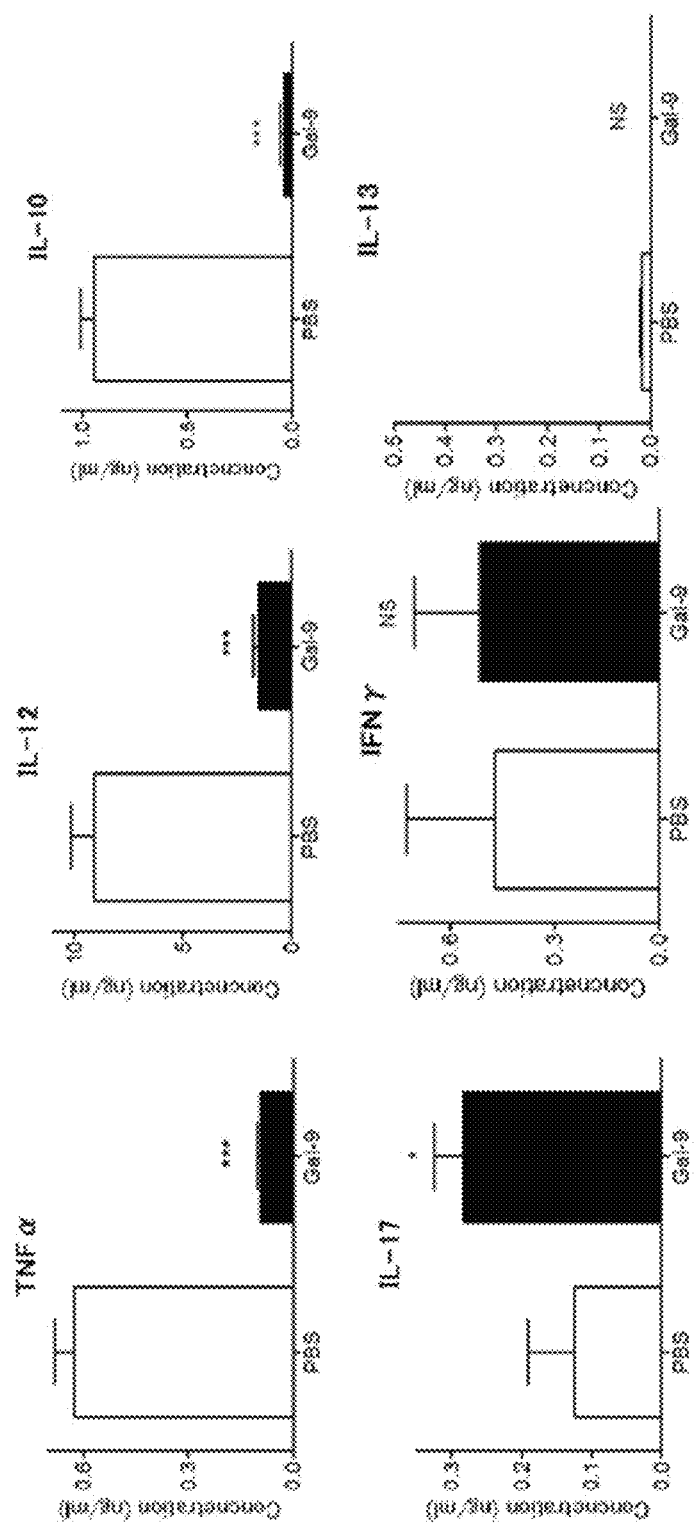
FIG. 17 shows graphs showing the results of examining the change in cytokine balance resulting from the administration of stabilized human galectin-9 to CLP mice in still another example of the present invention. WT mice were subjected to CLP, and at the same time, they were given single intravenous administration of stabilized human galectin-9 (30 µg/mouse; or PBS as a control). 24 hours later, spleen cells were taken out, and cultured for 24 hours.

FIG. 17 shows the results obtained when spleen cells taken out from the mice 24 hours after CLP were cultured, and the concentrations of cytokines in the culture supernatant were examined. This also has been reported by Akihiro Matsukawa, a professor of the medical school of Okayama University in academic conferences etc. In the spleen cells of the mice to which the stabilized galectin-9 had been administered, the production of TNF-α, IL-12, and IL-10 was decreased, whereas the production of IL-17 was increased. Although the galectin-9 served to decrease IL-17 in the autoimmune disease models in the above described experiments, the galectin-9 increased IL-17 in the present experiment. Galectin-9 is a bidirectional immunoregulatory factor, and exhibits different actions depending on a situation or the type of a cell on which it acts. For example, it has been reported that galectin-9 inhibits TNF-α in autoimmune diseases, whereas it acts on monocytes or dendritic cells to stimulate the production of TNF-α (Non-Patent Document 13). Thus, it is not hard to anticipate that the directionality of galectin-9 might change depending on a situation also with respect to IL-17. Inflammatory cytokines such as TNF-α, IL-12, and IL-17 serve to eliminate microorganisms, and on the other hand, they also cause tissue destruction by excess inflammatory provocation. From the fact that the administration of stabilized galectin-9 improved the survival rate, it is presumed that the change in cytokine balance observed in this experiment was advantageous to the survival under the peritonitis, although the specific mechanism thereof is unknown. Obviously, galectin-9 plays an important role in peritonitis (or sepsis).

Figure 18:
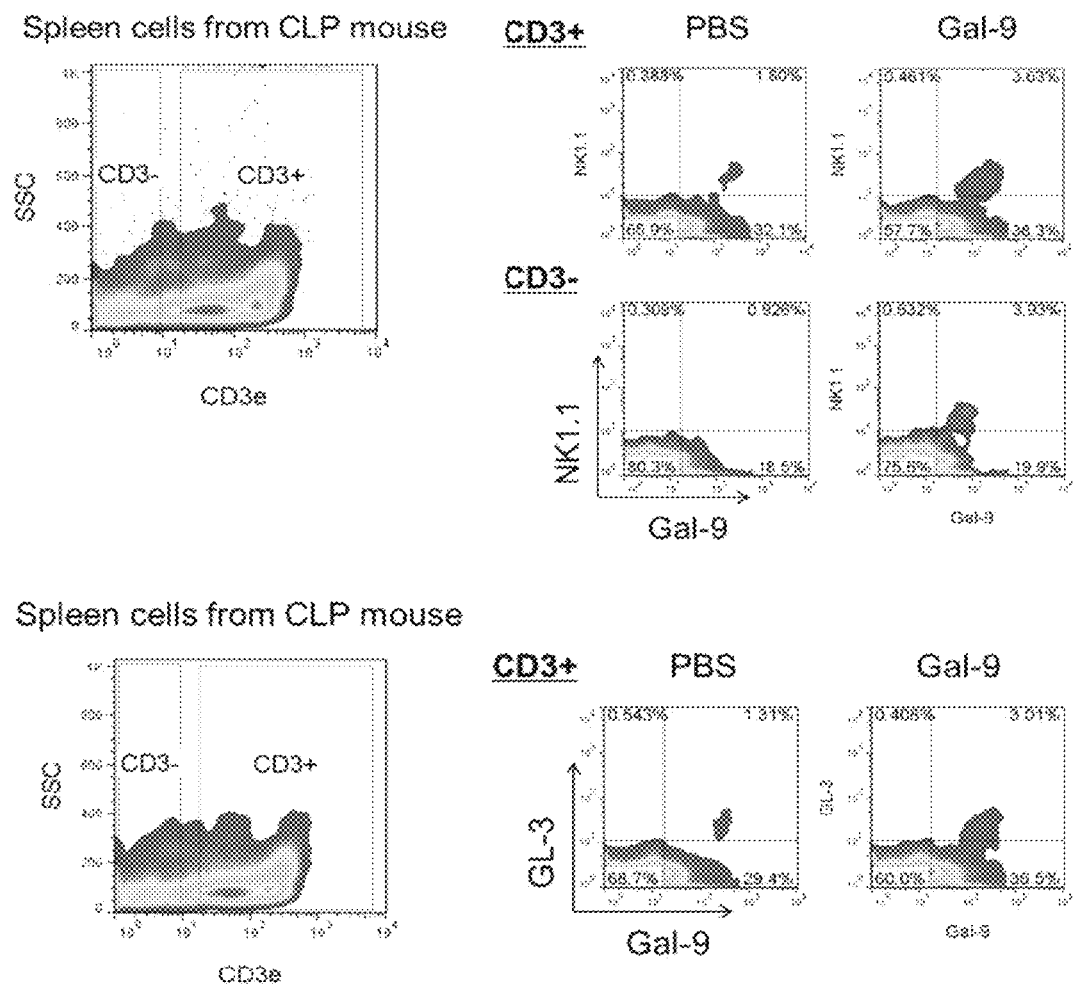
FIG. 18 shows the results of examining cell surface galectin-9 positive cells induced by administration of stabilized human galectin-9 to CLP mice in still another example of the present invention. WT mice were subjected to CLP, and at the same time, they were given single intravenous administration of stabilized human galectin-9 (30 µg/mouse; or PBS as a control). 24 hours later, spleen cells were taken out.

FIG. 18 shows the results obtained when CD3, NK1.1, GL-3, and cell surface galectin-9 in the spleen cells 24 hours after the CLP were stained, and analyzed by flow cytometry. As a result, it was found that cells expressing galectin-9 on cell surfaces were increased by the administration of stabilized galectin-9. Among the cells expressing galectin-9 on cell surfaces, the following cells were increased particularly notably: NKT cells (CD3$^+$NK1.1$^+$), a cell population containing T$_H$GAL9 (CD3$^+$NK1.1$^-$ and CD3$^+$GL-3$^-$), and γδT cells (CD3$^+$GL3$^+$). In particular, regarding the NKT cells, NK cells, and γδT cells, it was first discovered that nearly all of them were cell surface galectin-9 positive at least in this model. It is quite likely that these cells regulate immunity by galectin-9, similarly to T$_H$GAL9. This suggests that transferring these cells would be useful in treatment of serious peritonitis.

FIG. 19 shows the results obtained when stable galectin-9 was administered to cancer-carrying mice, and cell surface galectin-9 positive cells induced at this time were examined. As previously reported, administration of stabilized galectin-9 to mice with intraperitoneally transplanted mouse fibrosarcoma Meth A cells prolongs the survival of the mice (Non-Patent Document 32). Meth A cells were introduced into the abdominal cavity of each mouse according to the reported method. From immediately after the introduction, stabilized human galectin-9 was administered intraperitoneally three times a week (30 µg/mouse). 7 days after the Meth A transplantation, intraperitoneal cells and spleen cells were taken out from the mice, and the cell surface markers indicated in FIG. 19 were stained. FIG. 19 shows the results of measuring the cell surface markers by flow cytometry.

Figure 19A:
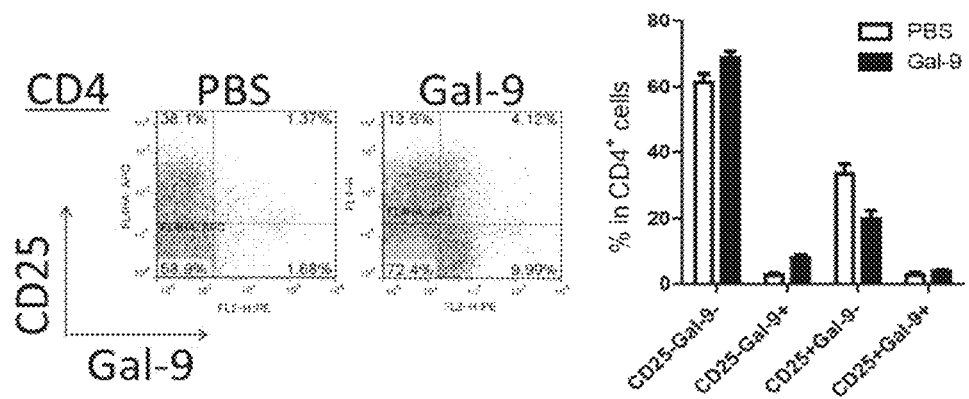
FIG. 19A shows the results of gating CD4 positive cells in the intraperitoneal cells based on the expressions of CD25 and cell surface galectin-9. By the administration of the stabilized human galectin-9, the proportion of the cells expressing galectin-9 on cell surfaces was increased markedly, whereas CD25$^+$Gal-9$^-$ cells were decreased. CD25$^+$Gal-9$^-$ cells are a cell population containing Treg cells, which are considered to inhibit immunity against cancers. (B)

(A) FIG. 19A shows the results of gating CD4 positive cells in the intraperitoneal cells based on the expressions of CD25 and cell surface galectin-9. By the administration of the stabilized human galectin-9, the proportion of the cells expressing galectin-9 on cell surfaces was increased markedly, whereas CD25$^+$Gal-9$^-$ cells were decreased. CD25$^+$Gal-9$^-$ cells are a cell population containing Treg cells, which are considered to inhibit immunity against cancers.

Figure 19B:
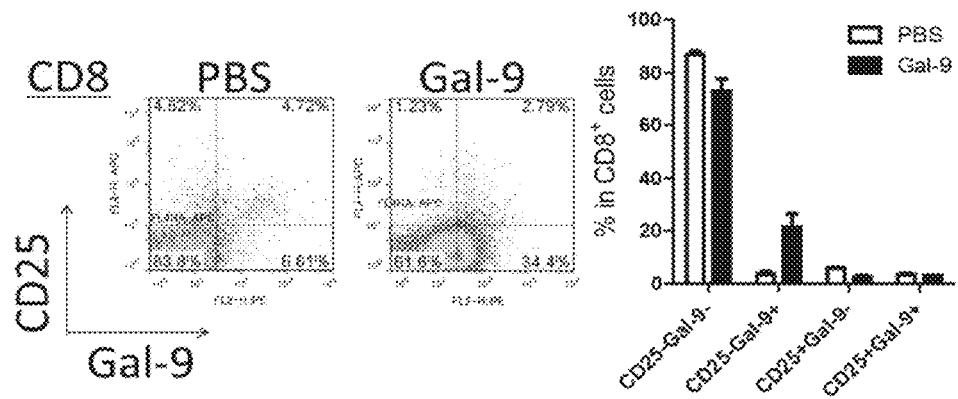
FIG. 19B shows the results of gating CD8 positive cells in the intraperitoneal cells based on the expressions of CD25 and cell surface galectin-9. By administration of the stabilized human galectin-9, the proportion of the CD8 cells expressing galectin-9 on cell surfaces was increased markedly. (C)

(B) FIG. 19B shows the results of gating CD8 positive cells in the cells described in the above (A) based on the expressions of CD25 and cell surface galectin-9. By administration of the stabilized human galectin-9, the proportion of the CD8 cells expressing galectin-9 on cell surfaces was increased markedly.

Figure 19C:
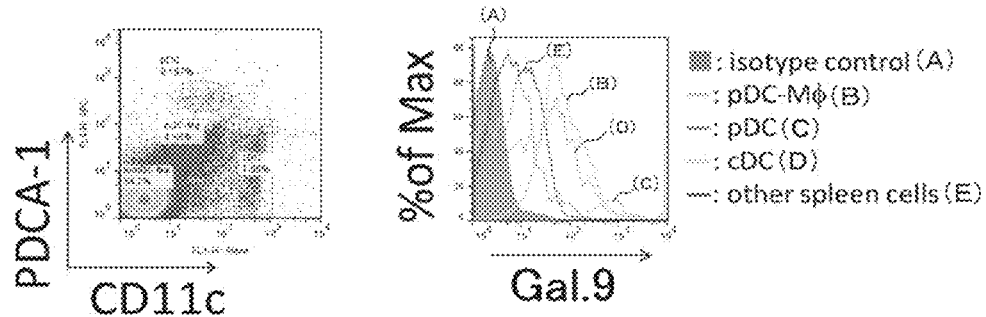
FIG. 19C shows the results obtained when PDCA-1, CD11c, and cell surface galectin-9 in the spleen cells of the Meth A cancer-carrying mice having been given stabilized human galectin-9 were stained, and measured by flow cytometry. The cell surface galectin-9 expression levels were compared in the following respective cell groups: plasmacytoid dendritic cells (pDC), pDC-like macrophages (pDC-Mϕ), conventional dendritic cells (cDC), and cells other than the dendritic cells and macrophages (non-DCMϕ, indicated as "other spleen cells" in FIG. 19C).

(C) FIG. 19C shows the results obtained when PDCA-1, CD11c, and cell surface galectin-9 in the spleen cells of the Meth A cancer-carrying mice having been given stabilized human galectin-9 were stained, and measured by flow cytometry. The cell surface galectin-9 expression levels were compared in the following respective cell groups: plasmacytoid dendritic cells (pDC), pDC-like macrophages (pDC-Mφ), conventional dendritic cells (cDC), and cells other than the dendritic cells and macrophages (non-DCMφ). It has been reported that, in an acute lung disorder model, transfer of pDC-like macrophages inhibits the symptoms (Non-Patent Document 44). Also in this case, it is presumed that galectin-9 secreted by the pDC-like macrophages is chiefly responsible for the effect.

Also in this cancer-carrying model, when the administered stabilized galectin-9 exhibited a drug efficacy, cells expressing galectin-9 on cell surfaces emerged as described above. This suggests that transferring these cells would be useful in cancer treatment. This also suggests the possibility that it might be possible to diagnose cancer progression or a treatment effect by using these cells as a marker.

Figure 20A:
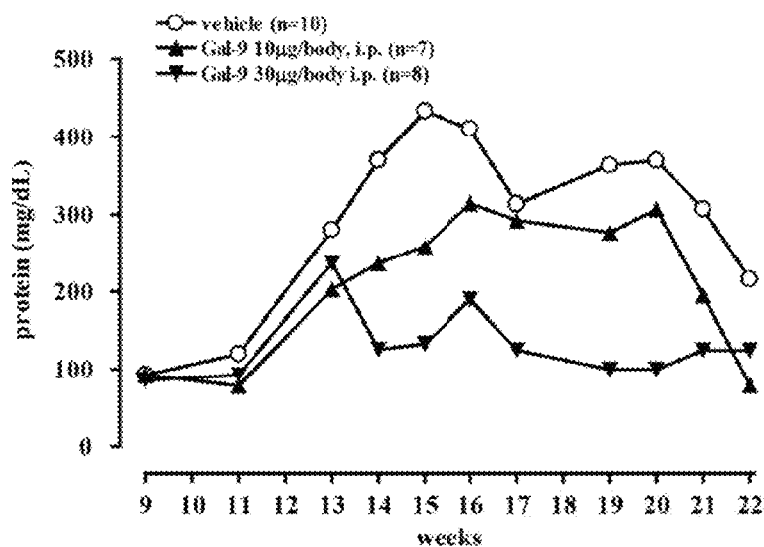
FIGS. 20A and 20B show the results of examining the effectiveness of stabilized human galectin-9 in a spontaneous autoimmune disease model in still another example of the present invention. MRL/MpJUmmCrj-lpr/lpr mice are a spontaneous autoimmune disease model used widely as a systemic erythematosus model. To these mice (♀, 8-week old), stabilized human galectin-9 was administered intraperitoneally 3 times/week at each dose indicated in FIG. 20 until they became 22-week old. The following items were measured over time: the volume of the pedal edema in hind paws (once a week); the weight (three times a week); and the urine protein concentration (once a week).
Figure 20B:
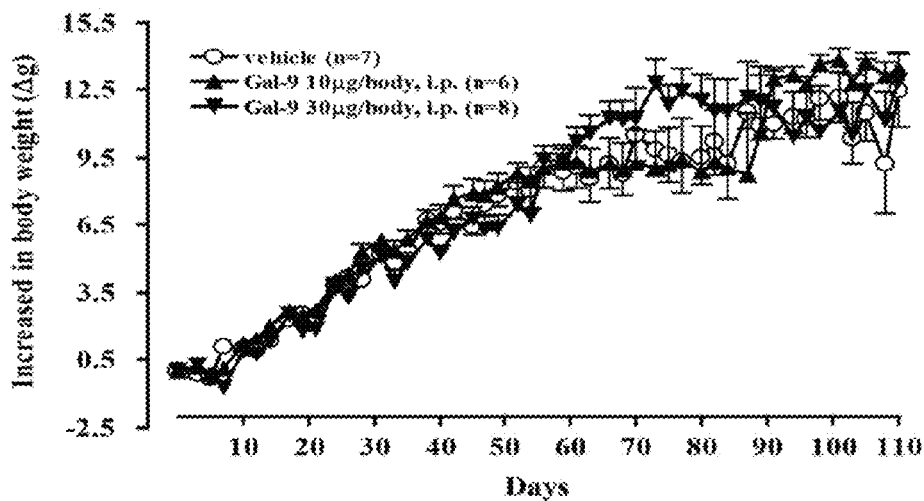
Figure 21A:
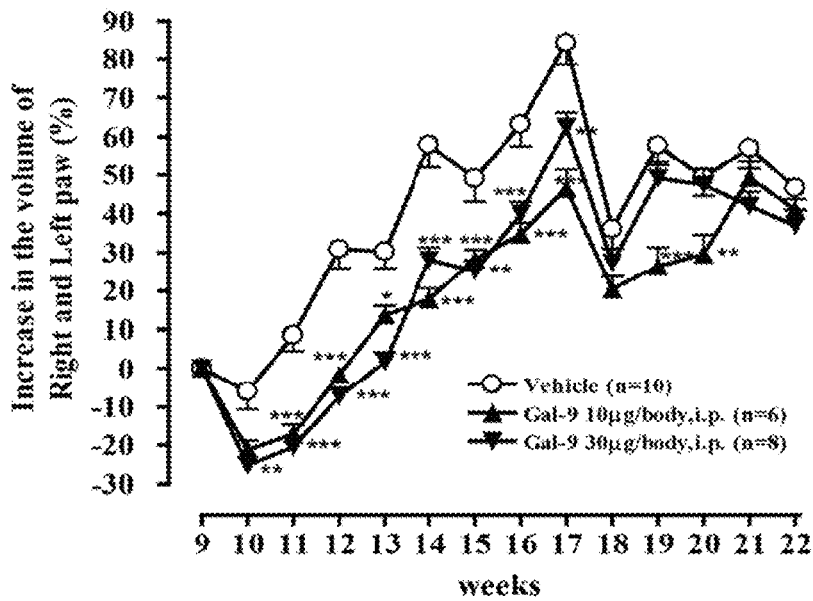
FIG. 21A shows the results of examining the change in volume of pedal edema in hind paws in the experiment described with reference to FIG. 20.
Figure 21B:
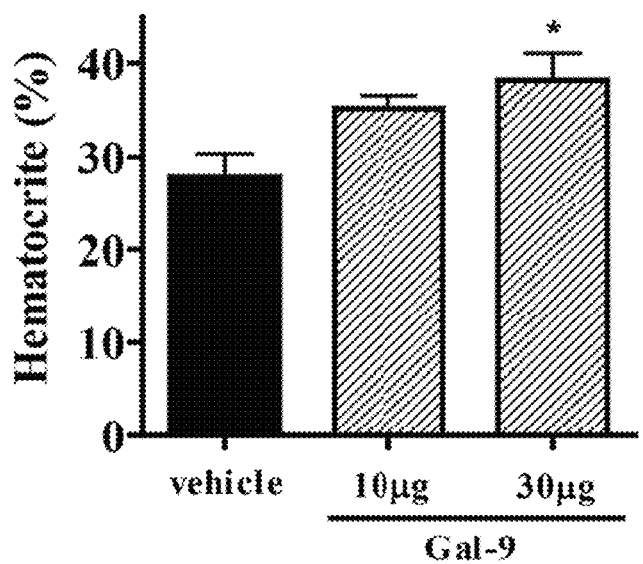
FIG. 21B shows the hematocrit value at the end of the experiment (at 22 weeks of age) (FIG. 21B).
Figure 22A:
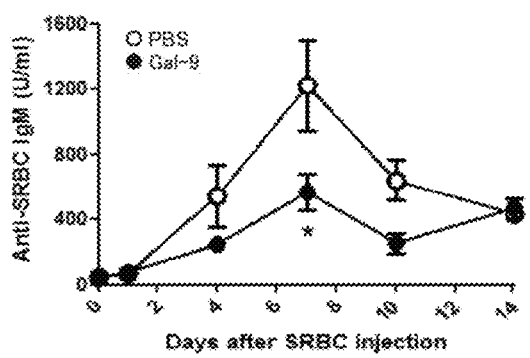
FIGS. 22A-22D show the results of examining the effect of stabilized human galectin on antibody production in still another example of the present invention. Sheep red blood cells (SRBC) administered to a mouse markedly evokes the production of IgM antibodies against the sheep red blood cells. Thus, this system is used widely for the purpose of examining the effect of a drug on antibody production. SRBC was administered intraperitoneally to C57BL/6J mice (♀), and immediately after the administration, the C57BL/6J mice were given single intraperitoneal administration of stabilized human galectin-9 (30 µg/mouse) or PBS as a control. At each given time point, blood collection and spleen extirpation were performed with respect to three to five mice, and the antibody production and B cells were examined.
Figure 22B:
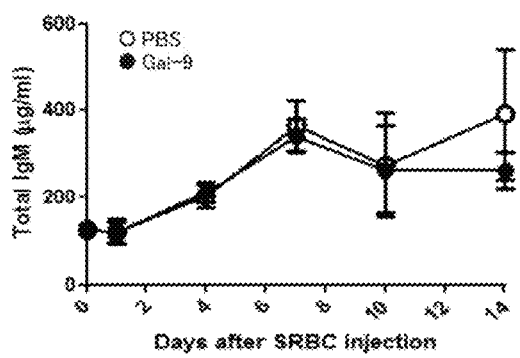
Figure 22C:
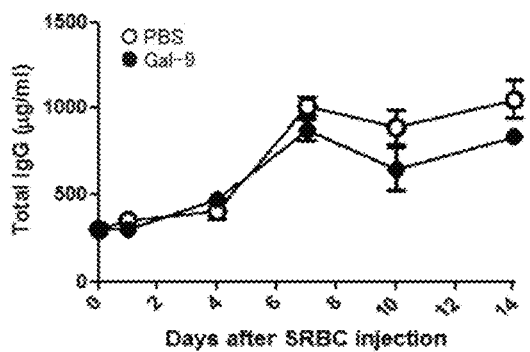
Figure 22D:
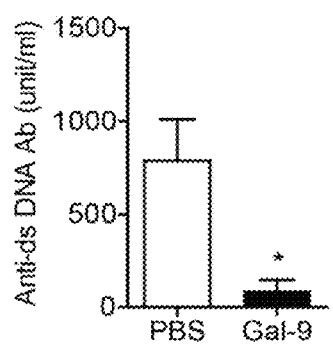

FIGS. 20 to 21 show the results of examining the effectiveness of stabilized human galectin-9 in a spontaneous autoimmune disease model. MRL/MpJUmmCrj-lpr/lpr mice are a spontaneous autoimmune disease model used widely as a systemic erythematosus model. To these mice (♀, 8-week old), stabilized human galectin-9 was administered intraperitoneally 3 times/week at each dose indicated in FIG. 20 until they became 22-week old. The following items were measured over time: the volume of the pedal edema in hind paws (once a week; measured using PLETHYSMOMETER as in the experiment described with reference to FIG. 1); the weight (three times a week); and the urine protein concentration (once a week). When the stabilized human galectin-9 was administered at a high dose of 30 μg/mouse, statistically significant therapeutic effects were observed in all of the urine protein concentration (FIG. 20A), the change in weight (FIG. 20 b), the change in volume of the pedal edema in hind paws (FIG. 21A), and the hematocrit value at the end of the experiment (at 22 weeks of age) (FIG. 21B). Systemic erythematosus is a very serious autoimmune disease. In past 50 years, there was no other choice but to administer high-dose steroid for the treatment of systemic erythematosus. In this disease, the production of self-reactive antibody is outstanding. Thus, it has been considered that treatment for inhibiting the antibody production would be the solution to the diseases. Belimumab, approved by FDA in 2011, is an antibody that inhibits B cells, and clinical studies verified that, as targets of the treatment of this disease, it is important to inhibit B cells and the production of self-reactive antibodies.

FIG. 22 shows the results of examining the action of stabilized galectin-9 on antibody production. As described above, stabilized galectin-9 was effective against a mouse model of systemic erythematosus, so that the possibility is suggested that the stabilized galectin-9 might act to inhibit the antibody production and B cells. Thus, the effect of stabilized galectin-9 was examined using an anti-sheep red blood cell IgM antibody-producing system by sheep red blood cell (SRBC) administration, which is used widely for examination of an effect of a drug on the production of antibodies. SRBC was administered intraperitoneal to C57BL/6J mice (♀), and immediately after the administration, the C57BL/6J mice were given single intraperitoneal administration of stabilized human galectin-9 (30 μg/mouse) or PBS as a control. At each given time point, blood collection and spleen extirpation were performed with respect to three to five mice, and the antibody production and B cells were examined. As a result, it was found that the administration of the stabilized human galectin-9 decreased the concentration of IgM specific to SRBC (FIG. 22A), but did not cause any statistical change in the total IgM concentration (FIG. 22B) and the total IgG concentration (FIG. 22C). Furthermore, the stabilized human galectin-9 or PBS as a control was administered to MRL/MpJUmmCrj-lpr/lpr mice (♀, 8-week old) 3 times/week at a dose of 30 μg/mouse. Blood was collected from each mouse on day 7, and the concentration of anti-double-stranded DNA antibody (a typical autoimmune antibody) in serum was examined. As a result, it was found that the anti-double-stranded DNA antibody was inhibited significantly by the administration of the stabilized galectin-9 (FIG. 22D). This suggests the possibility that these effects might result from the fact that stabilized galectin-9 acts on B cells, which are chiefly responsible for the antibody production.

Figure 23:
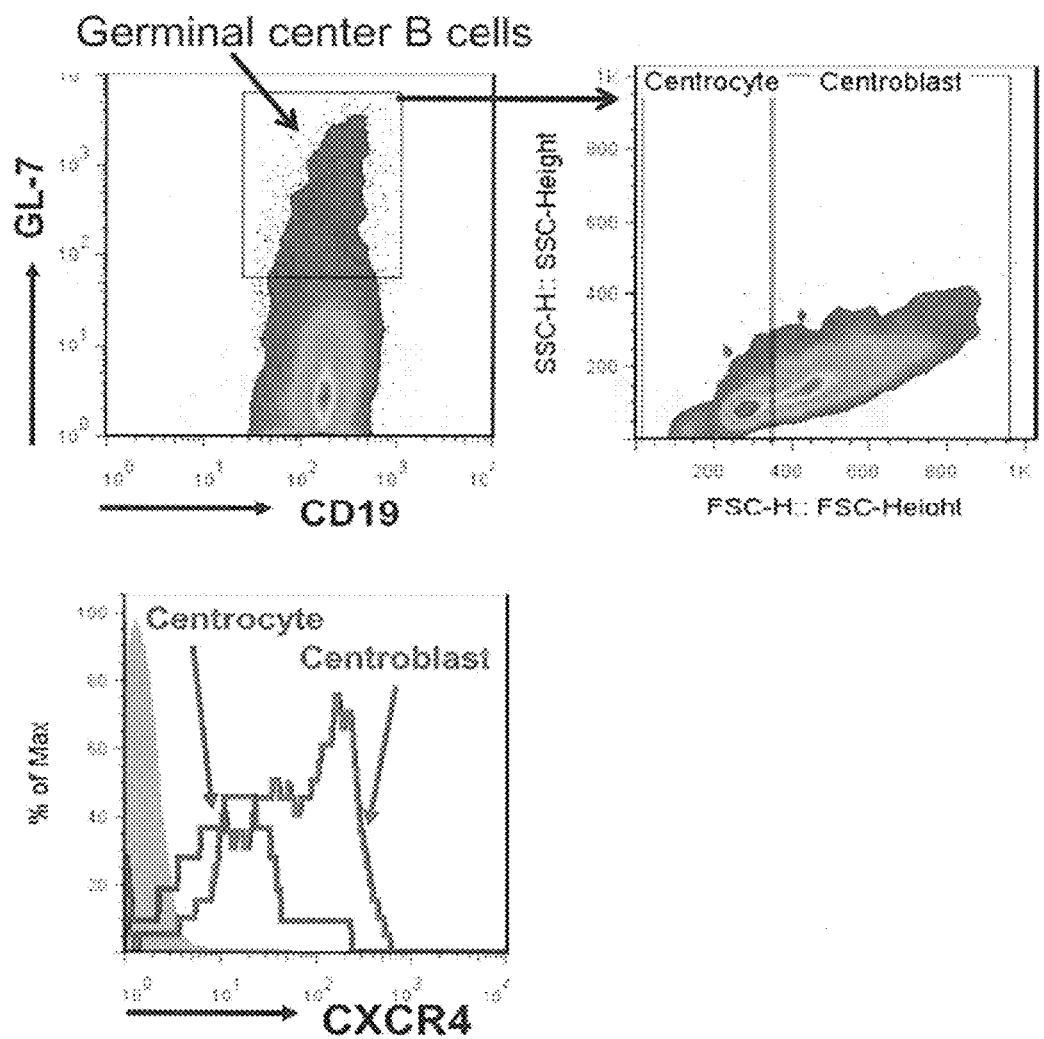
FIG. 23 shows an analysis method of germinal center B cells contained in spleen cells based on flow cytometry in still another example of the present invention. The spleen cells were stained with an anti-CD19 antibody and an anti-GL-7 antibody, and a CD19$^+$GL-7$^+$ cell population was determined as germinal center B cells. It is known that centrocytes and centroblasts constituting the germinal center B cells have different cell sizes, and centroblasts are larger than centrocytes. Thus, the germinal center B cell population was gated based on FSC and SSC. The germinal center B cell population was separated into two cell populations using the FSC-height (which correlates with the cell size) in the vicinity of about 350 as a boundary. These cell populations were provisionally assumed to be centrocytes and centroblasts. The CXCR4 expression in each cell population was examined. As a result, the centroblasts exhibited a higher expression of CXCR4. This agrees with known properties of centroblasts and centrocytes. Thus, when it was necessary to analyze centrocytes and centroblasts separately in subsequent analyses, the method shown in FIG. 23, i.e., gating a CD19$^+$GL-7$^+$ cell population based on FSC and SSC, was employed.

FIG. 23 shows the method used to analyze the B cells. When CD19 and GL-7 of spleen cells are stained for gating by flow cytometry, the spleen cells are separated into germinal center B cells ($CD19^+GL-7^+$) and other B cells ($CD19^+GL-7^-$). When the germinal center B cells are sorted further according to the cell size on the basis of the FSC values, the germinal center B cells can be separated into centroblasts with a relatively large cell size and centrocytes with a relatively small cell size. This separation to centroblasts and centrocytes based on FSC agrees well with the reported fact that the CXCR4 expression is high in the centroblasts and low in the centrocytes. Thus, this method was employed in subsequent analyses.

Figure 24A:
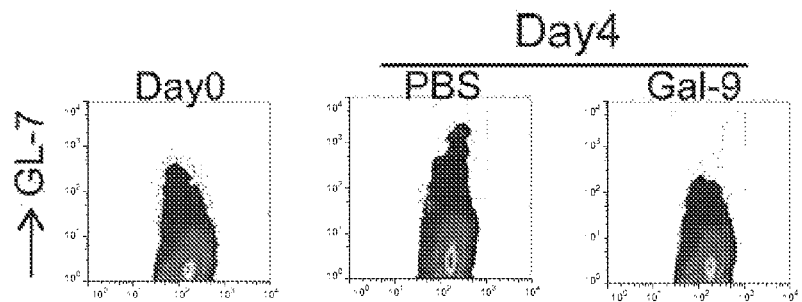
FIG. 24A shows an example of the analysis result by the flow cytometry on day 4 after the SRBC administration. (B)
Figure 24B:
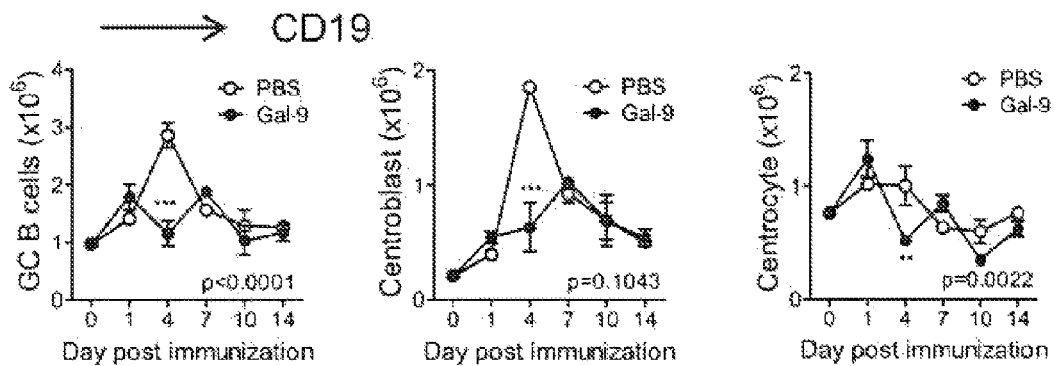
FIG. 24B shows the change in the number of germinal center B cells (GC B cells), centroblasts, and centrocytes over time.
Figure 24C:
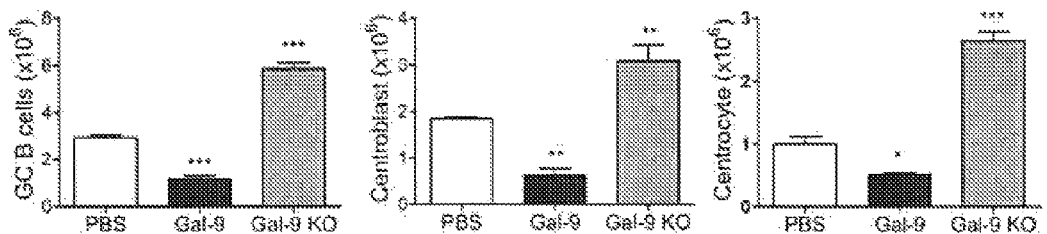
FIG. 24C shows the number of germinal center B cells (GC B cell), centroblasts, and centrocytes on day 4 after the SRBC administration. To the galectin-9 knockout mice (Gal-9 KO), PBS was administered after the SRBC administration.

FIG. 24 shows the results of examining the spleen cells isolated from the mice in the experiment described with reference to FIG. 22 over time. It was found that, on day 4 after the administration of the stabilized galectin-9, the germinal center B cells decreased, and both the centroblasts and centrocytes decreased (FIGS. 24A and 24B). Also, SRBC was administered to the galectin-9 knockout mice, and their spleen cells were analyzed on day 4 after the administration. As a result, the numbers of germinal center B cells and both centroblasts and centrocytes were greater than those in the wild-type mice. This is consistent with the effect of galectin-9 in vivo envisaged from the administration of the stabilized galectin-9. In other words, it is suggested that galectin-9 is a factor that inhibits B cell and the antibody production also in vivo. Accordingly, cells that secrete galectin-9 to negatively-control B cells and the antibody production must be present.

Figure 25A:
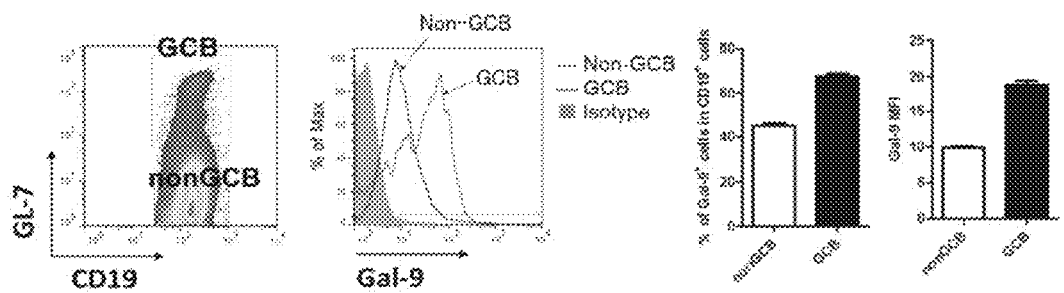
FIG. 25A shows the results of examining the expression of cell surface galectin-9 in each cell population. (B) The germinal center B cells described in the above (A) were further separated into centrocytes and centroblasts according to the flow cytometry shown in FIG. 23.
Figure 25B:
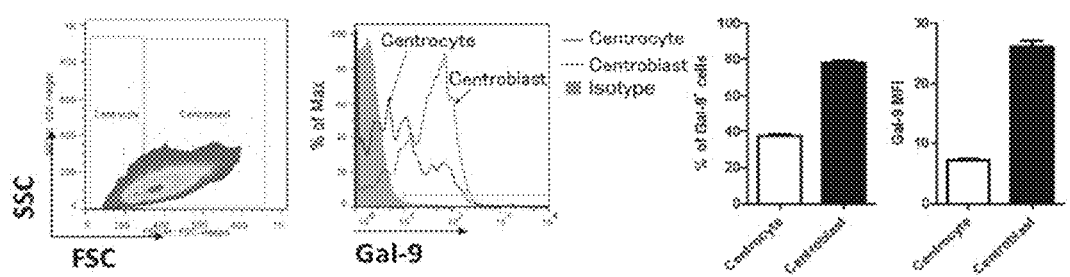
FIG. 25B shows the results of examining the expression of cell surface galectin-9 in each cell population. (C)
Figure 25C:
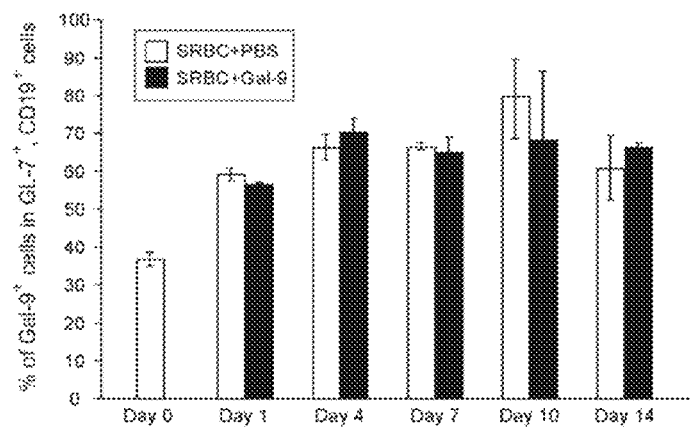
FIG. 25C shows the results of examining the expression of cell surface galectin-9 in the germinal center B cells examined in the above (B). The proportion of the germinal center B cells expressing galectin-9 on cell surfaces was increased by the SRBC administration, whereas the same was not changed by the administration of stabilized human galectin-9.
Figure 26A:
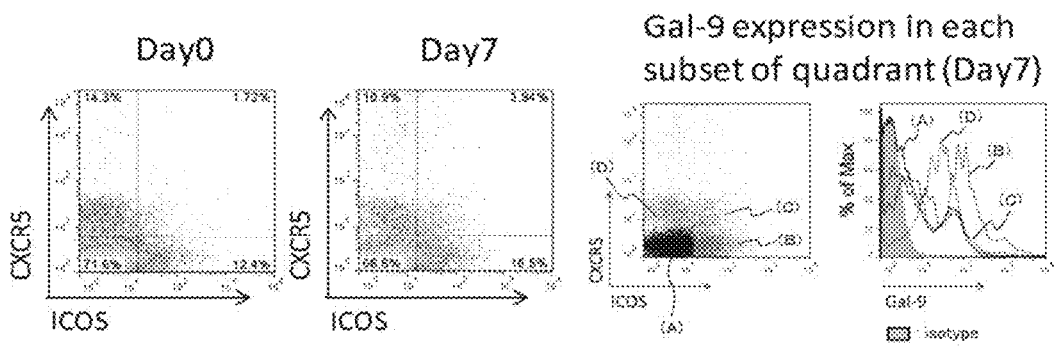
FIGS. 26A-26E show the results of analyzing the subtypes of helper T-cells in spleen cells under antibody-producing stimulation and the expression of cell surface galectin-9 in each subtype in still another example of the present invention. As described above, galectin-9 also acts on the antibody production and B cells. Differentiation of B cells in vivo and the antibody production are controlled by helper T-cells. In particular, it is said that a CD4 positive cell called "follicular B helper T cell" (TFH) play a major role. Thus, in mouse spleen cells before the SRBC administration (day 0) and 7 days after the SRBC administration (day 7), CXCR5 and ICOS, which are said to be CD4 and TFH markers were stained, and the cell surface galectin-9 expression in each cell population was examined by flow cytometry. (A)
Figure 26B:
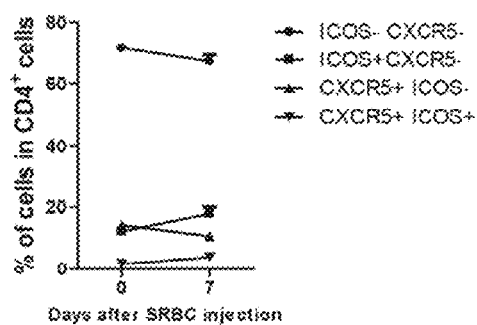
Figure 26C:
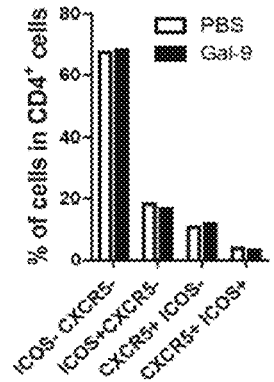
Figure 26D:
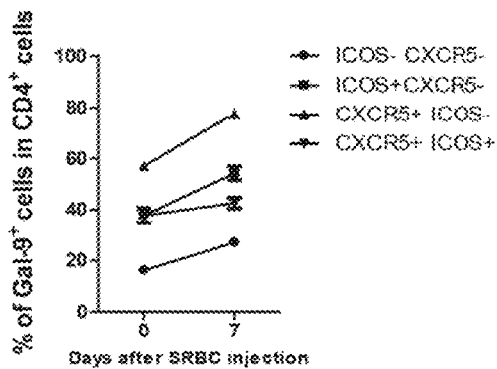
Figure 26E:
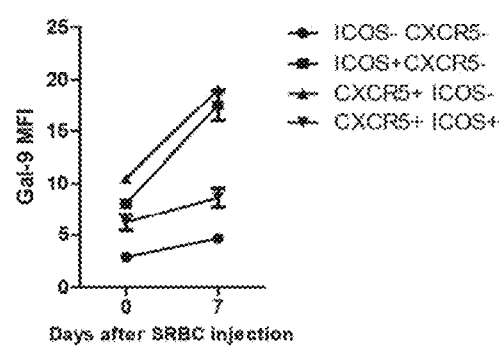

In an experiment to be described with reference to FIG. 25, first, galectin-9 expression on cell surfaces of B cells was examined. As a result, it was found that all the B cells, including germinal center B cells and other B cells, expressed galectin-9 on cell surfaces, and the expression of cell surface galectin-9 was high in the germinal center B cells (FIG. 25A). It was also found that, among the germinal center B cells, centroblasts exhibited a higher expression of cell surface galectin-9 (FIG. 25B). On the other hand, as far as can be seen from the examination on the germinal center B cells, it was found that the administration of the stabilized galectin-9 did not affect cell surface galectin-9 expression, but the proportion of the cells expressing galectin-9 on cell surfaces was increased by immunization with SRBC 9FIG. 25C.

CD4 T cells are deeply involved in maturation of B cells, and in particular, it is said that a CD4 positive cell called "follicular B helper T cell" (TFH) plays a major role. Thus, in an experiment to be described with reference to FIG. 26, mouse spleen cells on day 7 after the SRBC administration were stained with CXCR5 and ICOS (said to be CD4 and TFH markers), and the cell surface galectin-9 expression in each cell population was examined by flow cytometry. As can be seen from FIG. 26A to 26D, these CD4 T cells exhibited various cell surface galectin-9 expression levels. The cell surface galectin-9 expression was particularly high in $ICOS^-CXCR5^+$ CD4 positive cells and $ICOS^+CXCR5^-$ CD4 positive cells. This suggests the possibility that these cells secrete galectin-9 and control the antibody production.

This suggests the possibility that these cell groups expressing galectin-9 on cell surfaces might be useful in treatment and diagnosis of autoimmune diseases including systemic erythematous.

Figure 2:
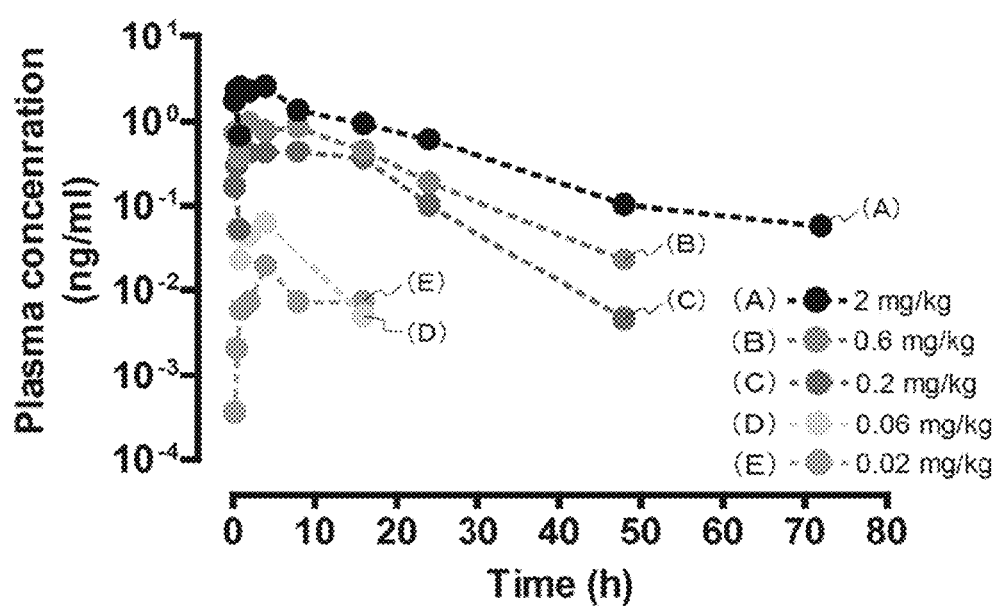
FIG. 2 is a graph showing the results of a pharmacokinetic test of stabilized human galectin-9 in rats in another example of the present invention. More specifically.
Figure 27:
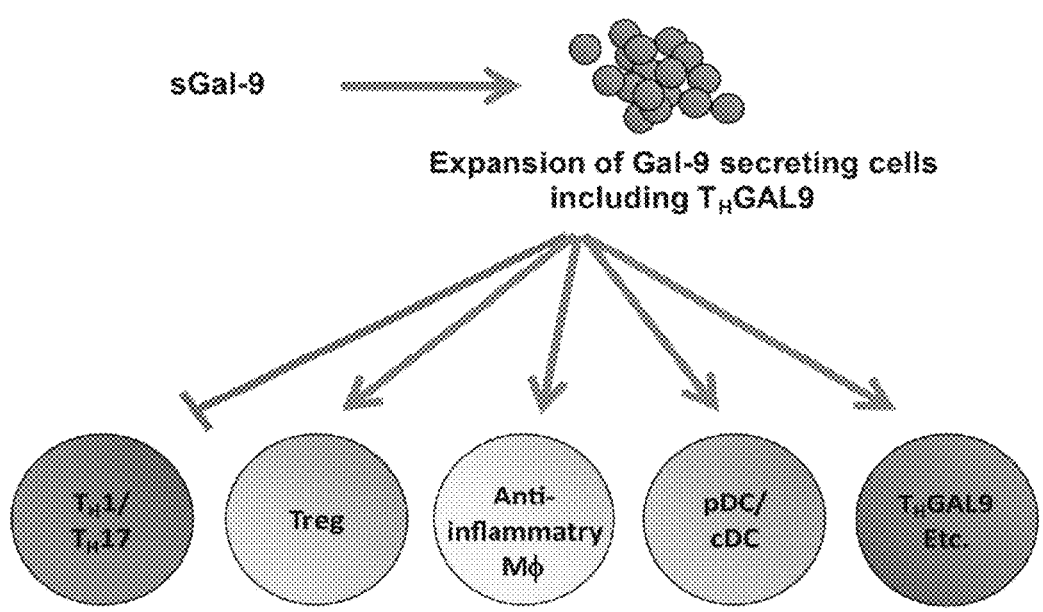
FIG. 27 schematically illustrates actions caused by administration of stabilized human galectin-9.

FIG. 27 schematically illustrates actions caused by administration of stabilized human galectin-9. As shown in FIG. 1, when the stabilized human galectin-9 is administered subcutaneously, the pharmacological effect thereof can last long. However, as shown in FIG. 2, the concentration of the stabilized human galectin-9 in blood after the administration is very low, so that it is unlikely that the stabilized human galectin-9 released in blood exhibits a drug efficacy at least in immune regulation. It is considered that the stabilized human galectin-9 is present at a higher concentration while it is at the administration site for the subcutaneous administration and while it passes through lymphatic vessels or lymph nodes, during which the stabilized human galectin-9 may act on immune cells. However, as can be seen from FIG. 2, the administered stabilized human galectin-9 is eliminated from the body rapidly. Thus, there is a possibility that, after the elimination of the stabilized galectin-9, the immune cells having been subjected to the action of the high concentration of galectin-9 might perform immune regulation, instead of the eliminated stabilized galectin-9. In the present invention, the inventors discovered a novel cell $T_H$GAL9, which expresses galectin-9 on a cell surface and also secretes the galectin-9 to adjust the $T_H$17/Treg balance. The inventors further discovered that $T_H$GAL9 is increased by adding stabilized human galectin-9. That is, it is considered that the administered stabilized human galectin-9 exhibits, in addition to the direct action thereof, an action of inducing $T_H$GAL9, and the thus-induced $T_H$GAL9 acts on various cells by secreting a necessary amount of galectin-9 in a localized region. This provides consistent explanation for the long-lasting immune regulatory activity of stabilized galectin-9. Furthermore, the inventors of the present invention considered that cell surface galectin-9 is in an intermediate stage of its secretion, and using the expression of cell surface galectin-9 as an indicator, they discovered various cell populations that secrete (or may secrete) galectin-9, other than $T_H$GAL9. These cells are considered to regulate immunity by secreting galectin-9, similarly to $T_H$GAL9.

<Administration of Galectin-9 Allows Prolonged Survival of LLC Cancer-Carrying Mice, and pDC-Like Macrophages is Increased at this Time>

As shown in FIG. 19C, the inventors of the present invention verified that conventional dendritic cells (cDC), plasmacytoid dendritic cells (pDC), and pDC-like macrophages express galectin-9 on cell surfaces, using the cells obtained in the Meth A cancer-carrying mouse model. The present example is directed to the same examination in another cancer. Specifically, as shown in FIG. 29, the administration of galectin-9 allowed prolonged survival of mice carrying another cancer, and pDC-like macrophages also were increased at this time.

Figure 29A:
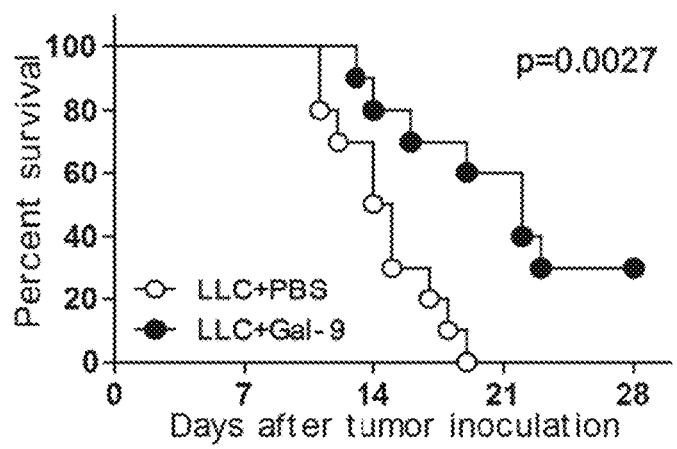
FIG. 29A is a graph showing the results of examining the survival rate. "Days after tumor inoculation" on the horizontal axis indicates the number of days elapsed after the tumor inoculation. "Percent survival" on the vertical axis indicates the survival rate.

(A) To abdominal cavities of C57BL/6 mice (♀, 7- to 10-week old), $5\times10^5$ cells of a mouse lung cancer-derived tumor cell line LLC were inoculated (day 0). From the day of the inoculation, stabilized human galectin-9 (control: PBS) was administered intraperitoneally to the mice three times a week at a dose of 30 μg. FIG. 29A shows the results of examining the change in survival rate over time. The horizontal axis ("Days after tumor inoculation") indicates the number of days elapsed after the LLC inoculation. The vertical axis ("Percent survival") indicates the survival rate expressed as a percent. The statistical analysis was carried out by the logrank test.

Figure 29B:
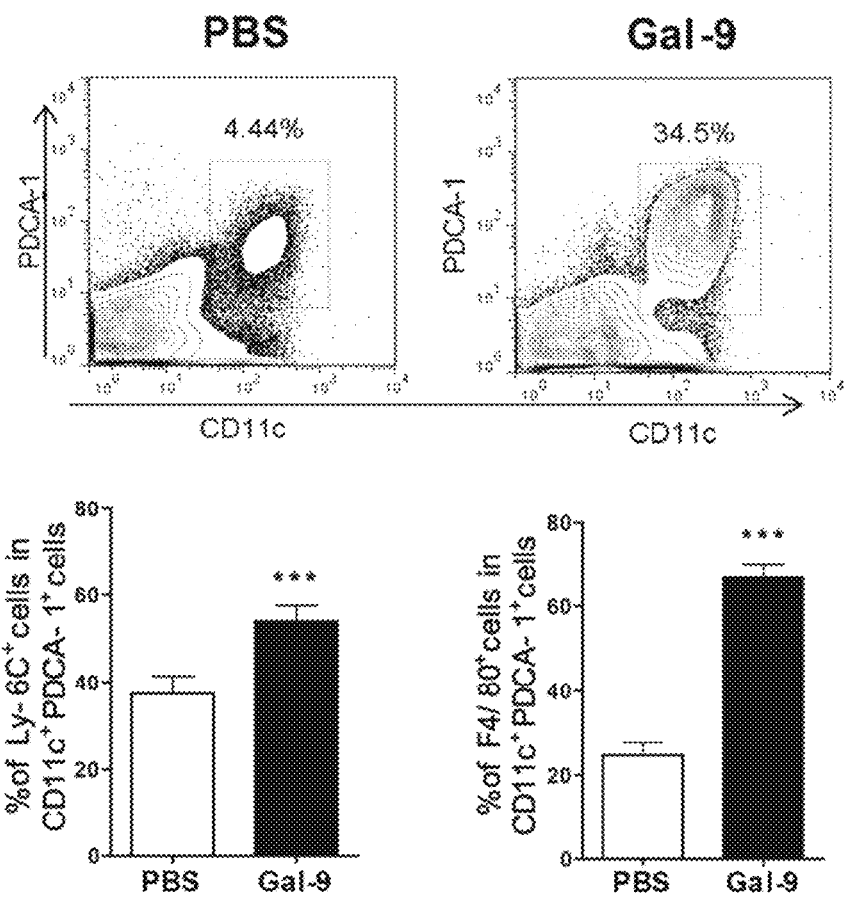
FIG. 29B shows the results obtained when the intraperitoneal cells on day 7 after the LLC inoculation were stained with antibodies against macrophage markers (Ly-6C and F4/80), a dendritic cell marker (CD11c), and a plasmacytoid dendritic cell marker (PDCA-1), and analyzed by flow cytometry.

(B) FIG. 29B shows the results obtained when the intraperitoneal cells on day 7 in the above (A) were stained with CD11c, PDCA-1, Ly-6C, and F4/80 antibodies, and analyzed by flow cytometry. In the galectin-9 administration group, CD11c and PDCA-1, which are both pDC markers, were expressed, and the proportion of the cells expressing a macrophage marker Ly-6C or F4/80, i.e., pDC-like macrophages, was increased significantly. From these results, it is presumed that pDC-like macrophages are involved in the prolonged survival by galectin-9. Each group consisted of 5 mice, and each value in FIG. 29B represents the mean±SEM. ***$P<0.001$.

<Galectin-9 Promotes Differentiation of CD11c Positive Cells with M-CSF in Test Tube in Tim-3 Independent Manner>

As shown in FIG. 30, in the present example, galectin-9 promoted differentiation of CD11c positive cells with M-CSF in a test tube in a Tim-3 independent manner.

Figure 30A:
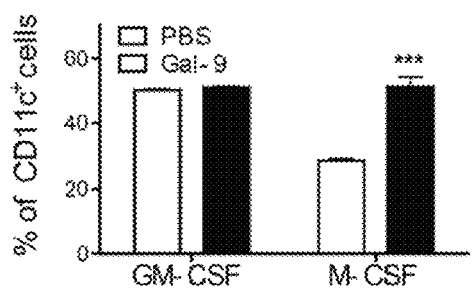
FIG. 30A shows the results of examining how stabilized galectin-9 (30 nM) affected the differentiation. (B)

(A) Bone marrow cells were washed out from femora and tibiae of mice. They were cultured for 2 hours in a RPMI-1640 medium containing 10% fetal bovine serum and an antibiotic, and adherent cells (mature macrophages) were removed. The remaining bone marrow cells were cultured for 7 days in a medium containing GM-CSF (Peprotech, 20 ng/ml) or M-CSF (R&D Systems, 20 ng/ml). This time, non-adherent cells were removed by washing, and the adherent cells were analyzed by flow cytometry. From the fact that more than 95% of the adherent cells were double positive for F4/80 and CD11b, these adherent cells were determined to be mature macrophages. FIG. 30A shows the results of examining how stabilized human galectin-9 (30 nM) given during the differentiation affected the expression of CD11c in these cells. Galectin-9 did not affect the CD11c expression in the macrophages differentiated with GM-CSF, but increased the CD11c expression in the macrophages differentiated with M-CSF.

Figure 30B:
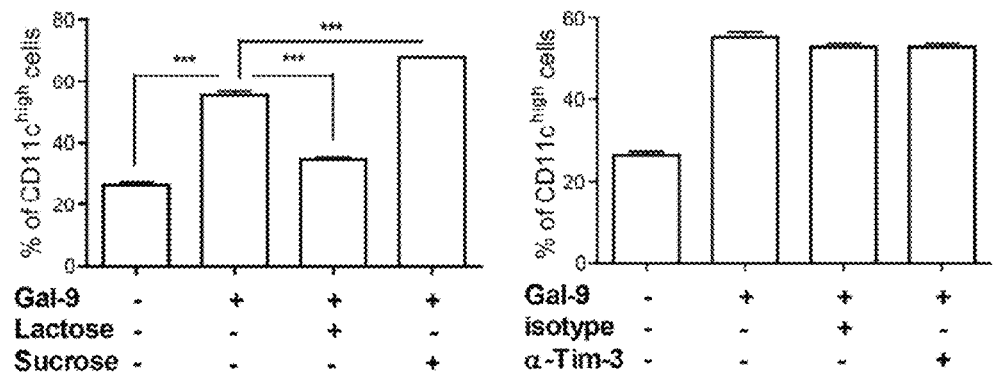
FIG. 30B shows the results obtained when the differentiation assay described in the above (A) was carried out in the presence of lactose as a galectin-9 inhibitor (sucrose as a control) or a neutralizing antibody of Tim-3.

(B) FIG. 30B shows the results obtained when the differentiation assay using M-CSF described in the above (A) was carried out in the presence of lactose (30 mM) as a galectin-9 inhibitor or sucrose (30 mM) as a control, and the results obtained when the differentiation assay was carried out in the presence of a Tim-3 neutralizing antibody (eBiosciences, RMT-3-23, 10 μg/ml) or an isotype control antibody (eBiosciences, 10 μg/ml). Lactose inhibited the increase in CD11c expression by galectin-9, but the Tim-3 neutralizing antibody did not affect the increase in CD11c expression. Tim-3 is a molecule most well known as the target of galectin-9. However, it is suggested that Tim-3 was not involved in the increase in CD11c expression by galectin-9 in the present experiment.

<CD11c Positive Cells Differentiated with Galectin-9 and M-CSF are pDC-Like Macrophage Precursor Cells>

FIG. 30 suggests the possibility that galectin-9 increases the CD11c expression in macrophages differentiated with M-CSF, thereby causing the macrophages to differentiate into dendritic cells. As has been reported, galectin-9 promotes differentiation of human peripheral blood mononuclear cells to conventional dendritic cells (Dai, S. Y. et al, J Immunol, 2005 175: 2974-81). Thus, in the present example, the phenotype of the obtained cells was examined closely. The results thereof are shown in FIG. 31.

(A) Analysis by flow cytometry revealed that the galectin-9 increased the expressions of B220 and I-A/I-E and decreased the expression of CD14. On the other hand, F4/80 used widely as a macrophage marker was expressed at a high level despite the addition of the galectin-9, and maintained the macrophage phenotype.

(B) mRNAs of transcription factors were analyzed by the real-time RT-PCR. As a result, IRF4 and IRF8 necessary for differentiation into dendritic cells were increased by the galectin-9. Also, SpiB, which is considered to be expressed in pDC precursor cells, was increased by the galectin-9, and Id2, which is considered to inhibit the transcription factor E2-2 of mature pDC, also was increased by the addition of the galectin-9.

(C) Furthermore, mRNAs of TLR7, TLR8, and TLR9 also were increased by the addition of the galectin-9.

Figure 31A:
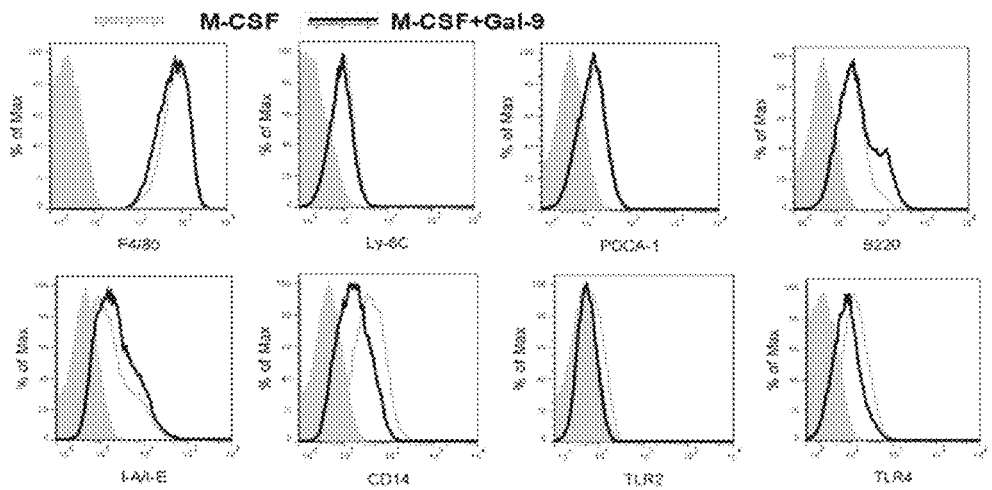
FIG. 31A shows the results of analysis by flow cytometry. The histogram painted with gray shows the result obtained in the case of the isotype control; the histogram plotted with the gray solid line shows the result obtained when the macrophages differentiated with M-CSF were stained with the indicated antibodies; and the histogram plotted with the black solid line shows the result obtained when the macrophages differentiated with M-CSF and galectin-9 were stained with the indicated antibodies.
(B) The mRNA expressions of transcription factors of the above-described cells were analyzed by real-time RT-PCR. The vertical axis of each graph in FIG. 31B shows the result of normalizing the thus-determined mRNA expression levels with the mRNA expression of β2 microglobulin or glyceraldehyde-3-phosphate dehydrogenase. Statistical analysis was performed using four samples for each group.
(C) The mRNA expression of the Toll-like receptor of the above-described cells was analyzed by real-time RT-PCR. The vertical axis of FIG. 31C shows the result of normalizing the thus-determined mRNA expression level with the mRNA expression of 62 2microglobulin or glyceraldehyde-3-phosphate dehydrogenase (Relative mRNA level). Statistical analysis was performed using four samples for each group.
(D) Toll-like receptor agonists indicated in FIG. 31D were added to the above-described cells. 6 hours later, the mRNA expressions of IFN-α and IFN-β were analyzed by real-time RT-PCR. The vertical axis of FIG. 31D shows the result of normalizing the thus-determined mRNA expression level with the mRNA expression of β2 microglobulin or glyceraldehyde-3-phosphate dehydrogenase. Statistical analysis was performed using four samples for each group. "Stimulated with" on the horizontal axis indicates the agonist (or PBS as a control) used for stimulation.
Figure 31B:
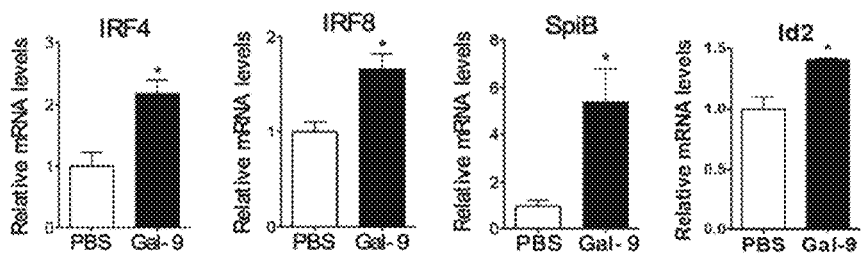
FIG. 31 shows the results verifying that CD11c positive cells differentiated with galectin-9 and M-CSF are precursor cells of pDC-like macrophages in still another example of the present invention.
Figure 31C:
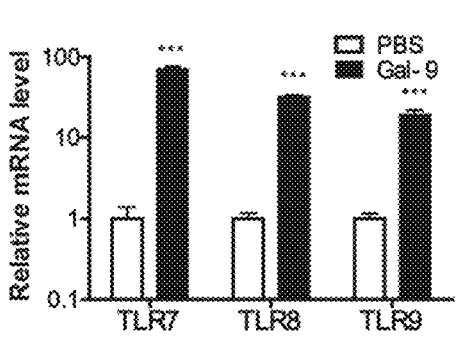
Figure 31D:
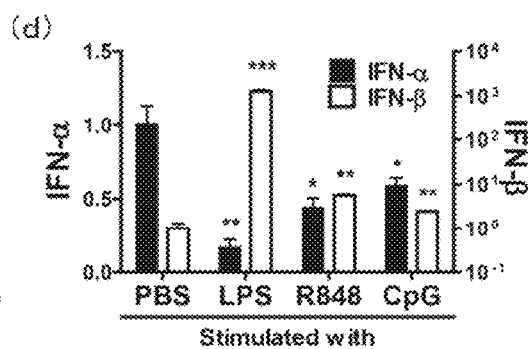

(D) Macrophages were differentiated for 7 days in the presence of M-CSF and galectin-9. Thereafter, the TLR agonists indicated in FIG. 31D were added, and the macrophages were cultured for 6 hours. FIG. 31D shows the results of measuring the mRNA expressions of IFN-α and IFN-β by the real-time RT-PCR. The agonists used in this experiment were: LPS (100 ng/ml, Sigma) as a TLR4 agonist; R848 (5 μg/ml, Imgenex) as a TLR7/8 agonist; and CpG (TypeA CpG ODN1585, 10 μg/ml, Invivogen) as a TLR9 agonist. If the macrophages were mature pDC, high expression of type I interferon should be observed by the stimulation with these TLR agonists. However, the expression of type I interferon was not increased to a high level.

From these results, it is considered that the macrophages differentiated with M-CSF and the stabilized human galectin-9 had not yet become mature pDC although they exhibited a phenotype similar to pDC. Thus, they are considered to be pDC-like macrophage precursors. Accordingly, it is suggested that galectin-9 induces differentiation of macrophages to pDC-like macrophages.

<CD11c Positive Cells Differentiated with Galectin-9 and M-CSF are Matured to pDC-Like Macrophages by LPS Stimulation>

As shown in FIG. 32, CD11c positive cells differentiated with galectin-9 and M-CSF were matured to pDC-like macrophage by LPS stimulation.

Figure 32A:
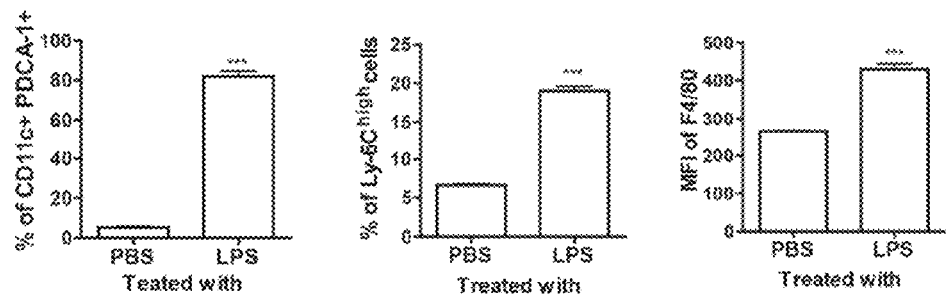
FIG. 32A shows the results obtained when macrophages differentiated with M-CSF and galectin-9 by the method of FIG. 30 were cultured for 24 hours (control; PBS) in LPS, and the expressions of CD11c, PDCA-1, F4/80, and Ly-6C were analyzed by flow cytometry.
(B) Macrophages differentiated with M-CSF and galectin-9 by the method of FIG. 30 were cultured in LPS for 6 hours or 24 hours. The vertical axis of each graph in FIG. 32B shows the result of analyzing the expression of the indicated mRNAs by real-time RT-PCR (relative mRNA level).
(C)

(A) From the results of the previous experiments, it was found that galectin-9 differentiates macrophages differentiated with M-CSF to cells having presumably a phenotype of pDC-like macrophage precursors. This time, whether or not the differentiation of these cells into pDC-like macrophages is caused to proceed by LPS stimulation was examined. The macrophages differentiated with M-CSF and galectin-9 by the method described with reference to FIG. 30 were cultured in 100 ng/ml LPS (control: PBS) for 24 hours. FIG. 32A shows the results of analyzing the expressions of CD11c, Ly-6C, and F4/80 by flow cytometry. Statistical analysis was performed using four samples for each group. By the LPS stimulation, the proportion of cells double positive for CD11c and PDCA-1 (the phenotype of pDC) was increased, and also, the expressions of Ly-6C and F4/80 (the phenotype of macrophages) were increased. This is considered to be the result from the fact that the LPS stimulation caused the proceeding of the differentiation of the cells, whereby the precursors became more mature pDC-like macrophages.

Figure 32B:
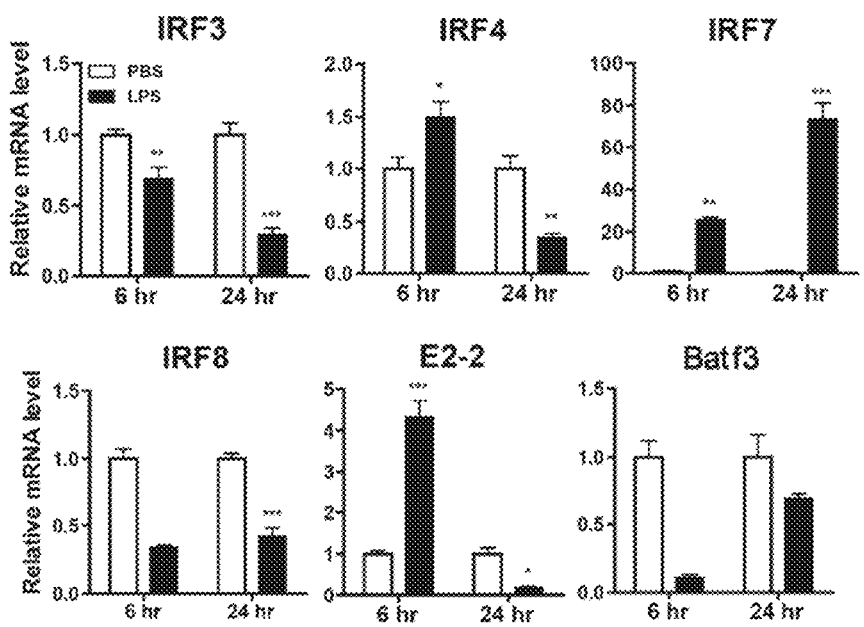
FIG. 32 shows the results demonstrating that CD11c positive cells differentiated with galectin-9 and M-CSF were matured to pDC-like macrophages by LPS stimulation in still another example of the present invention.
(A)
FIG. 32C shows an example of the results obtained when macrophages differentiated with M-CSF and galectin-9 by the method of FIG. 30 were cultured in LPS for 24 hours (control; PBS)), and the expression of I-A/I-E was analyzed by flow cytometry. The gray histogram shows the result obtained in the case of the isotype control; the histogram plotted with the dashed line shows the result obtained in the case of the PBS control; and the histogram plotted with the solid line shows the result obtained in the case of the LPS stimulation. The bar graph in FIG. 32C shows the results of statistically analyzing the proportion of I-A/I-E positive cells in the LPS-treated group and the control PBS group (n=4 in each group).

(B) Macrophages differentiated with M-CSF and galectin-9 by the method of FIG. 30 were cultured 6 hours or 24 hours in 100 ng/ml LPS (control: PBS). FIG. 32B shows the results of measuring the mRNA expressions of the substances indicated therein by the real-time RT-PCR. The mRNA expression levels were normalized with the mRNA expression of β2 microglobulin or glyceraldehyde-3-phosphate dehydrogenase, and are shown in the vertical axis. Statistical analysis was performed using four samples for each group. P<0.01, *P<0.001. The LPS stimulation markedly increased IRF7, which is a transcription factor essential for the expression of type I interferon characterizing pDC. E2-2, which is considered to be expressed at a high level in mature pDC, was increased markedly by the LPS treatment for 6 hours, whereas it decreased after the LPS treatment for 24 hours. *P<0.05, P<0.01, *P<0.001.

Figure 32C:
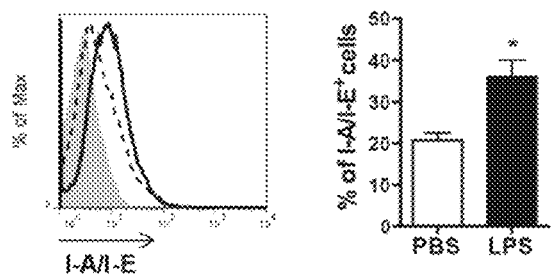

(C) FIG. 32C shows an example of the results obtained when macrophages differentiated with M-CSF and galectin-9 by the method of FIG. 30 were cultured in 100 ng/ml LPS (control; PBS) for 24 hours, and the expression of I-A/I-E was analyzed by flow cytometry. The gray histogram shows the result obtained in the case of the isotype control; the histogram plotted with the dashed line shows the result obtained in the case of the PBS control; and the histogram plotted with the solid line shows the result obtained in the case of the LPS stimulation. The bar graph shows the results of statistically analyzing the proportions of I-A/I-E positive cells in the LPS-treated group and the control PBS group (n=4 in each group). The expression of I-A/I-E was increased by the LPS stimulation. *P<0.05.

From these results, it was verified that macrophages having differentiated to cells considered to be pDC-like macrophage precursors with galectin-9 exhibit the mature pDC-like macrophage phenotype by LPS stimulation.

Figure 33A:
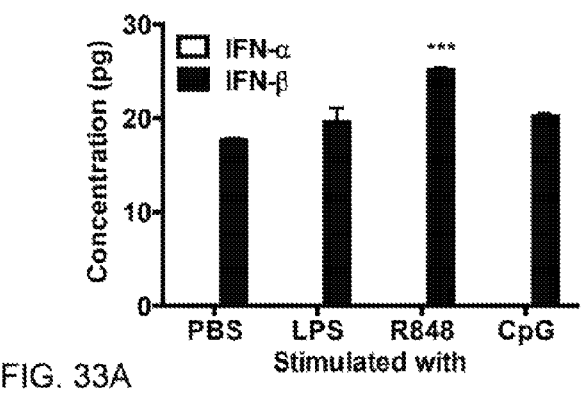
FIG. 33A shows the results of examining IFN-α and IFN-β in the supernatant by ELISA. The vertical axis indicates the concentration. Statistical analysis was performed using four samples for each group. ***P<0.001.
(B)

FIG. 32 shows that pDC-like macrophage precursors differentiated with galectin-9 are caused to exhibit a phenotype of mature pDC-like macrophages by LPS stimulation. The present example further examined the functions of the thus-obtained mature pDC-like macrophages. The results thereof are shown in FIG. 33.

(A) It is known that pDC expresses a high level of type I interferon. Thus, whether or not pDC-like macrophages maturated in vitro secrete IFN-α and IFN-β (typical type I interferons) was examined by ELISA. To pDC-like macrophages subjected to LPS stimulation for 24 hours by the method described with reference to FIG. 32, the TLR agonists (control; PBS) indicated on the horizontal axis of FIG. 33A were added. The concentrations of IFN-α and IFN-β in the supernatant obtained after 18 hours of culture were quantified by a specific ELISA kit purchased from PBL Interferon Source. The vertical axis indicates the thus-quantified concentrations. Statistical analysis was performed using four samples for each group. ***P<0.001. The concentrations of the TRL agonists used were as follows: LPS: 100 ng/ml; R848: 5 μg/ml; and CpG: 10 μg/ml. As a result, the production of IFN-β was observed, and the expression of IFN-β was found to be increased by R848 (TLR7/8 agonist) as compared with that in the control.

Figure 33B:
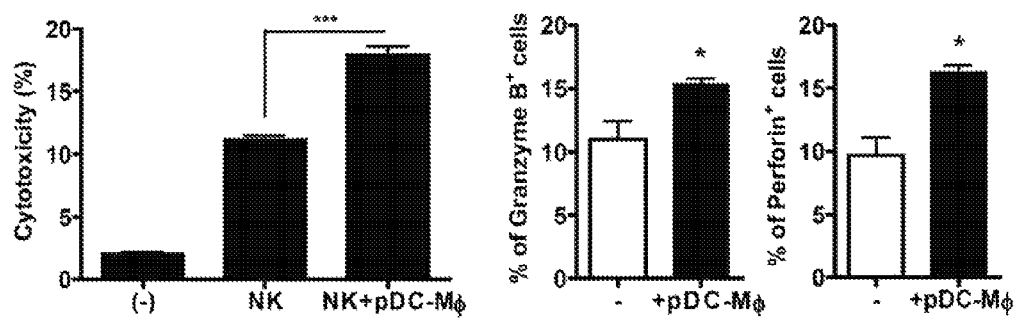
FIG. 33B shows the results of examining whether the pDC-like macrophages matured by being subjected to the LPS stimulation by the method of FIG. 32A activate NK cells to enhance the anti-cancer activity. On the horizontal axis of the left graph, "NK" indicates the result obtained when mouse lymphoma Yac-1 cells and mouse-derived naïve NK cells were co-cultured (Yac-1: NK=1:30); "NK+ pDC-Mϕ" indicates the result obtained when Yac-1, naïve NK, and mature pDC-like macrophages were co-cultured (Yac-1: naïve NK; mature pDC-like macrophages=1:30:60); and "(-)" indicates the result obtained when Yac-1 cells were cultured alone. The vertical axis of the left graph of FIG. 33B indicates the results of analyzing the proportion of dead Yac-1 cells after 5 hours of culture in each of the above cases by flow cytometry. Statistical analysis was performed using four samples for each group. ***P<0.001. The two graphs on the right show the results obtained when the naïve NK cells and the mature pDC-like macrophages were co-cultured for 5 hours, and the expressions of Granzyme B and Perforin in the NK cells were examined by flow cytometry, respectively. Statistical analysis was performed using four samples for each group. *P<0.05.

(B) FIG. 33B shows the results of examining whether pDC-like macrophages maturated in vitro exhibit an anti-cancer action. As cancer cells, mouse lymphoma YAC-1 cells were used. These cells were stained with a cell membrane-staining dye, $DIOC_{18(3)}$ (3,39-dioctadecyloxacarbocyanine perchlorate, Sigma). The cell death of the Yac-1 cells was examined in the case where: the Yac-1 cells were co-cultured with 30 times as many naïve NK cells as the Yac-1 cells; and the Yac-1 cells were co-cultured with, in addition to the above-described naïve NK cells, twice as many mature pDC-like macrophages differentiated in vitro as the Yac-1 cells. The naïve NK cells were purified from mouse spleen cells using MACS Anti-DX5 beads (Miltenyi Biotech). The co-culture was performed for 5 hours, and thereafter, dead cells were stained with propidium iodide. The percentage of dead cells in the DIOC18(3) positive cells (total Yac-1 cells) was analyzed by flow cytometry. As a control, the Yac-1 cells also were cultured alone (the sample indicated as (-) on the horizontal axis). Statistical analysis was performed using four samples for each group.

*P<0.001. As a result, the anti-cancer activity by the NK cells was increased significantly by the pDC-like macrophages matured in vitro. As to the anti-cancer activity by the NK cells, cytotoxic proteins, granzyme B and perforin, contained in and released by the NK cells are chiefly responsible for it. Thus, the following experiment was performed. pDC-like macrophages matured in vitro and NK cells present at the above-described ratio were co-cultured for 5 hours. A Cytofix/Cytoperm solution (BD Biosciences) was used to immobilize the co-cultured cells and to make their cell membranes permeable. The cells were then stained with an anti-Granzyme B antibody (Clone 16G6, eBiosciences) and an anti-Perforin antibody (Clone eBioMAK-D, eBiosciences), and analyzed by flow cytometry. The results thereof are shown in FIG. 33**B. As a control, the NK cells also were cultured alone (in the graph, indicated as "-" on the horizontal axis). Statistical analysis was performed using four samples for each group. As a result, it was found that pDC-like macrophages matured in vitro increases the expression of granzyme B and perforin in NK cells.

From these results, it was verified that galectin-9 promotes the differentiation into pDC-like macrophages in vitro, and also that, by maturing these cells with LPS, the anti-cancer actions via the activation of NK cells is enhanced. As shown in FIG. 29, administration of galectin-9 allows prolonged survival of cancer-carrying mice, and pDC-like macrophages are increased at this time. It is considered that pDC-like macrophages enhance anti-cancer actions of living organisms via activation of NK cells as shown in FIG. 33 etc., which contributes to the prolonged survival of the cancer-carrying mice.

<Reference Example>

Table 2 below shows the result of analyzing various pharmacokinetic parameters by moment analysis, based on the results of the examination on blood kinetics of stabilized human galectin-9 (FIG. 2). In Table 2 below, "Model Independent Pharmacokinetic Analysis" means the model-independent pharmacokinetics analysis. "Dose" means the dose of stabilized human galectin-9. "Cmax" means the peak serum concentration. "Tmax" means the time to reach the peak serum concentration. "AUC" means the area under the serum concentration-time curve. "t1/2" means the half-life. "MRT" means the mean residence time. "CLtot" means the total systemic clearance.

TABLE 2

Model Independent Pharmacokinetic Analysis (Moment)

| Dose (mg/kg) | Cmax (ng/mL) | Tmax (hr) | AUC (∞) (ng*hr/mL) | $t^{1/2}$ (hr) | MRT (hr) | CLtot (L/hr) |
|---|---|---|---|---|---|---|
| 0.02 | 0.019 | 4 | 0.24 | 9.9 | 16 | 12.7 |
| 0.06 | 0.063 | 4 | 0.61 | 3.9 | 5 | 16.4 |
| 0.2 | 0.446 | 1 | 9.52 | 5.2 | 12.2 | 3.2 |
| 0.6 | 0.943 | 2 | 16.86 | 7.6 | 12.5 | 5.9 |
| 2 | 2.552 | 4 | 43.73 | 13.2 | 16.2 | 6.9 |

INDUSTRIAL APPLICABILITY

As specifically described above, the cell of the present invention (e.g., $T_H$GAL9 cell or the like) can contribute to, for example, treatment or reduction of symptoms of autoimmune diseases, allergic diseases, tumors, and other diseases through immune regulation via secretion of galectin-9 in vivo. Furthermore, galectin-9 on a cell surface of the cell of the present invention can serve as an excellent marker for identifying a type 1 T regulatory cell (Tr1 cell) that secretes galectin-9 and IL-10, for example. Thus, by utilizing this marker, the cell of the present invention can be applied to Tr1 cell separation.

The present invention is by no means limited by the above descriptions and the above embodiments and examples. Various changes and modifications may be made without departing from the scope of the present invention.

[Sequence Listing]
TF11056WO Sequence List 2011.12.09.ST25.txt

The invention claimed is:

1. A method for increasing a proportion of animal cells capable of secreting galectin-9, the method comprising:
   culturing animal cells under any of the following conditions 1) to 3):
   1) in the presence of T cell receptor (TCR) stimulation,
   2) in the presence of galectin-9, and
   3) in the presence of both TCR stimulation and galectin-9;
   and thereby increasing the proportion of animal cells capable of secreting galectin-9.

2. The method according to claim 1, wherein the animal cells increased in proportion comprise T cells.

3. The method according to claim 2, wherein the animal cells increased in proportion comprise CD4 positive T cells.

4. The method according to claim 3, wherein the animal cells increased in proportion comprise follicular B helper T cells (TFH cells).

5. The method according to claim 1, wherein the animal cells increased in proportion comprise γδT cells.

6. The method according to claim 1, wherein the animal cells increased in proportion comprise natural killer cells (NK cells).

7. The method according to claim 1, wherein the animal cells increased in proportion comprise B cells.

8. The method according to claim 1, wherein the animal cells increased in proportion comprise NKT cells.

9. The method according to claim 1, wherein the animal cells increased in proportion comprise conventional dendritic cells (cDCs).

10. The method according to claim 1, wherein the animal cells increased in proportion comprise plasmacytoid dendritic cells (pDCs).

11. The method according to claim 1, wherein the animal cells increased in proportion comprise pDC-like macrophages (pDC-Mφs).

12. The method according to claim 2, wherein the animal cells increased in proportion comprise cells capable of increased CD25 expression and galectin-9 and interleukin 10 (IL-10) secretion by T cell receptor (TCR) stimulation.

13. The method according to claim 2, wherein the animal cells increased in proportion comprise cells that do not express Foxp3.

14. The method according to claim 1, wherein the galectin-9 cultured with the animal cells has the amino acid sequence of SEQ ID NO: 6.

\* \* \* \* \*

SEQUENCE LISTING

<160> NUMBER OF SEQ ID NOS: 11

<210> SEQ ID NO 1
<211> LENGTH: 30
<212> TYPE: DNA
<213> ORGANISM: Artificial
<220> FEATURE:
<223> OTHER INFORMATION: synthetic construct; primer

<400> SEQUENCE: 1
cgtcctcata tggccttcag cggttcccag                               30

<210> SEQ ID NO 2
<211> LENGTH: 33
<212> TYPE: DNA
<213> ORGANISM: Artificial
<220> FEATURE:
<223> OTHER INFORMATION: synthetic construct; primer

<400> SEQUENCE: 2
cgaccgcata tgctggaagc tgatgtagga cag                           33

<210> SEQ ID NO 3
<211> LENGTH: 33

```
<212> TYPE: DNA
<213> ORGANISM: Artificial
<220> FEATURE:
<223> OTHER INFORMATION: synthetic construct; primer

<400> SEQUENCE: 3
cgtcctcata tgactcccgc catcccacct atg                              33

<210> SEQ ID NO 4
<211> LENGTH: 33
<212> TYPE: DNA
<213> ORGANISM: Artificial
<220> FEATURE:
<223> OTHER INFORMATION: synthetic construct; primer

<400> SEQUENCE: 4
cgaccgggat ccctatgtct gcacatgggt cag                              33

<210> SEQ ID NO 5
<211> LENGTH: 891
<212> TYPE: DNA
<213> ORGANISM: Artificial
<220> FEATURE:
<223> OTHER INFORMATION: synthetic construct; Polynucleotide for
      galectin-9 mutein
<220> FEATURE:
<221> NAME/KEY: CDS
<222> LOCATION: (1)..(891)

<400> SEQUENCE: 5
```

| | | | | | | | | | | | | | | | | |
|---|---|---|---|---|---|---|---|---|---|---|---|---|---|---|---|---|
| atg | gcc | ttc | agc | ggt | tcc | cag | gct | ccc | tac | ctg | agt | cca | gct | gtc | ccc | 48 |
| Met | Ala | Phe | Ser | Gly | Ser | Gln | Ala | Pro | Tyr | Leu | Ser | Pro | Ala | Val | Pro | |
| 1 | | | | 5 | | | | | 10 | | | | | 15 | | |
| ttt | tct | ggg | act | att | caa | gga | ggt | ctc | cag | gac | gga | ctt | cag | atc | act | 96 |
| Phe | Ser | Gly | Thr | Ile | Gln | Gly | Gly | Leu | Gln | Asp | Gly | Leu | Gln | Ile | Thr | |
| | | | 20 | | | | | 25 | | | | | 30 | | | |
| gtc | aat | ggg | acc | gtt | ctc | agc | tcc | agt | gga | acc | agg | ttt | gct | gtg | aac | 144 |
| Val | Asn | Gly | Thr | Val | Leu | Ser | Ser | Ser | Gly | Thr | Arg | Phe | Ala | Val | Asn | |
| | | 35 | | | | | 40 | | | | | 45 | | | | |
| ttt | cag | act | ggc | ttc | agt | gga | aat | gac | att | gcc | ttc | cac | ttc | aac | cct | 192 |
| Phe | Gln | Thr | Gly | Phe | Ser | Gly | Asn | Asp | Ile | Ala | Phe | His | Phe | Asn | Pro | |
| | 50 | | | | | 55 | | | | | 60 | | | | | |
| cgg | ttt | gaa | gat | gga | ggg | tac | gtg | gtg | tgc | aac | acg | agg | cag | aac | gga | 240 |
| Arg | Phe | Glu | Asp | Gly | Gly | Tyr | Val | Val | Cys | Asn | Thr | Arg | Gln | Asn | Gly | |
| 65 | | | | | 70 | | | | | 75 | | | | | 80 | |
| agc | tgg | ggg | ccc | gag | gag | agg | aag | aca | cac | atg | cct | ttc | cag | aag | ggg | 288 |
| Ser | Trp | Gly | Pro | Glu | Glu | Arg | Lys | Thr | His | Met | Pro | Phe | Gln | Lys | Gly | |
| | | | | 85 | | | | | 90 | | | | | 95 | | |
| atg | ccc | ttt | gac | ctc | tgc | ttc | ctg | gtg | cag | agc | tca | gat | ttc | aag | gtg | 336 |
| Met | Pro | Phe | Asp | Leu | Cys | Phe | Leu | Val | Gln | Ser | Ser | Asp | Phe | Lys | Val | |
| | | | 100 | | | | | 105 | | | | | 110 | | | |
| atg | gtg | aac | ggg | atc | ctc | ttc | gtg | cag | tac | ttc | cac | cgc | gtg | ccc | ttc | 384 |
| Met | Val | Asn | Gly | Ile | Leu | Phe | Val | Gln | Tyr | Phe | His | Arg | Val | Pro | Phe | |
| | | 115 | | | | | 120 | | | | | 125 | | | | |
| cac | cgt | gtg | gac | acc | atc | tcc | gtc | aat | ggc | tct | gtg | cag | ctg | tcc | tac | 432 |
| His | Arg | Val | Asp | Thr | Ile | Ser | Val | Asn | Gly | Ser | Val | Gln | Leu | Ser | Tyr | |
| | 130 | | | | | 135 | | | | | 140 | | | | | |
| atc | agc | ttc | cag | cat | atg | act | ccc | gcc | atc | cca | cct | atg | atg | tac | ccc | 480 |
| Ile | Ser | Phe | Gln | His | Met | Thr | Pro | Ala | Ile | Pro | Pro | Met | Met | Tyr | Pro | |
| 145 | | | | | 150 | | | | | 155 | | | | | 160 | |
| cac | ccc | gcc | tat | ccg | atg | cct | ttc | atc | acc | acc | att | ctg | gga | ggg | ctg | 528 |
| His | Pro | Ala | Tyr | Pro | Met | Pro | Phe | Ile | Thr | Thr | Ile | Leu | Gly | Gly | Leu | |
| | | | | 165 | | | | | 170 | | | | | 175 | | |

| | | |
|---|---|---|
| tac cca tcc aag tcc atc ctc ctg tca ggc act gtc ctg ccc agt gct<br>Tyr Pro Ser Lys Ser Ile Leu Leu Ser Gly Thr Val Leu Pro Ser Ala<br>           180                           185                   190 | | 576 |
| cag agg ttc cac atc aac ctg tgc tct ggg aac cac atc gcc ttc cac<br>Gln Arg Phe His Ile Asn Leu Cys Ser Gly Asn His Ile Ala Phe His<br>      195   &nbsd;                200                  205 | | 624 |
| ctg aac ccc cgt ttt gat gag aat gct gtg gtc cgc aac acc cag atc<br>Leu Asn Pro Arg Phe Asp Glu Asn Ala Val Val Arg Asn Thr Gln Ile<br>210                         215                     220 | | 672 |
| gac aac tcc tgg ggg tct gag gag cga agt ctg ccc cga aaa atg ccc<br>Asp Asn Ser Trp Gly Ser Glu Glu Arg Ser Leu Pro Arg Lys Met Pro<br>225                       230                    235                  240 | | 720 |
| ttc gtc cgt ggc cag agc ttc tca gtg tgg atc ttg tgt gaa gct cac<br>Phe Val Arg Gly Gln Ser Phe Ser Val Trp Ile Leu Cys Glu Ala His<br>                      245                    250                  255 | | 768 |
| tgc ctc aag gtg gcc gtg gat ggt cag cac ctg ttt gaa tac tac cat<br>Cys Leu Lys Val Ala Val Asp Gly Gln His Leu Phe Glu Tyr Tyr His<br>              260                    265                  270 | | 816 |
| cgc ctg agg aac ctg ccc acc atc aac aga ctg gaa gtg ggg ggc gac<br>Arg Leu Arg Asn Leu Pro Thr Ile Asn Arg Leu Glu Val Gly Gly Asp<br>     275                      280                  285 | | 864 |
| atc cag ctg acc cat gtg cag aca tag<br>Ile Gln Leu Thr His Val Gln Thr<br>     290                      295 | | 891 |

```
<210> SEQ ID NO 6
<211> LENGTH: 296
<212> TYPE: PRT
<213> ORGANISM: Artificial
<220> FEATURE:
<223> OTHER INFORMATION: synthetic construct; Polynucleotide for
      galectin-9 mutein

<400> SEQUENCE: 6

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln His Met Thr Pro Ala Ile Pro Pro Met Met Tyr Pro
145                 150                 155                 160

His Pro Ala Tyr Pro Met Pro Phe Ile Thr Thr Ile Leu Gly Gly Leu
                165                 170                 175

Tyr Pro Ser Lys Ser Ile Leu Leu Ser Gly Thr Val Leu Pro Ser Ala
            180                 185                 190
```

```
Gln Arg Phe His Ile Asn Leu Cys Ser Gly Asn His Ile Ala Phe His
            195                 200                 205

Leu Asn Pro Arg Phe Asp Glu Asn Ala Val Val Arg Asn Thr Gln Ile
        210                 215                 220

Asp Asn Ser Trp Gly Ser Glu Glu Arg Ser Leu Pro Arg Lys Met Pro
225                 230                 235                 240

Phe Val Arg Gly Gln Ser Phe Ser Val Trp Ile Leu Cys Glu Ala His
                245                 250                 255

Cys Leu Lys Val Ala Val Asp Gly Gln His Leu Phe Glu Tyr Tyr His
            260                 265                 270

Arg Leu Arg Asn Leu Pro Thr Ile Asn Arg Leu Glu Val Gly Gly Asp
        275                 280                 285

Ile Gln Leu Thr His Val Gln Thr
        290                 295

<210> SEQ ID NO 7
<211> LENGTH: 148
<212> TYPE: PRT
<213> ORGANISM: Homo sapiens

<400> SEQUENCE: 7

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln
145

<210> SEQ ID NO 8
<211> LENGTH: 146
<212> TYPE: PRT
<213> ORGANISM: Homo sapiens

<400> SEQUENCE: 8

Thr Pro Ala Ile Pro Pro Met Met Tyr Pro His Pro Ala Tyr Pro Met
1               5                   10                  15

Pro Phe Ile Thr Thr Ile Leu Gly Gly Leu Tyr Pro Ser Lys Ser Ile
            20                  25                  30

Leu Leu Ser Gly Thr Val Leu Pro Ser Ala Gln Arg Phe His Ile Asn
        35                  40                  45
```

```
Leu Cys Ser Gly Asn His Ile Ala Phe His Leu Asn Pro Arg Phe Asp
        50                  55                  60

Glu Asn Ala Val Val Arg Asn Thr Gln Ile Asp Asn Ser Trp Gly Ser
 65              70                  75                  80

Glu Glu Arg Ser Leu Pro Arg Lys Met Pro Phe Val Arg Gly Gln Ser
                 85                  90                  95

Phe Ser Val Trp Ile Leu Cys Glu Ala His Cys Leu Lys Val Ala Val
            100                 105                 110

Asp Gly Gln His Leu Phe Glu Tyr Tyr His Arg Leu Arg Asn Leu Pro
            115                 120                 125

Thr Ile Asn Arg Leu Glu Val Gly Gly Asp Ile Gln Leu Thr His Val
            130                 135                 140

Gln Thr
145

<210> SEQ ID NO 9
<211> LENGTH: 17
<212> TYPE: PRT
<213> ORGANISM: Homo sapiens

<400> SEQUENCE: 9

Thr Gln Thr Val Ile His Thr Val Gln Ser Ala Pro Gly Gln Met Phe
 1               5                  10                  15

Ser

<210> SEQ ID NO 10
<211> LENGTH: 61
<212> TYPE: PRT
<213> ORGANISM: Homo sapiens

<400> SEQUENCE: 10

Asn Pro Arg Thr Val Pro Val Gln Pro Ala Phe Ser Thr Val Pro Phe
 1               5                  10                  15

Ser Gln Pro Val Cys Phe Pro Pro Arg Pro Arg Gly Arg Arg Gln Lys
                20                  25                  30

Pro Pro Gly Val Trp Pro Ala Asn Pro Ala Pro Ile Thr Gln Thr Val
            35                  40                  45

Ile His Thr Val Gln Ser Ala Pro Gly Gln Met Phe Ser
        50                  55                  60

<210> SEQ ID NO 11
<211> LENGTH: 29
<212> TYPE: PRT
<213> ORGANISM: Homo sapiens

<400> SEQUENCE: 11

Pro Pro Gly Val Trp Pro Ala Asn Pro Ala Pro Ile Thr Gln Thr Val
 1               5                  10                  15

Ile His Thr Val Gln Ser Ala Pro Gly Gln Met Phe Ser
                20                  25
```